US009877895B2

(12) United States Patent
Garfield et al.

(10) Patent No.: US 9,877,895 B2
(45) Date of Patent: Jan. 30, 2018

(54) COMPOUNDING SYSTEMS AND METHODS FOR SAFE MEDICAMENT TRANSPORT

(71) Applicants: J&J SOLUTIONS, INC., Coralville, IA (US); Jared Garfield, North Liberty, IA (US); Gregory Lyon, Mamaroneck, NY (US)

(72) Inventors: Jared Garfield, North Liberty, IA (US); Gregory Lyon, Mamaroneck, NY (US)

(73) Assignee: J&J SOLUTIONS, INC., Coralville, IA (US)

( * ) Notice: Subject to any disclaimer, the term of this patent is extended or adjusted under 35 U.S.C. 154(b) by 7 days.

(21) Appl. No.: 14/908,169

(22) PCT Filed: Aug. 4, 2014

(86) PCT No.: PCT/US2014/049609
§ 371 (c)(1),
(2) Date: Jan. 28, 2016

(87) PCT Pub. No.: WO2015/017858
PCT Pub. Date: Feb. 5, 2015

(65) Prior Publication Data
US 2016/0206511 A1 Jul. 21, 2016

Related U.S. Application Data

(60) Provisional application No. 61/861,680, filed on Aug. 2, 2013, provisional application No. 61/984,144, filed on Apr. 25, 2014.

(51) Int. Cl.
*A61J 1/20* (2006.01)
*B65B 3/00* (2006.01)
(Continued)

(52) U.S. Cl.
CPC .............. *A61J 1/2096* (2013.01); *A61J 1/20* (2013.01); *A61J 1/2003* (2015.05); *A61J 1/2089* (2013.01);
(Continued)

(58) Field of Classification Search
CPC .. A61J 1/20; A61J 1/201; A61J 1/2003; A61J 1/2072; A61J 1/2089; A61J 1/2096;
(Continued)

(56) References Cited

U.S. PATENT DOCUMENTS 3,706,305 A 12/1972 Berger et al.
4,180,070 A 12/1979 Genese
(Continued)

FOREIGN PATENT DOCUMENTS

DE 60-222059 T2 12/2007
EP 0 521 264 A2 1/1993
(Continued)

OTHER PUBLICATIONS

PCT International Preliminary Report and Written Opinion corresponding to counterpart Int'l Appln. No. PCT/US2014/049609 dated Feb. 2, 2016.
(Continued)

*Primary Examiner* — Timothy L Maust
(74) *Attorney, Agent, or Firm* — Carter, DeLuca, Farrell & Schmidt, LLP

(57) ABSTRACT

An automatic or semi-automatic preparation system and process is provided for forming a medicament solution from a vial containing one of a liquid and a non-liquid material.

14 Claims, 56 Drawing Sheets

(51) Int. Cl.
*A61M 5/31* (2006.01)
*B65B 3/12* (2006.01)
*B65B 63/08* (2006.01)
*B65B 3/28* (2006.01)

(52) U.S. Cl.
CPC .............. *A61M 5/31* (2013.01); *B65B 3/003* (2013.01); *B65B 3/12* (2013.01); *B65B 63/08* (2013.01); *A61J 1/201* (2015.05); *A61J 1/2072* (2015.05); *A61M 2005/3114* (2013.01); *B65B 3/28* (2013.01)

(58) Field of Classification Search
CPC .. B65B 3/28; B65B 3/003; B65B 3/12; B65B 63/08; A61M 5/31; A61M 2005/3114
USPC .................................................. 141/319, 329
See application file for complete search history.

(56) References Cited

U.S. PATENT DOCUMENTS

| | | |
|---|---|---|
| 4,201,208 A | 5/1980 | Cambio, Jr. |
| 4,576,211 A | 3/1986 | Valentini et al. |
| 4,673,404 A | 6/1987 | Gustavsson |
| 4,752,292 A | 6/1988 | Lopez et al. |
| 5,100,394 A | 3/1992 | Dudar et al. |
| 5,135,489 A | 8/1992 | Jepson et al. |
| 5,158,554 A | 10/1992 | Jepson et al. |
| 5,167,648 A | 12/1992 | Jepson et al. |
| 5,188,620 A | 2/1993 | Jepson et al. |
| 5,211,638 A | 5/1993 | Dudar et al. |
| 5,405,340 A | 4/1995 | Fageol et al. |
| 5,437,650 A | 8/1995 | Larkin et al. |
| 5,470,327 A | 11/1995 | Helgren et al. |
| 5,507,733 A | 4/1996 | Larkin et al. |
| 5,520,666 A | 5/1996 | Choudhury et al. |
| 5,545,152 A | 8/1996 | Funderburk et al. |
| 5,549,566 A | 8/1996 | Elias et al. |
| 5,580,351 A | 12/1996 | Helgren et al. |
| 5,658,260 A | 8/1997 | Desecki et al. |
| 5,685,842 A | 11/1997 | Drivas |
| 5,702,374 A | 12/1997 | Johnson |
| 5,785,682 A | 7/1998 | Grabenkort |
| 5,785,692 A | 7/1998 | Attermeier et al. |
| 5,797,897 A | 8/1998 | Jepson et al. |
| 5,807,345 A | 9/1998 | Grabenkort |
| 5,810,768 A | 9/1998 | Lopez |
| 5,871,500 A | 2/1999 | Jepson et al. |
| 5,891,129 A | 4/1999 | Daubert et al. |
| 5,899,888 A | 5/1999 | Jepson et al. |
| 5,924,584 A | 7/1999 | Hellstrom et al. |
| 5,954,104 A | 9/1999 | Daubert et al. |
| 5,954,708 A | 9/1999 | Lopez et al. |
| 5,957,898 A | 9/1999 | Jepson et al. |
| 5,964,785 A | 10/1999 | Desecki et al. |
| 6,063,068 A | 5/2000 | Fowles et al. |
| 6,083,194 A | 7/2000 | Lopez |
| 6,090,091 A | 7/2000 | Fowles et al. |
| 6,139,534 A | 10/2000 | Niedospial, Jr. et al. |
| 6,193,697 B1 | 2/2001 | Jepson et al. |
| 6,213,996 B1 | 4/2001 | Jepson et al. |
| 6,245,048 B1 | 6/2001 | Fangrow, Jr. et al. |
| 6,261,266 B1 | 7/2001 | Jepson et al. |
| 6,261,282 B1 | 7/2001 | Jepson et al. |
| 6,302,289 B1 | 10/2001 | Andersson et al. |
| 6,344,033 B1 | 2/2002 | Jepson et al. |
| 6,387,074 B1 | 5/2002 | Horppu et al. |
| 6,394,983 B1 | 5/2002 | Mayoral et al. |
| 6,409,708 B1 | 6/2002 | Wessman |
| 6,428,520 B1 | 8/2002 | Lopez et al. |
| 6,447,498 B1 | 9/2002 | Jepson et al. |
| 6,524,295 B2 | 2/2003 | Daubert et al. |
| 6,569,125 B2 | 5/2003 | Jepson et al. |
| 6,595,964 B2 | 7/2003 | Finley et al. |
| 6,599,273 B1 | 7/2003 | Lopez |
| 6,605,076 B1 | 8/2003 | Jepson et al. |
| 6,605,576 B2 | 8/2003 | Lee |
| 6,635,043 B2 | 10/2003 | Daubert et al. |
| 6,635,044 B2 | 10/2003 | Lopez |
| 6,660,527 B2 | 12/2003 | Stroup |
| 6,669,681 B2 | 12/2003 | Jepson et al. |
| 6,695,817 B1 | 2/2004 | Fangrow, Jr. |
| D488,867 S | 4/2004 | Chau |
| 6,715,520 B2 | 4/2004 | Andreasson et al. |
| 6,871,838 B2 | 3/2005 | Raines et al. |
| 6,874,522 B2 | 4/2005 | Anderson et al. |
| 6,875,205 B2 | 4/2005 | Leinsing |
| 6,915,823 B2 | 7/2005 | Osborne et al. |
| 7,025,389 B2 | 4/2006 | Cuschieri et al. |
| 7,040,598 B2 | 5/2006 | Raybuck |
| 7,044,441 B2 | 5/2006 | Doyle |
| 7,100,891 B2 | 9/2006 | Doyle |
| 7,114,701 B2 | 10/2006 | Peppel |
| 7,175,615 B2 | 2/2007 | Hanly et al. |
| 7,244,249 B2 | 7/2007 | Leinsing et al. |
| 7,306,198 B2 | 12/2007 | Doyle |
| 7,306,584 B2 | 12/2007 | Wessman et al. |
| 7,314,061 B2 | 1/2008 | Peppel |
| 7,316,669 B2 | 1/2008 | Ranalletta |
| 7,358,505 B2 | 4/2008 | Woodworth et al. |
| 7,396,051 B2 | 7/2008 | Baldwin et al. |
| 7,425,209 B2 | 9/2008 | Fowles et al. |
| 7,470,258 B2 | 12/2008 | Barker et al. |
| 7,497,848 B2 | 3/2009 | Leinsing et al. |
| 7,497,849 B2 | 3/2009 | Fangrow, Jr. |
| 7,503,908 B2 | 3/2009 | Bartholomew |
| 7,510,545 B2 | 3/2009 | Peppel |
| 7,563,253 B2 | 7/2009 | Tanner et al. |
| 7,569,036 B2 | 8/2009 | Domkowski et al. |
| 7,569,043 B2 | 8/2009 | Fangrow |
| 7,591,449 B2 | 9/2009 | Raines et al. |
| 7,615,035 B2 | 11/2009 | Peppel |
| 7,645,271 B2 | 1/2010 | Fangrow |
| 7,645,274 B2 | 1/2010 | Whitley |
| 7,651,481 B2 | 1/2010 | Raybuck |
| 7,670,326 B2 | 3/2010 | Shemesh |
| 7,713,247 B2 | 5/2010 | Lopez |
| 7,717,883 B2 | 5/2010 | Lopez |
| 7,717,884 B2 | 5/2010 | Lopez |
| 7,717,886 B2 | 5/2010 | Lopez |
| 7,743,799 B2 | 6/2010 | Mosler et al. |
| 7,744,581 B2 | 6/2010 | Wallen et al. |
| 7,753,085 B2 | 7/2010 | Tribble et al. |
| 7,753,338 B2 | 7/2010 | Desecki |
| 7,758,560 B2 | 7/2010 | Connell et al. |
| 7,762,524 B2 | 7/2010 | Cawthon et al. |
| 7,763,013 B2 | 7/2010 | Baldwin et al. |
| 7,763,199 B2 | 7/2010 | Fangrow, Jr. |
| 7,766,304 B2 | 8/2010 | Phillips |
| 7,766,897 B2 | 8/2010 | Ramsey et al. |
| 7,900,659 B2 | 3/2011 | Whitley et al. |
| 8,043,864 B2 | 10/2011 | Stroup |
| 8,119,419 B2 | 2/2012 | Stroup |
| 8,122,923 B2 | 2/2012 | Kraus et al. |
| 8,251,346 B2 | 8/2012 | Stroup |
| 8,287,513 B2 | 10/2012 | Ellstrom et al. |
| 8,414,554 B2 | 4/2013 | Garfield et al. |
| 8,414,555 B2 | 4/2013 | Garfield et al. |
| 8,414,556 B2 | 4/2013 | Garfield et al. |
| 8,469,940 B2 | 6/2013 | Garfield et al. |
| 8,894,627 B2 | 11/2014 | Garfield et al. |
| 9,039,047 B2 | 5/2015 | Imai |
| 9,220,661 B2 | 12/2015 | Garfield et al. |
| 2002/0115981 A1 | 8/2002 | Wessman |
| 2002/0177819 A1 | 11/2002 | Barker et al. |
| 2003/0070726 A1 | 4/2003 | Andreasson et al. |
| 2003/0187420 A1 | 10/2003 | Akerlund et al. |
| 2004/0124389 A1 | 7/2004 | Phillips |
| 2004/0144668 A1 | 7/2004 | Marshall et al. |
| 2006/0106360 A1 | 5/2006 | Wong |
| 2006/0129109 A1 | 6/2006 | Shaw et al. |
| 2007/0015233 A1 | 1/2007 | Brancia |
| 2007/0079894 A1 | 4/2007 | Kraus et al. |
| 2007/0088315 A1 | 4/2007 | Haindl |

(56) References Cited

U.S. PATENT DOCUMENTS

| | | |
|---|---|---|
| 2007/0101772 A1 | 5/2007 | Duncan et al. |
| 2008/0097371 A1 | 4/2008 | Shemesh |
| 2008/0103455 A1 | 5/2008 | Domkowski et al. |
| 2008/0103485 A1 | 5/2008 | Kruger |
| 2008/0114328 A1 | 5/2008 | Doherty et al. |
| 2008/0142388 A1 | 6/2008 | Whitley et al. |
| 2008/0172024 A1 | 7/2008 | Yow |
| 2008/0223484 A1 | 9/2008 | Horppu |
| 2008/0249498 A1 | 10/2008 | Fangrow |
| 2008/0262465 A1 | 10/2008 | Zinger et al. |
| 2008/0264450 A1 | 10/2008 | Baldwin et al. |
| 2008/0287920 A1 | 11/2008 | Fangrow et al. |
| 2008/0318456 A1 | 12/2008 | Yow et al. |
| 2009/0069783 A1 | 3/2009 | Ellstrom et al. |
| 2009/0216212 A1 | 8/2009 | Fangrow, Jr. |
| 2009/0243281 A1 | 10/2009 | Seifert et al. |
| 2009/0270832 A1 | 10/2009 | Vancaillie et al. |
| 2009/0326506 A1 | 12/2009 | Hasegawa et al. |
| 2010/0004602 A1 | 1/2010 | Nord et al. |
| 2010/0004618 A1 | 1/2010 | Rondeau et al. |
| 2010/0004619 A1 | 1/2010 | Rondeau et al. |
| 2010/0004634 A1 | 1/2010 | Whitley |
| 2010/0036330 A1 | 2/2010 | Plishka et al. |
| 2010/0049160 A1 | 2/2010 | Jepson et al. |
| 2010/0055668 A1 | 3/2010 | Stroup |
| 2010/0106129 A1 | 4/2010 | Goeckner et al. |
| 2010/0108681 A1 | 5/2010 | Jepson et al. |
| 2010/0147402 A1 | 6/2010 | Tornqvist |
| 2010/0152669 A1 | 6/2010 | Rosenquist |
| 2010/0160889 A1 | 6/2010 | Smith et al. |
| 2010/0217226 A1 | 8/2010 | Shemesh |
| 2010/0218846 A1 | 9/2010 | Kriheli |
| 2010/0241088 A1 | 9/2010 | Ranalletta et al. |
| 2010/0249745 A1 | 9/2010 | Ellstrom |
| 2011/0015580 A1 | 1/2011 | Stroup |
| 2011/0049866 A1 | 3/2011 | Trombley, III et al. |
| 2011/0266477 A1 | 11/2011 | Stroup |
| 2012/0048676 A1 | 3/2012 | Giribona et al. |
| 2012/0157914 A1 | 6/2012 | Stroup |
| 2012/0325365 A1 | 12/2012 | Strangis |
| 2013/0000780 A1 | 1/2013 | Garfield et al. |
| 2013/0066293 A1 | 3/2013 | Garfield et al. |
| 2015/0068640 A1 | 3/2015 | Garfield et al. |

FOREIGN PATENT DOCUMENTS

| | | |
|---|---|---|
| EP | 0 667 126 A1 | 8/1995 |
| EP | 1 279 798 A2 | 1/2003 |
| JP | 08-182742 | 7/1996 |
| JP | 2002-126094 A | 5/2002 |
| JP | 2005-522281 A | 7/2005 |
| JP | 2007-509691 A | 4/2007 |
| NO | 99/56812 A2 | 11/1999 |
| WO | 93/20767 A1 | 10/1993 |
| WO | 93/20768 A1 | 10/1993 |
| WO | 96/34571 A1 | 11/1996 |
| WO | 97/48449 A1 | 12/1997 |
| WO | 97/48450 A1 | 12/1997 |
| WO | 97/48451 A1 | 12/1997 |
| WO | 99/56642 A1 | 11/1999 |
| WO | 99/56643 A1 | 11/1999 |
| WO | 00/49957 A1 | 8/2000 |
| WO | 0057811 A1 | 10/2000 |
| WO | 01/60235 | 8/2001 |
| WO | 02/078777 | 10/2002 |
| WO | 03/034932 | 5/2003 |
| WO | 03/039385 | 5/2003 |
| WO | 2003/047043 A1 | 6/2003 |
| WO | 2003/088806 A2 | 10/2003 |
| WO | 2003/088858 | 10/2003 |
| WO | 2005/002492 A1 | 1/2005 |
| WO | 2005/011049 A2 | 2/2005 |
| WO | 2005/041846 A2 | 5/2005 |
| WO | 2006/052655 A2 | 5/2006 |
| WO | 2007/015233 A1 | 2/2007 |
| WO | 2007/101772 A1 | 9/2007 |
| WO | 2008/136720 A1 | 11/2008 |
| WO | 2009/035384 A1 | 3/2009 |
| WO | 2009/133754 A1 | 11/2009 |
| WO | 2009/140511 A1 | 11/2009 |
| WO | 2011/124780 A2 | 10/2011 |
| WO | 2011/150037 A1 | 12/2011 |

OTHER PUBLICATIONS

I Chou, C.K. (1995). "Radiofrequency Hyperthermia in Cancer Therapy," Biologic Effects of Nonionizing Electromagnetic Fields. Chapter 94, CRC Press, Inc. pp. 1424-1428.

Urologix, Inc.—Medical Professionals: Targis3 Technology (a date prior to the filing of the present application) <http://www.urologix.com/medical/technology.html (3> total pages).

International Search Report corresponding to European Application No. EP 06 00 9435.6; completed Jul. 6, 2006 and dated Jul. 13, 2006; 3 pp.

International Search Report corresponding to International Application No. PCT/US2009/043976, completed Jun. 26, 2009 and dated Jul. 28, 2009; 3 pp.

International Search Report and Written Opinion corresponding to PCT/US2011/037873, completed Sep. 6, 2011 and dated Sep. 13, 2011; 34 pp .

New Zealand First Examination Report corresponding to NZ 603808 dated Jul. 11, 2013; 2 pp.

Australian Examination Report No. 1 corresponding to AU 2011258371 dated Dec. 19, 2013; 3 pp.

Canadian Office Action corresponding to CA 2,800,278 dated Jul. 15, 2014; 2 pp.

New Zealand First Examination Report corresponding to NZ 627328 dated Jul. 24, 2014; 2 pp.

New Zealand Further Examination Report corresponding to NZ 603808 dated Sep. 3, 2014; 2 pp.

New Zealand First Examination Report corresponding to NZ 629637 dated Sep. 3, 2014; 2 pp.

New Zealand Further Examination Report corresponding to NZ 627328 dated Feb. 23, 2015; 2 pp.

Japanese Office Action corresponding to JP 2013-512192, dated Mar. 24, 2015 with the English Translation; 8 pp.

Extended European Search Report corresponding to EP 11 78 7309.1 dated Aug. 3, 2015; 9 pp.

Extended European Search Report corresponding to EP 15 17 3144.5 dated Oct. 19, 2015.

Australian Examination Report No. 1 corresponding to AU 2014277764 dated Nov. 13, 2015.

Extended European Search Report corresponding to EP 15 17 6012.1 dated Nov. 13, 2015.

Extended European Search Report corresponding to EP 15 17 6026.1 dated Nov. 13, 2015.

Extended European Search Report corresponding to EP 15 17 6031.1 dated Nov. 19, 2015.

Extended European Search Report corresponding to EP 15 17 6044.4 dated Nov. 23, 2015.

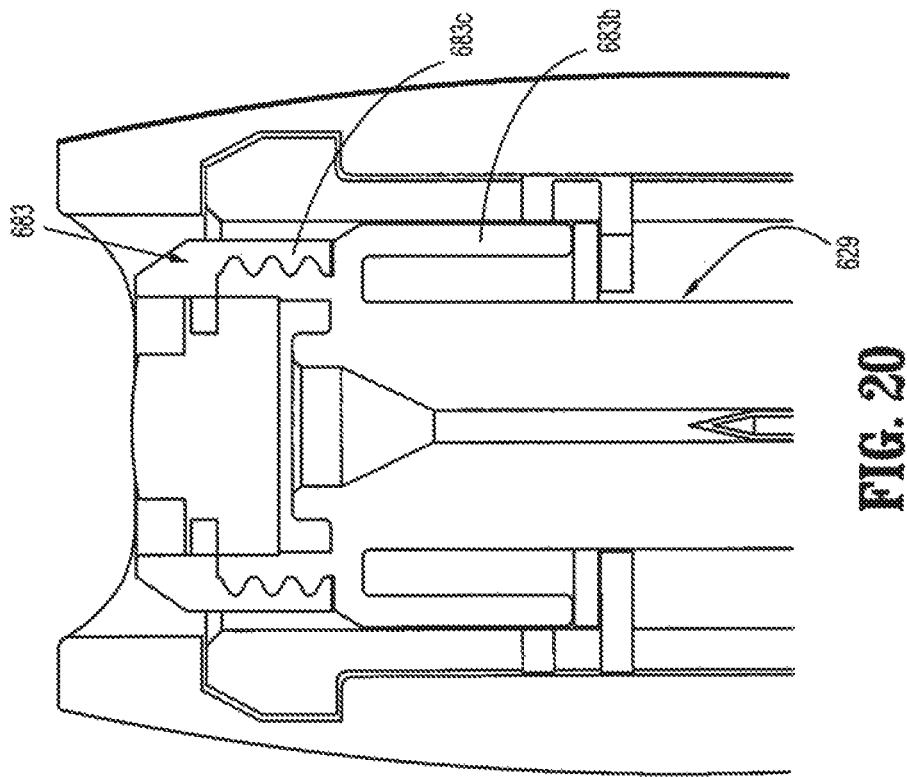
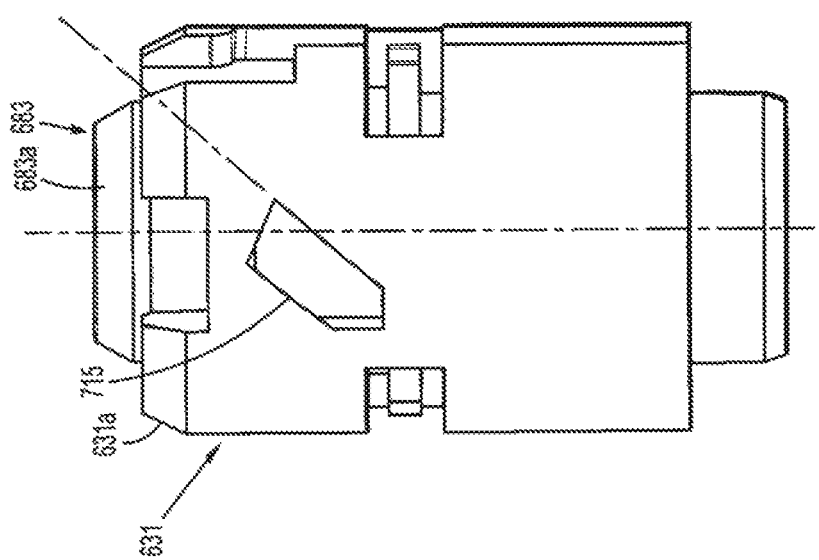

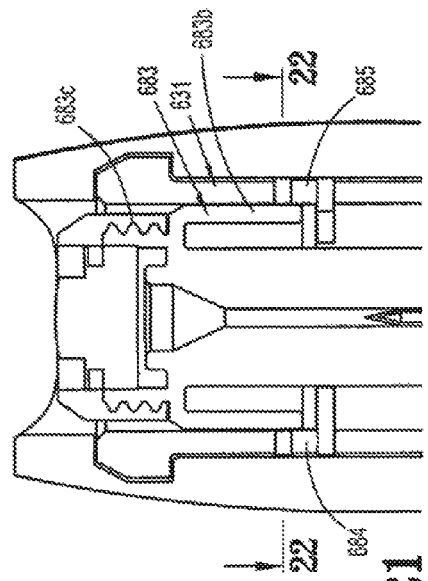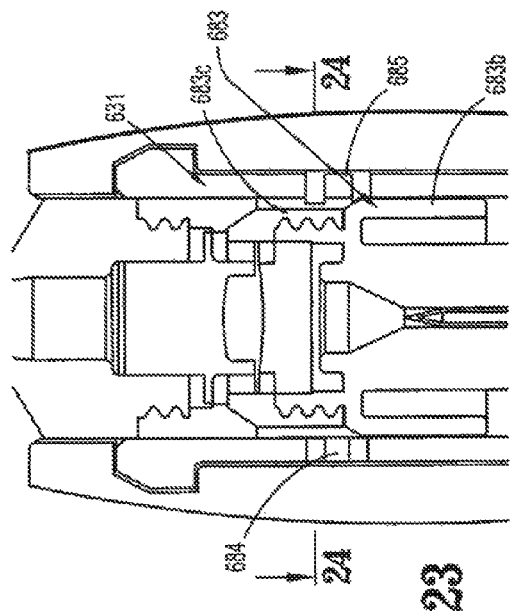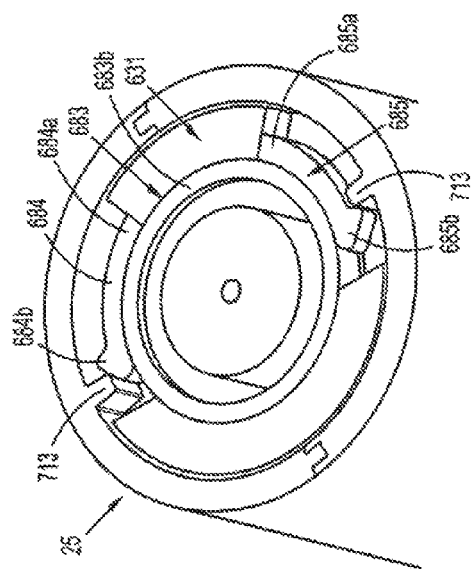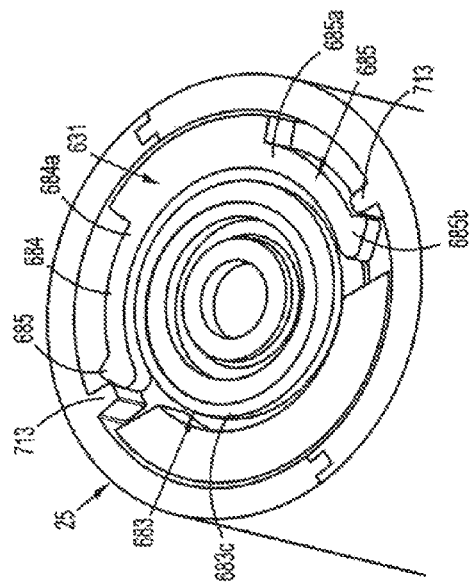

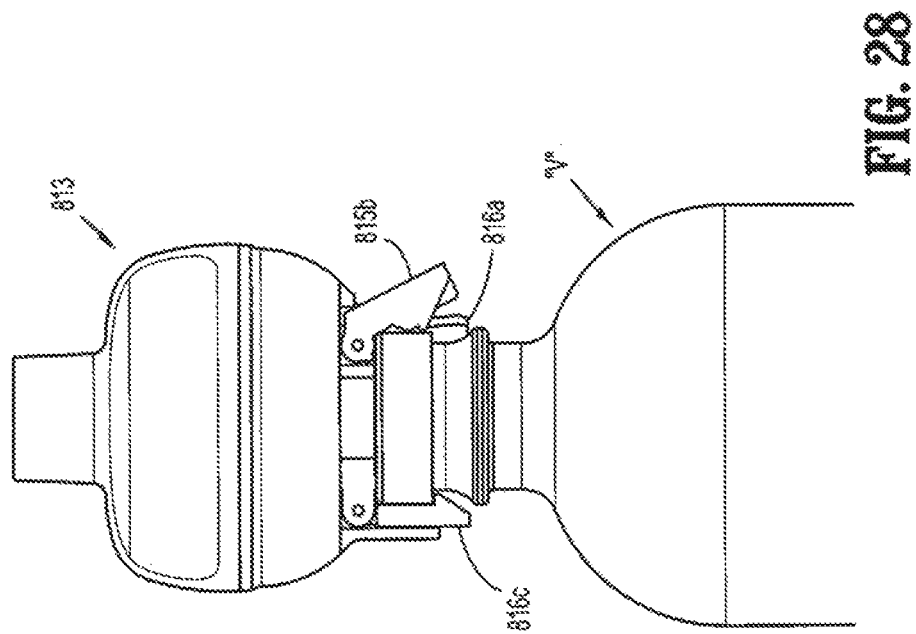
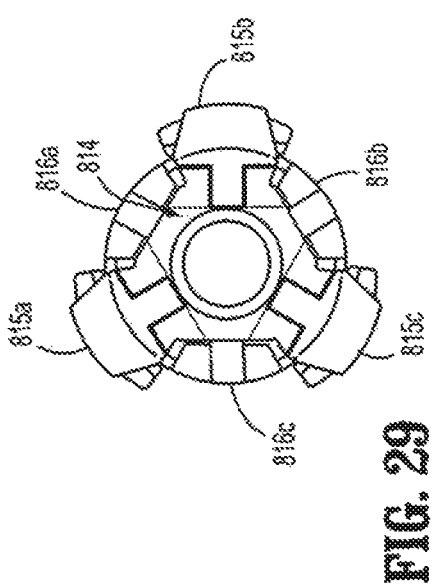
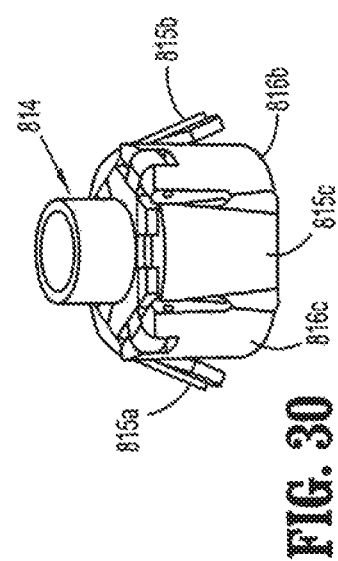

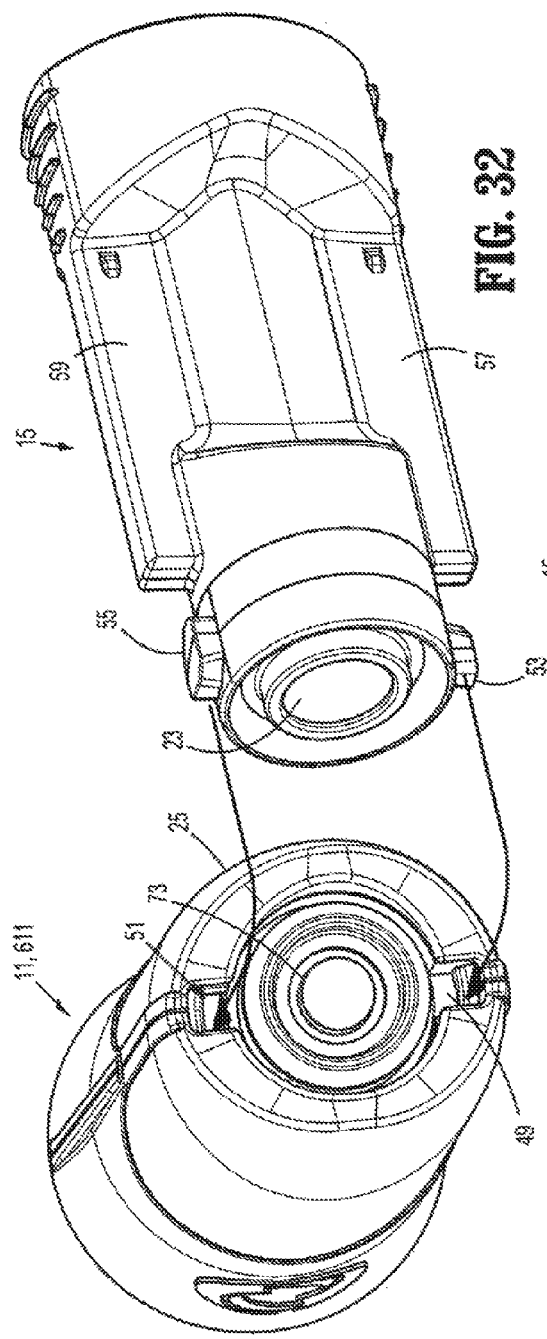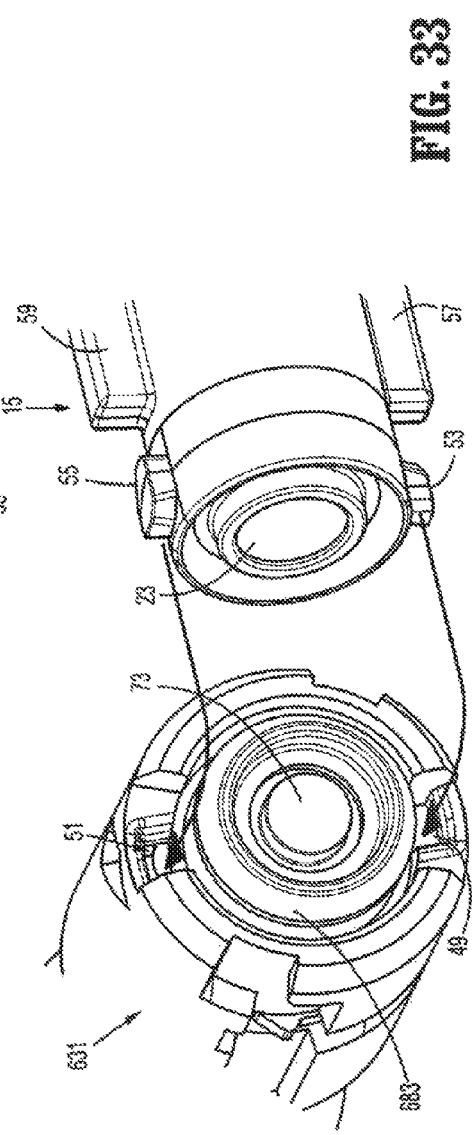

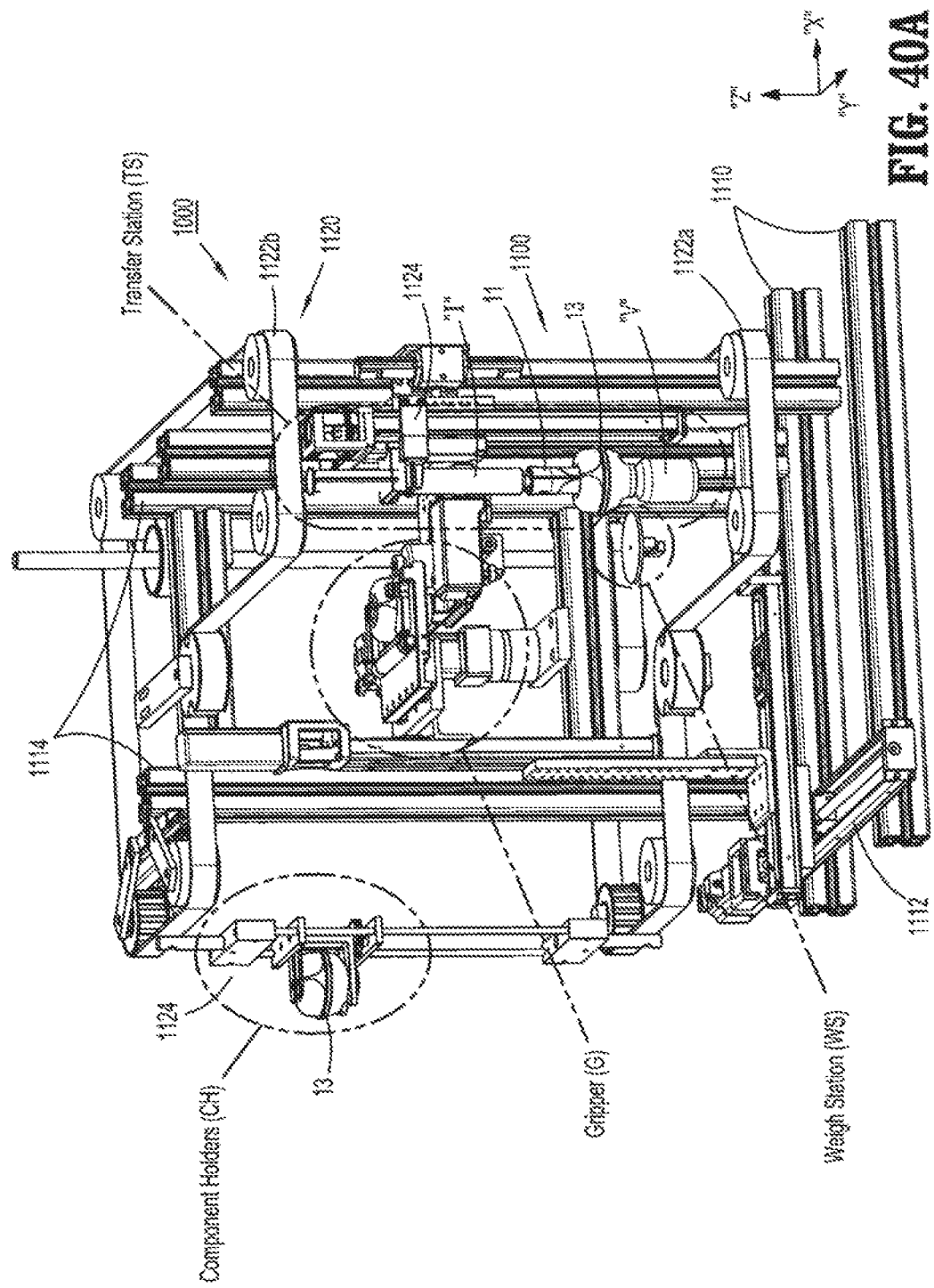

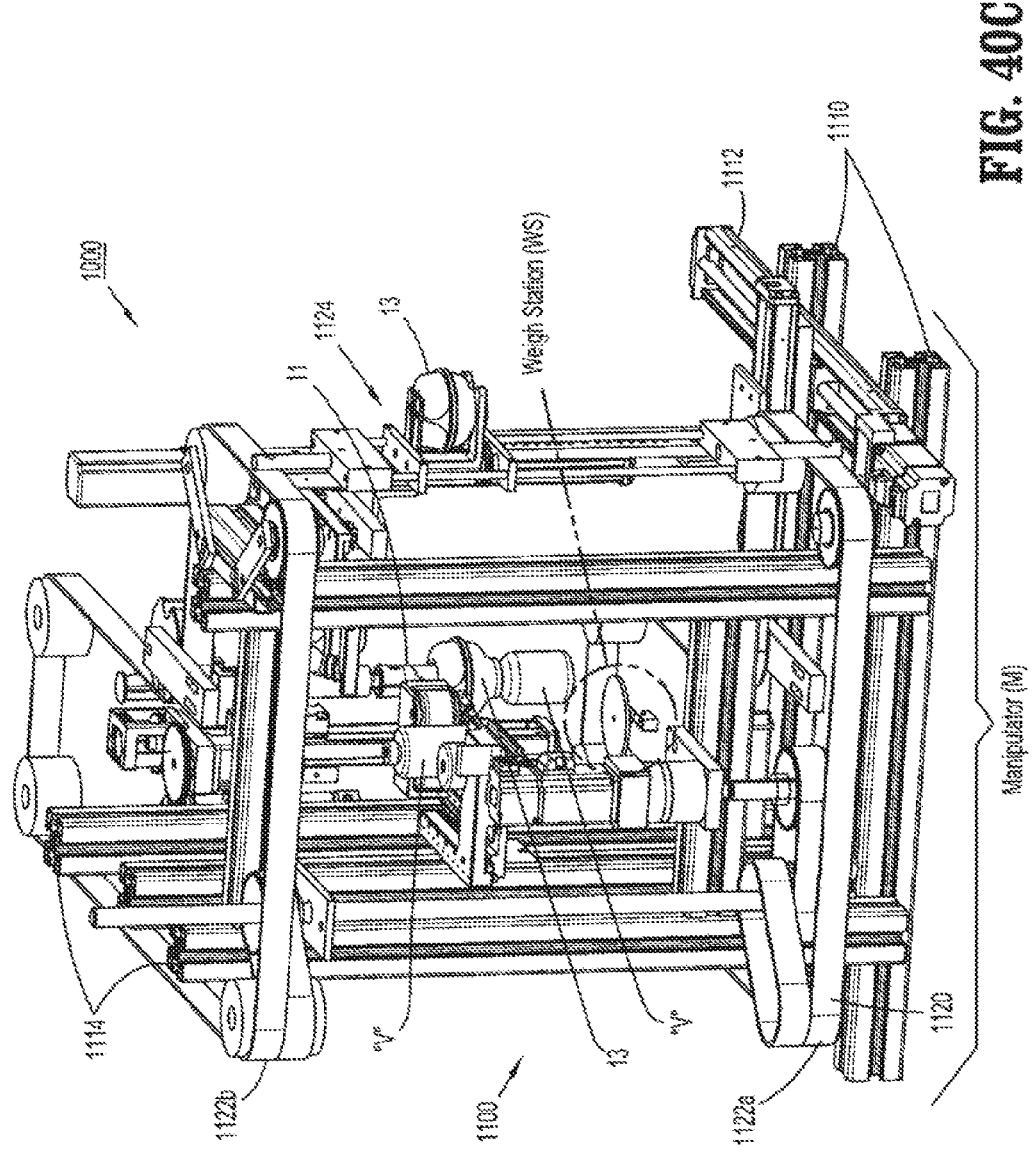

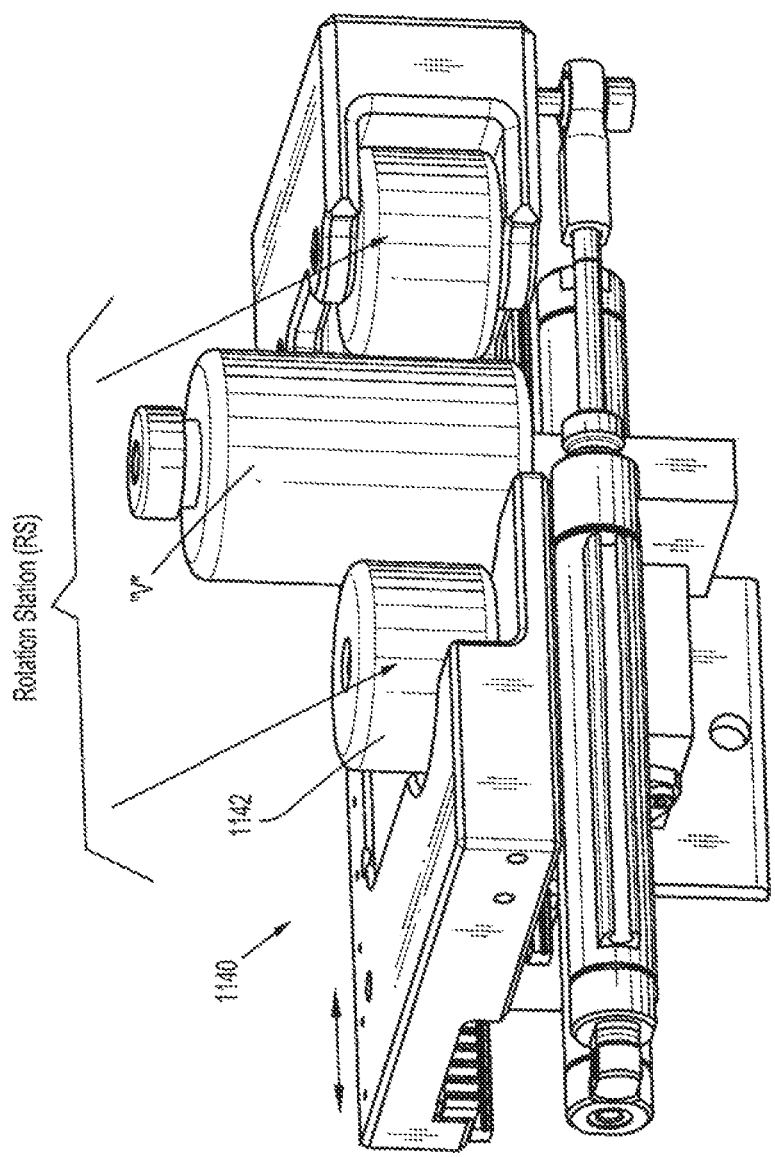

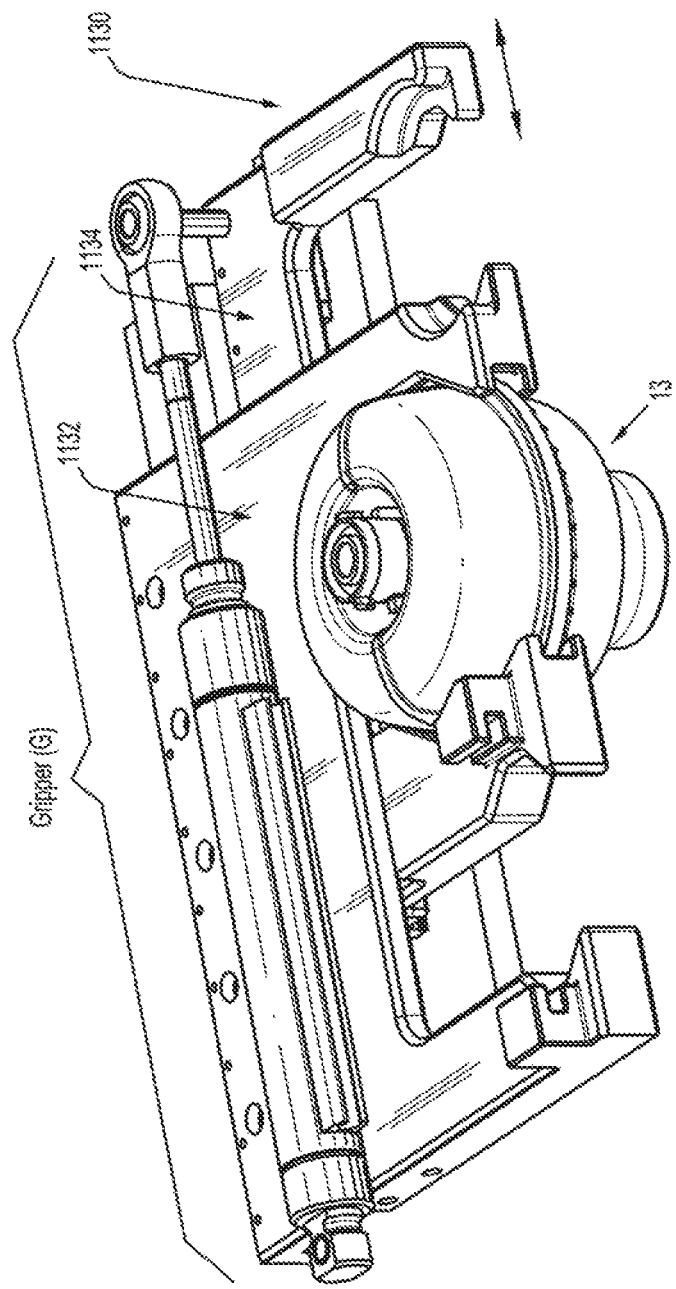

COMPOUNDING SYSTEMS AND METHODS FOR SAFE MEDICAMENT TRANSPORT

CROSS-REFERENCE TO RELATED APPLICATIONS

The present application is a 35 U.S.C. § 371 National Phase Filing claiming the benefit of and priority to International Application No. PCT/US2014/049609, filed on Aug. 4, 2014, which claims the benefit of and priority to each of U.S. Provisional Application Ser. No. 61/984,144, filed on Apr. 25, 2014; and U.S. Provisional Application Ser. No. 61/861,680, filed on Aug. 2, 2013; the entire content of each of which being incorporated herein by reference.

BACKGROUND

1. Technical Field

The present application relates to systems and methods for the safe transportation of medicaments and, more particularly, to systems and methods for the handling and transport of potentially hazardous medicaments, in particular, cytotoxic drugs and the like.

2. Background of Related Art

In one instance, hazardous medicines are frequently applied in the treatment of certain diseases, in particular, for example, in the treatment of cancer. Cytotoxic drugs have generally been used to kill cancer cells. However, the use of cytotoxic drugs, in the treatment of cancer cells, presents specific dangers to all cells, both in the patient and in healthcare providers. Although the exposure to a health care provider is normally very small for each cytotoxic drug dose administration, evidence suggests that chronic, low-dose exposure can produce significant health problems. Accordingly, a system that allows the safe handling of hazardous drugs while significantly reducing and/or eliminating the exposure to providers would be of great benefit.

Drugs are typically supplied in glass or plastic vials that are capped with a gas impermeable liquid seal or stopper. In some instances, the vial contents are a solid powder, such that a liquid needs to be injected for mixing (e.g., reconstitution). The injection of additional contents (e.g., liquid) into the vial produces an increased pressure which stresses the seal or stopper. Although the vial is intended to be sealed to liquid and gases, drug molecules in vapor phase can leak or pass around the sides of the stopper or through the stopper as the injection needle is withdrawn, thus presenting a hazard to the provider or clinician.

Accordingly, with the potential for aerosol leakage, leakage/spraying upon needle withdrawal, or spills, a means with which to prevent the accidental vapor phase drug egress is required. The provision of a pressure gradient/differential across the seals will ensure that any gas will flow from high to low pressure. Establishing a negative relative pressure between the inside of the transfer volume and atmosphere will prohibit the egress of vapor phase drug.

Thus, the need exists for new components and systems capable of transferring gases/fluids/liquids or other substances between a conventional syringe and one of a vial, a patient I.V. (intra-venous) set, or an I.V. bag without leaking or spilling and without exposure of the liquids to substances outside the closed system. As such, healthcare personnel may more safely use and handle fluid substances including potentially hazardous liquids and the like.

The hazardous medicines, including Cytotoxic drugs amongst others, are typically prepared by a technician in a clean room setting, or by a fully automated or robotic system. However, it is desirable to provide a system for the preparation of these hazardous medicines that is semi-automated or that is a user/technician assisted system, wherein some portion or steps in the preparation of these hazardous medicines is accomplished by the user/technician and some portion in the preparation of these hazardous medicines is accomplished by an apparatus or the like.

Additionally, these hazardous medicines must be prepared in a clean room setting or the like, such as, for example, in a room, under a hood, in a chamber, or the like. A clean room is a room in which the concentration of airborne particles is controlled to meet a specified airborne particulate cleanliness class. Clean rooms are classified by the cleanliness of their air. Accordingly, for the preparation of these hazardous medicines, it is required that the clean room have an ISO (International Standards Organization) class 5 rating.

Clean rooms are designed to maintain positive air pressure, preventing "unclean" (contaminated) air from flowing inside and less-clean air from flowing into clean areas. The idea is to ensure that filtered air always flows from cleanest to less-clean spaces.

ISO class 5 and cleaner facilities rely on unidirectional, or laminar, airflow. Laminar airflow means that filtered air is uniformly supplied in one direction (at a fixed velocity) in parallel streams, usually vertically. Air is generally re-circulated from the base of the walls of the clean room back up to the filtering system.

Thus, a critical factor in clean room design is controlling air-change per hour (ACH), also known as the air-change rate, or ACR. This refers to the number of times each hour that filtered outside air replaces the existing volume in a building or chamber.

Further, another critical factor in clean room design controlling or reducing the turbulence of the air flowing through the clean room, wherein lower turbulence will increase the cleanliness of the room.

In ISO class 5 clean rooms, the particle per cubic meter must be no more than 3520 particles/$m^3$ in a size of 0.5 micrometers or larger when counted at representative locations normally not more than 1 foot away from the work site, within the airflow, and during filling/closing operations.

Accordingly, improvements in systems for the handling and transport of potentially hazardous medicines, in particular, cytotoxic drugs and the like, in a clean room or chamber, is desired and warranted.

SUMMARY

The present application relates to systems and methods for the handling and transport of potentially hazardous medicines, in particular, cytotoxic drugs and the like.

According to an aspect of the present disclosure, an automatic or semi-automatic preparation system for forming a medicament solution from a vial containing one of a liquid and a non-liquid material, is provided. The preparation system includes a carousel configured to provide three axes of motion. The carousel includes a manipulator having at least one first rail defining a first axis; at least one second rail defining a second axis, the second axis being oriented orthogonal to the first axis; at least one third rail defining a third axis, the third axis being oriented orthogonal to the each of the first axis and the second axis; a first gear belt movably supported on at least one of the first rails, the second rails or the third rails, wherein the first gear belt, the first gear belt is movably supported on a series of sprockets; and a second gear belt movably supported on at least one of the first rails, the second rails or the third rails, wherein the second gear belt, the first gear belt is movably supported on a series of sprockets; the first gear belt and the second gear belt being spaced apart from one another and being arranged in parallel with one another.

The carousel further includes at least one component holder supported on at least one of the first gearbelt and the second gear belt, each component holder being configured to selectively hold a syringe, a vial, a syringe adapter or a vial adapter; and at least one of a rotation station, a transfer station, and a weigh station disposed about the carousel.

The rotation station is configured for inverting and reverting a syringe and vial assembly. The transfer station is configured for transferring material from a vial to a syringe. The weigh station is configured for weighing at least one of the syringe, the vial, and the syringe and vial assembly.

The first gearbelt may be movable in a first plane defined by the first axis that is defined by the first rail and the second axis that is defined by the second rail. The second gearbelt may be movable in a second plane defined by the first axis that is defined by the first rail and the second axis that is defined by the second rail. The second plane may be parallel to the first plane and may be spaced a distance therefrom.

At least one component holder may be movable along the third axis, between the first plane and the second plane.

The preparation system may further include at least one syringe adapter manipulatable by a component holder of the carousel. Each syringe adapter includes a body portion defining a lumen therethrough; and a seal member connected to a distal end of the body portion and extending across the lumen thereof; and at least one vial adapter connectable to a neck of a vial and configured to receive the body portion of the syringe adapter.

The vial adapter may include a base having at least one retainer configured to engage the neck of the vial, with the base defining an opening having a seal member disposed therewithin. The vial adapter includes a stem extending from the base, with the stem defining a lumen therethrough and being in operative communication with the opening of the base, and with the stem defining an opening through a wall thereof.

The vial adapter may include a needle shuttle valve slidably disposed within the lumen of the stem, with the needle shuttle valve forming a fluid tight seal with the stem, and with the needle shuttle valve supporting a transfer needle such that the transfer needle extends from a first and a second end thereof and supporting a vacuum needle such that the vacuum needle extends from the first end of the needle shuttle valve.

The vial adapter may include a vacuum cup slidably supported on the stem, with the vacuum cup being in fluid tight contact with the stem and with the base. A vacuum chamber may be defined in the space between the base, the stem and the vacuum cup. The vacuum chamber may be in fluid communication with the lumen of the stem through the opening formed in the wall of the stem.

The preparation system may further include a transfer station having a first condition in which the needle shuttle valve of the vial adapter is in a retracted position such that the transfer needle and the vacuum needle do not extend through the seal member of the base of the vial adapter. The vacuum cup may be in an advanced position such that the volume of the vacuum chamber is at a minimum.

The transfer station may have a second condition in which the body portion of the syringe adapter is advanced through the lumen of the stem such that the second end of the transfer needle penetrates through the seal member of the body portion and the needle shuttle valve is advanced through the lumen of the stem to penetrate the first end of the transfer needle and a tip of the vacuum needle through the seal member of the vial adapter. The vacuum needle may be brought into fluid communication with the opening formed in the wall of the stem.

The transfer station may have a third condition in which the vacuum cup is moved to a proximal position thereby enlarging the vacuum chamber and drawing a vacuum through the vacuum needle.

The carousel may be configured to connect a syringe adapter to a syringe, and to transport the assembled syringe and syringe adapter to a vial having a vial adapter connected thereto. The carousel may be configured to connect the syringe adapter, that is connected to the syringe, to the vial adapter, that is connected to the vial.

A component holder of the preparation system may include a gripper having a first pair of fixed, spaced apart jaws, the first pair of jaws including a first jaw and a second jaw; and a second pair of fixed, spaced apart jaws, the second pair of jaws including a first jaw and a second jaw. The first pair of jaws may be translatable relative to the second pair of jaws; and the first jaw of the first pair of jaws may be interposed between the second pair of jaws, and the second jaw of the second pair of jaws may be interposed between the first pair of jaws.

Operation of the gripper may include translation of the first pair of jaws relative to the second pair of jaws to grip a component at (1) a first gripping position located between the first jaw of the first pair of jaws and the first jaw of the second pair of jaws; (2) a second gripping position located between the second jaw of the first pair of jaws and the first jaw of the second pair of jaws; and (3) a third gripping position located between the second jaw of the first pair of jaws and the second jaw of the second pair of jaws.

The first pair of jaws may support a rack, and the second pair of jaws may support a rack, and wherein a pinion may interconnect the each rack. In use, rotation of the pinion may result in axial translation of the first pair of jaws and the second pair of jaws relative to one another.

The preparation system may further include an error trapping protocol to check and confirm that correct components are being manipulated about the carousel relative to one another. In use, for a particular stage in the process, the error trapping protocol may compare a known dimension of a component expected in the gripper against a real-time dimension of a components gripped within the gripper, and may trigger an alert when a known expected dimension for the component is different than a real-time measured dimension of the component that is present in the gripper.

According to another aspect of the present disclosure, a component holder for an automatic or semi-automatic preparation system for forming a medicament solution from a vial containing one of a liquid and a non-liquid material, is provided. The component holder includes a gripper having a first pair of fixed, spaced apart jaws, the first pair of jaws including a first jaw and a second jaw; and a second pair of fixed, spaced apart jaws, the second pair of jaws including a first jaw and a second jaw. The first pair of jaws is translatable relative to the second pair of jaws; and the first jaw of the first pair of jaws is interposed between the second pair of jaws, and the second jaw of the second pair of jaws is interposed between the first pair of jaws.

Operation of the gripper may include translation of the first pair of jaws relative to the second pair of jaws to grip a component at (1) a first gripping position located between the first jaw of the first pair of jaws and the first jaw of the second pair of jaws; (2) a second gripping position located between the second jaw of the first pair of jaws and the first jaw of the second pair of jaws; and (3) a third gripping position located between the second jaw of the first pair of jaws and the second jaw of the second pair of jaws.

The first pair of jaws may support a rack, and the second pair of jaws may support a rack, and wherein a pinion may interconnect the each rack. In use, rotation of the pinion results in axial translation of the first pair of jaws and the second pair of jaws relative to one another.

According to still another aspect of the present disclosure, a process of operating an automatic or semi-automatic preparation system for forming a medicament solution from a vial containing one of a liquid and a non-liquid material, is provided. The process includes loading a preselected vial, containing a quantity of a medicament, into a component holder of the preparation system; loading a vial adapter into a component holder of the preparation system; loading a syringe into a component holder of the preparation system; loading a syringe adapter into a component holder of the preparation system; and performing a medicament extraction process; and disengaging the syringe adapter from the vial adapter.

The medicament extraction process includes approximating the vial and the vial adapter; mechanically and fluidly coupling the vial and the vial adapter to form an assembly; approximating the syringe and the syringe adapter; mechanically and fluidly coupling the syringe and the syringe adapter to form an assembly; then, moving the syringe adapter into engagement with the vial adapter, wherein a seal of the syringe adapter makes connection with a seal of the vial adapter; and advancing the syringe adapter toward the vial adapter until a stopper of the vial is engaged by the seal of the vial adapter.

The medicament extraction process further includes withdrawing a plunger of the syringe relative to a barrel of the syringe to begin withdrawing a fluid from the vial; advancing the plunger of the syringe relative to the barrel of the syringe to inject fluid back into the vial; and withdrawing the plunger of the syringe relative to the barrel of the syringe to withdraw the fluid from the vial to complete a transfer of a medicament from the vial to the syringe.

The process may further include connecting the syringe containing the medicament to a container, and injecting the medicament into the container.

The process may further include reconstituting a lyopholized medicament contained in the vial. The reconstituting step may include injecting a diluent into the vial containing the lyopholized medicament; and agitating the vial containing the lyopholized medicament to dissolve the lyopholized medicament.

The reconstituting step may occur after the vial adapter is connected to the syringe adapter.

The reconstituting step may include inverting the syringe, the syringe adapter, the vial adapter and the vial after the vial adapter is connected to the syringe adapter.

The process may further include weighing the vial prior to the reconstituting step; and weighing the vial after the reconstituting step.

The invention will be explained in greater detail below in descriptions of preferred embodiments and referring to the attached figures.

BRIEF DESCRIPTION OF THE DRAWINGS

In the following, the preferred embodiments of invention will be described in detail with reference to the following attached figures:

FIG. 19 is a further side, elevational view of a distal end of the syringe adapter of FIG. 17;

FIG. 20 is a longitudinal, cross-sectional view of a distal end of the syringe adapter of FIGS. 17-19;

FIG. 21 is a further, longitudinal, cross-sectional view of a distal end of the syringe adapter of FIGS. 17-19, illustrating a locking system of the syringe adapter in a first condition;

FIG. 22 is a cross-sectional view of the syringe adapter of FIG. 21, as taken through 22-22 of FIG. 21;

FIG. 23 is a further, longitudinal, cross-sectional view of a distal end of the syringe adapter of FIGS. 17-19, illustrating a locking system of the syringe adapter in a second condition;

FIG. 24 is a cross-sectional view of the syringe adapter of FIG. 23, as taken through 24-24 of FIG. 22;

FIG. 28 is a schematic, elevational view of the universal vial adapter of FIG. 25, shown connected to a vial neck having a second diameter;

FIG. 29 is a top, plan view of a hub of the universal vial adapter as connected to the vial of FIG. 28;

FIG. 30 is a perspective view of the hub of the universal vial adapter as connected to the vial of FIG. 28;

FIGS. 32-38 illustrate a sequence of fluidly connecting a syringe adapter and a patient push adapter;

FIGS. 40A-40G are schematic, perspective views of the preparation system 1000, and sub-systems thereof, in accordance with the present disclosure;

DETAILED DESCRIPTION

Figure 1:
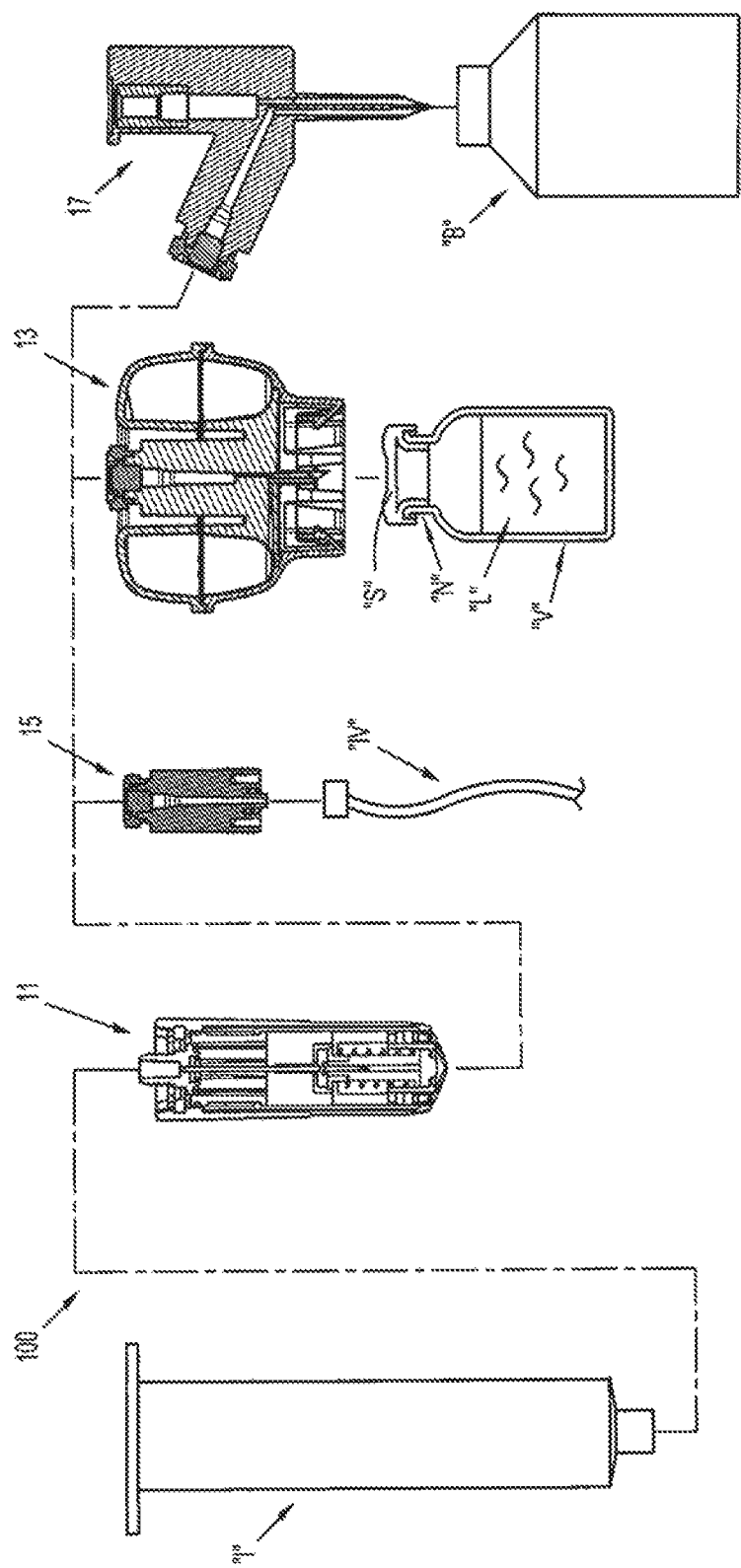
FIG. 1 is a schematic illustration of a closed fluid transfer system of the present disclosure illustrating a fluid connectability of a syringe to an I.V. Set, a vial and an I.V. bag via combination of a syringe adapter and one of an I.V. set adapter, a vial adapter and an I.V. bag adapter.
Figure 2:
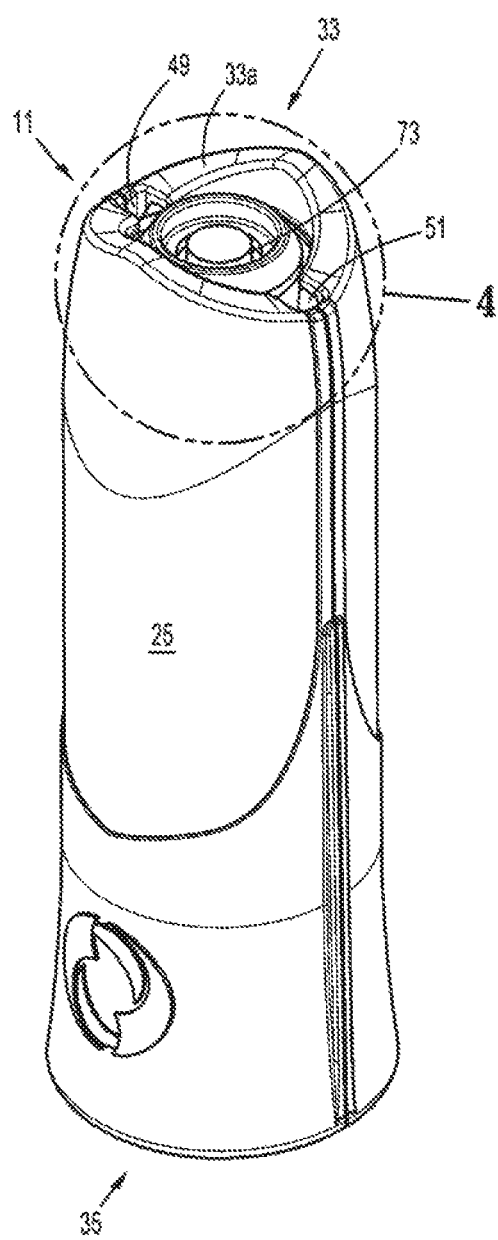
FIG. 2 is a perspective view of a syringe adapter of the closed fluid transfer system of FIG. 1.

The closed fluid transfer system, in accordance with the present disclosure, is generally designated as 100 and generally includes a module/adapter that fluidly connects to a syringe or any male luer lock connection point; a patient push module/adapter that fluidly connects directly to an I.V. line; at least a module/adapter that fluidly connects to a vial/container storing/containing a fluid/liquid in the form of a hazardous drug and the like; and a module/adapter that fluidly connects to an I.V. bag. Each of the above-mentioned modules/adapters will be described in greater detail below with reference to the accompanying figures, wherein like numbers identify like elements.

In accordance with the present disclosure, the system is a "closed" fluid-transfer system capable of transferring liquids between a conventional syringe and one of a patient I.V. set, a vial, or an I.V. bag without leaking or spilling and without exposure of the gases/fluids/liquids or other substances to a location or a substance outside the closed system. One purpose of the closed fluid transfer system is to permit health care personnel to safely use and handle liquid-form medicine, including potentially hazardous liquid drugs and/or the like.

In accordance with the present disclosure, and as will be discussed in greater detail below, the closed fluid transfer system 100 includes a syringe adapter 11 (see FIGS. 1-7) that is structured to provide a closed fluid connection between a first fluid container in the form of a conventional needleless syringe "I" and a second fluid container/conduit in the form of a patient I.V. set, a vial "V", or an I.V. bag. The fluid transfer is accomplished by first connecting one of a patient push adapter 15 (see FIGS. 1 and 11-14) to an I.V. set, a vial adapter 13 (see FIGS. 1 and 8-10) to a vial, or an I.V. bag adapter 17 (see FIGS. 1 and 15-16) to an I.V. bag, as necessary. Each adapter 13, 15, 17 is provided with an identical male stem 19 which defines an internal lumen 21 closed at one end by a resilient seal 23. The syringe adapter 11 is mated to the male stem 19, thereby permitting fluid flow from or to the syringe "I", as described in more detail herein.

Referring now specifically to FIGS. 1-7, the closed fluid transfer system 100 includes a syringe adapter 11. Syringe adapter 11 is a type of valve which can be in an open state to permit fluid flow therethrough or in a closed state to prevent fluid flow. The open and closed states occur in a specific sequence dictated by the syringe adapter 11 architecture as described herein.

The syringe adapter 11 consists of four main parts which are a housing 25, a conventional hollow metal needle 27, a shuttle 29, and a collar 31. The housing 25 is generally cylindrical in shape having a distal end 33 and a proximal end 35, a longitudinal axis 37, a distal opening 39, and a female cavity 41 into which the male stem 19 is received. Housing 25 may be formed to have two housing side portions or halves 43, 45 and a housing base portion 47 which fits partially between the side portions 43, 45. Side portions 43, 45 define opposed slots 49, 51 (see FIGS. 2 and 4) which begin at housing distal end 33 and extend within housing 25. Slots 49, 51 which receive a respective guide pin 53, 55 and guide surface 57, 59 of any male stem 19, which are each keyed to a respective one of the slots 49, 51 (or a respective one of slots 51, 49), for the purposes described in full detail below.

Figure 3:
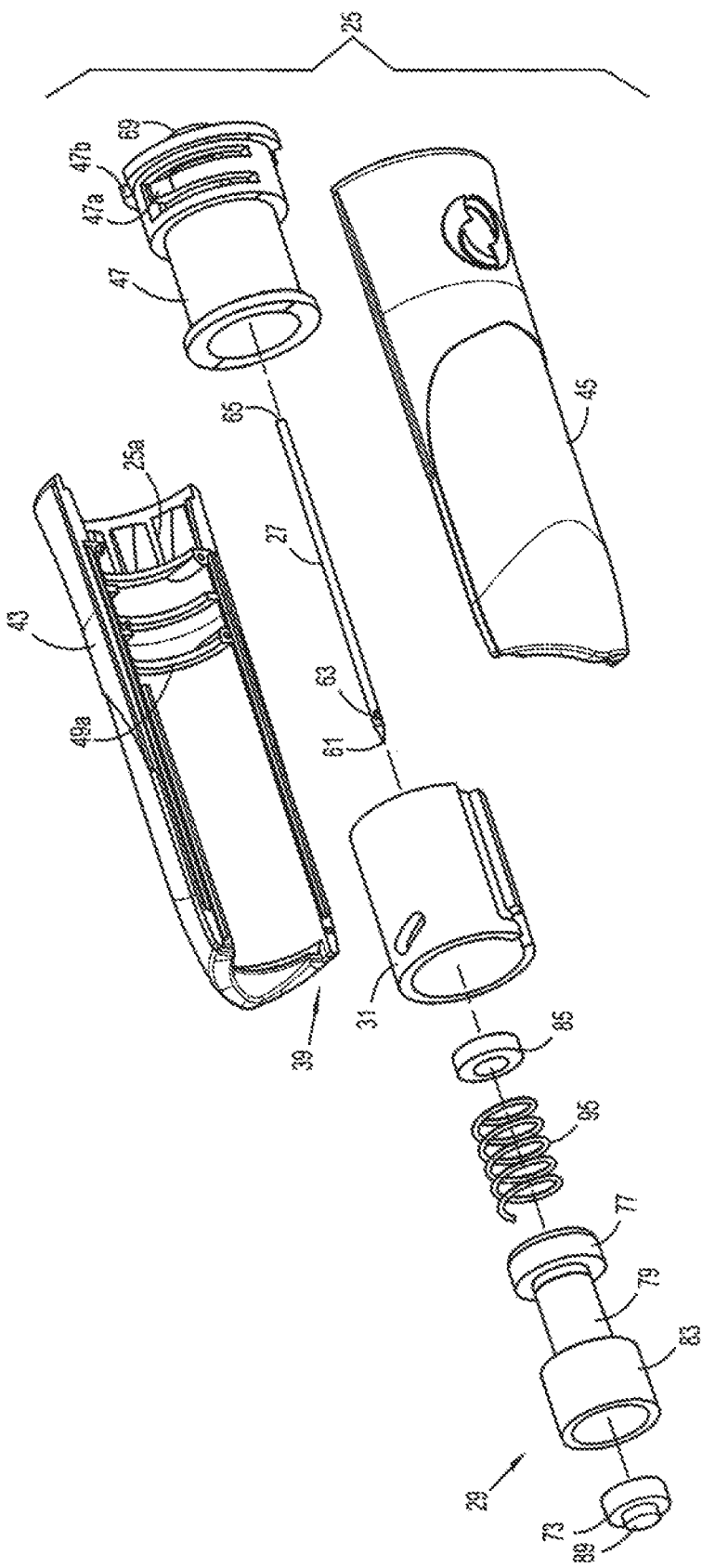
FIG. 3 is a perspective view, with parts separated, of the syringe adapter of FIG. 2.
Figure 4:
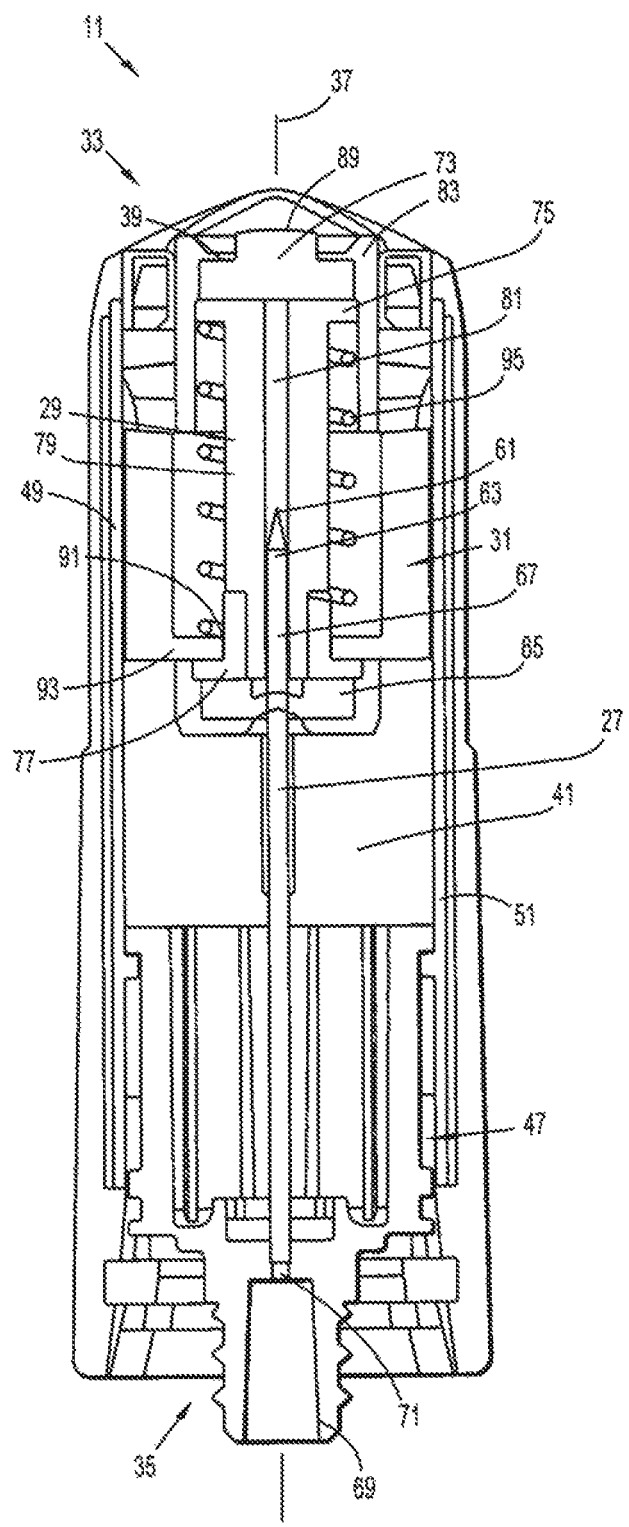
FIG. 4 is a longitudinal, cross-sectional view of the syringe adapter of FIGS. 2 and 3.

Hollow metal needle 27, as seen in FIGS. 3 and 4, is a conventional needle with a sharpened tip 61, a tip end opening 63, a proximal end opening 65, and a lumen 67 permitting fluid flow through the conventional needle 27 between the needle openings 63, 65. It is envisioned that needle 27 will be a conventional 18 gauge steel "pencil tip" needle commercially available (18 gauge refers to the outer diameter of needle 27). The conventional pencil tip needle 27 has an extremely sharp tip 61 with opening 63 spaced slightly away from the sharpened tip 61. The pencil tip needle 27 is of a type and size conventionally used with syringes to penetrate patient blood vessels for delivery or extraction of fluids.

Needle 27 is mounted within housing 25, in fixed-positional relationship, on an inner side of base 47 with tip 61 of needle 27 pointing/extending toward distal end 33 of housing 25. An advantage of this design is that needle 27, and specifically, the extremely sharp needle tip 61 of needle 27, are fully enclosed within the housing 25 and are completely shielded from contact with a user. In this manner, the possibility of injuries as a result of user needle-stick, has been significantly reduced and/or eliminated.

Housing base 47 is rotatably supported in housing 25. Housing base 47 includes an outer side with a conventional luer connector 69 provided to accept the delivery end of a conventional needless syringe. A lumen 71 extends through base 47 between luer connector 69 and proximal opening 65 of needle 27 permitting fluid flow between the needle tip opening 63 and the luer connector 69.

Housing 25 and housing base 47 of syringe adapter 11 cooperate with one another to provide a ratchet mechanism by which syringe adapter 11 may not be accidentally or inadvertently disconnected from syringe "I". In particular, the ratchet mechanism includes, as seen in FIG. 3, a plurality of ribs 25a formed on an inner surface of housing 25 and at least one resilient finger 47a supported on housing base 47, whereby housing base 47 is held in a fixed position relative to housing 25 when syringe adapter 11 is connected to syringe 11 and to is free to rotate relative to housing 25 if syringe adapter 11 is being inadvertently or accidentally disconnected from syringe "I". In this manner, the closed system between the syringe adapter 11 and syringe 11 is better maintained.

Generally, in operation, when syringe adapter 11 is connected to syringe "I", the at least one resilient finger 47*a* of housing base 47 engages ribs 25*a* of housing in such a manner that rotation of housing base 47 relative to housing 25 is inhibited and syringe adapter 11 may be securely connected to syringe "I". Further, if there is an inadvertent or accidental rotation of syringe adapter 11 relative to syringe "I", tending to disconnect syringe adapter 11 from syringe "I", and thus destroy the closed system, each resilient finger 47*a* is configured to slip over and across ribs 25*a* of housing 25, allowing housing base 47 to rotate relative to housing 25 and thus maintain the closed system.

If it is desired to intentionally disconnect syringe "I" from syringe adapter 11, a user may squeeze housing 25 radially inward, in the proximity of luer connector 69, to engage at least one tooth (not shown) formed on an inner surface of housing 25 with a respective notch 47*b* formed in an outer surface of housing base 47. Then, with the at least one tooth (not shown) of housing 25 engaged with the respective notch 47*b* of housing base 47, the user may rotate syringe adapter 11 relative to syringe "I" to disconnect syringe "I" from luer connector 69 of housing base 47.

Shuttle 29 is provided for at least the following important purposes. First, shuttle 29 supports shuttle distal seal 73 across distal opening 39 of housing 25 to close cavity 41 of housing 25 so that contaminants cannot enter the housing 25 when the syringe adapter 11 is not mated to one of the adapters 13, 15, 17. Second, the shuttle 29 supports shuttle distal seal 73 at a position across distal opening 39 of housing 25 so that distal seal 73 can be easily swabbed with alcohol before use to ensure that the seal 73 is sterile. In accordance with the present disclosure, and as is customary, a seal 23 of any male stem 19 (as seen in for example FIG. 8 and as will be described in greater detail below) is also swabbed with alcohol or other microbial agent before being mated to the syringe adapter 11, so as to ensure sterility of the abutment between seals 23 and 73. Finally, the shuttle 29 provides a fluid-tight enclosure for needle 27 to prevent fluid flow outside of syringe adapter 11 when in the closed state.

As illustrated in FIGS. 3 and 4, shuttle 29 includes distal and proximal annular flanges 75, 77, respectively, and an intermediate body portion 79 between flanges 75, 77 defining a shuttle lumen 81 therethrough. Distal flange 75 supports a distal seal 73 and a barrel 83, seated on distal flange 75, holds distal seal 73 on distal flange 75. Shuttle proximal flange 77 supports a proximal seal 85.

As illustrated in FIGS. 3 and 4, tip 61 of needle 27 extends into shuttle lumen 81 and proximal seal 85 forms a fluid-tight seal around needle 27. In the closed state, when syringe adapter 11 is fluidly connected to syringe "I", needle tip 61 and opening 63 are within shuttle lumen 81 and seals 73, 85 prevent fluid from exiting shuttle lumen 81.

Each seal 23, 73 is generally disk shaped and includes a respective outward projection 87, 89 (i.e., convex surface) which abut one another when the seals 23, 73 are held together, as described later herein. Seals 23, 73 and 85 are made of polyisoprene and seals 23 and 73 are designed want to retain or return to their original convex profile when in abutment with one another. Put another way, since seals 23, 73 are fabricated from a resilient material and tend to want to retain or return to their original convex profile, when seals 23, 73 are in abutment with one another, a substantially continuous interface between seals 23, 73 is established and maintained. While it is preferred that seals 23 and 73 be made from polyisoprene, it is contemplated and within the scope of the present disclosure, that seals 23, 73 may be made from thermoplastic elastomers (TPE), silicone, more specifically, HaloButyl-Polyisoprene, Chlorobutyl, thermoplastic vulcanizates (TPVs), any other resilient polymer, or any combinations thereof.

Intermediate portion 79 of shuttle 29 rides in collar opening 91 in collar end wall 93 of collar 31 for axial movement along axis 37 within housing 25. Barrel 83 is generally cylindrical in shape and has an outside diameter slightly less than an inside diameter of collar 31 to permit barrel 83 and shuttle 29 to reciprocate inside collar 31.

A spring 95 is provided and bears against end wall 93 of collar 31 and distal flange 75, partially within barrel 83. Spring 95 biases shuttle 29 toward distal end 33 of housing 25 so that distal seal 73 of shuttle 29 covers or extends across opening 39 of housing 25, for the reasons previously described. Spring-biased contact between barrel 83 and end wall 93 of collar 31 limits inward movement of shuttle 29 toward proximal end 35 of housing 25, and contact between proximal flange 77 of shuttle 29 and end wall 93 of collar 31 limits outward movement of shuttle 29 toward distal end 33 of housing 25.

Distal seal 73 of shuttle 29 does not contact the housing 25 and is supported solely by shuttle 29 and travels within collar 31 spaced from housing 25. Shuttle 29 is pushed axially toward proximal end 35 of housing 25 when contacted by seal 23 of any male stem 19 during use, as described more fully below.

Figure 8:
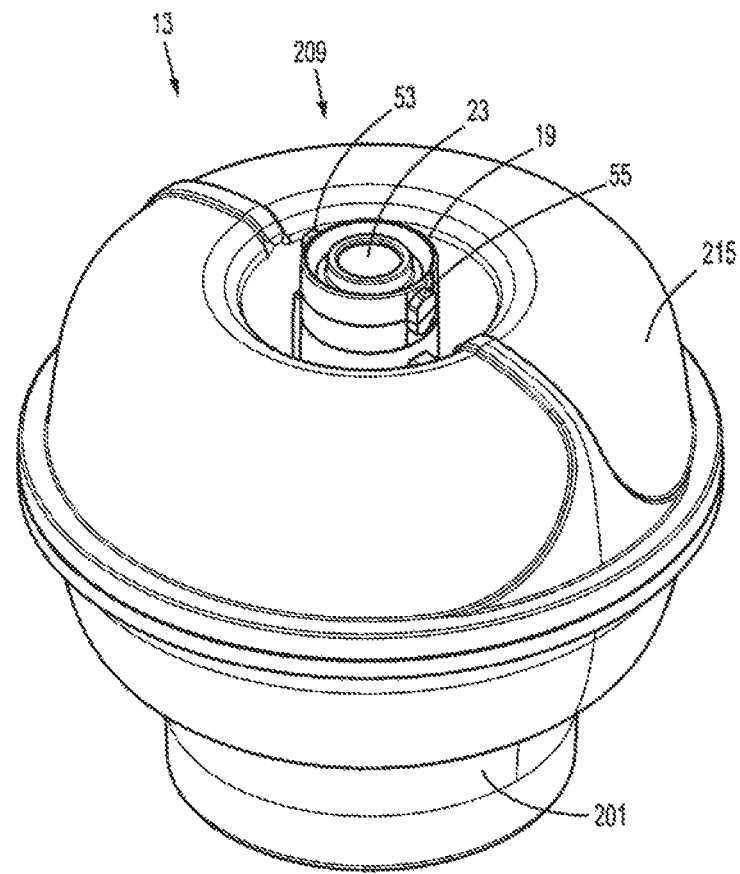
FIG. 8 is a perspective view of a vial adapter of the closed fluid transfer system of FIG. 1.

With continued reference to FIGS. 2-7, collar 31 and housing 25 cooperate to hold male stem 19 and seal 23 (for example, as seen in FIG. 8) thereof in abutment with distal seal 73 of shuttle 29 so that the abutting seals 23, 73 can subsequently be pierced by needle tip 61 of needle 27 and so that needle 27 can enter lumen 21 of male stem 19 to open the fluid path through syringe adapter 11. The abutment between seals 23, 73 established that distal seal 73 of shuttle 29 is the closure for distal opening 39 of housing 25 and also places distal seal 73 of shuttle 29 in a position convenient for swabbing with alcohol before use. The abutment between seals 23, 73 ensures that the two seals 23, 73 function as one and can be pierced together by needle 27. If the seals 23, 73 were to separate with needle tip opening 63 extended outside of lumen 81 of shuttle 29, liquids could leak into cavity 41 of housing 25, which is contrary to the purpose of providing a closed system.

Figure 5:
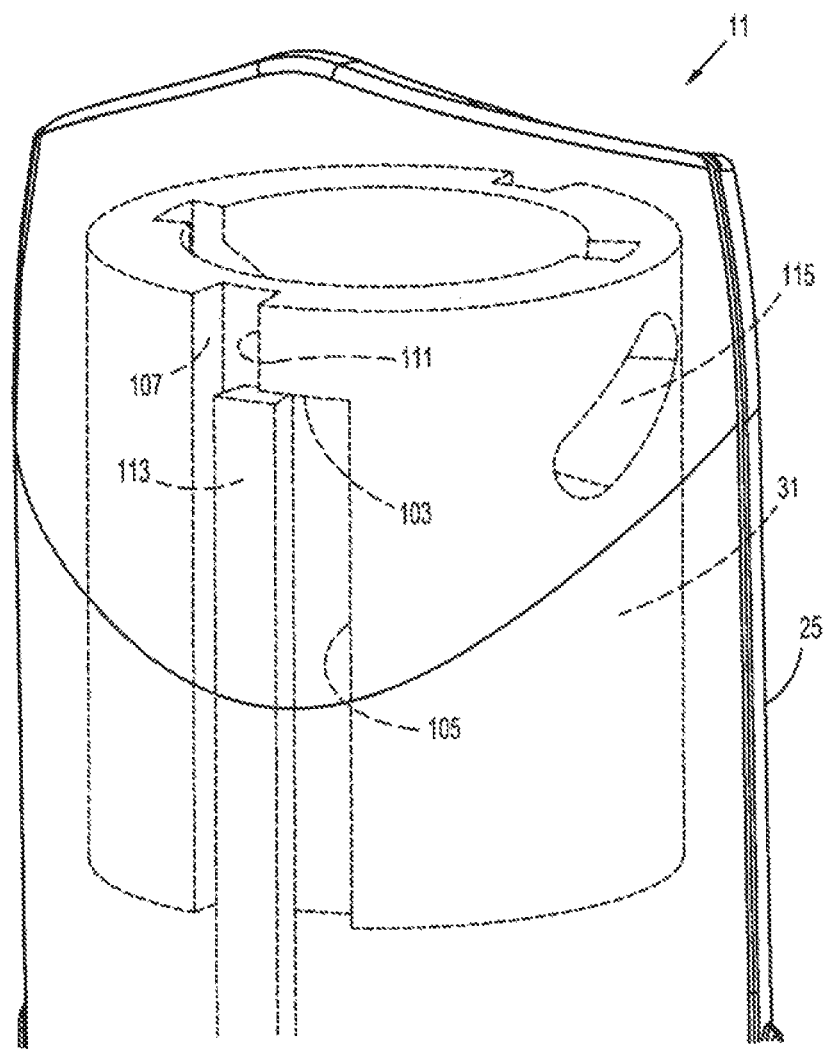
FIG. 5 is an enlarged view, of the indicated area of detail of FIG. 2, with the outer side portions shown in phantom.
Figure 6:
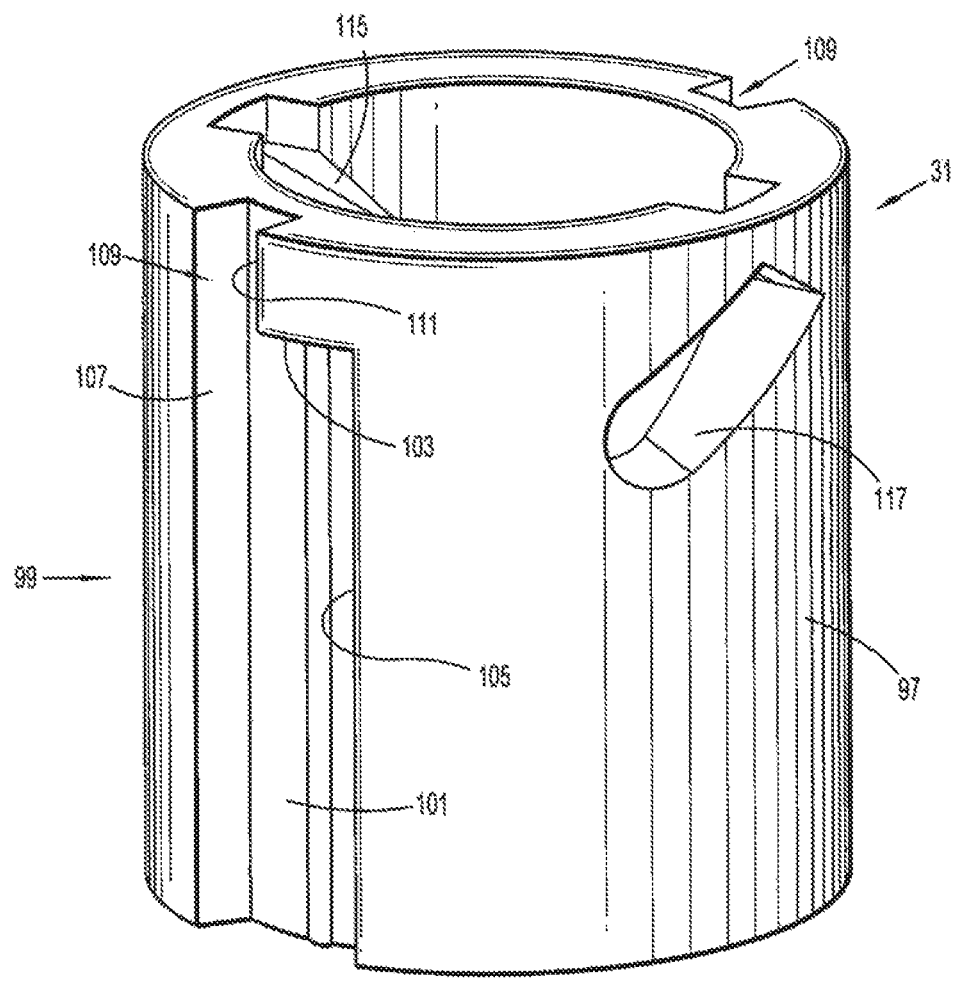
FIG. 6 is a top, perspective view of a collar of the syringe adapter of FIGS. 1-5.
Figure 7:
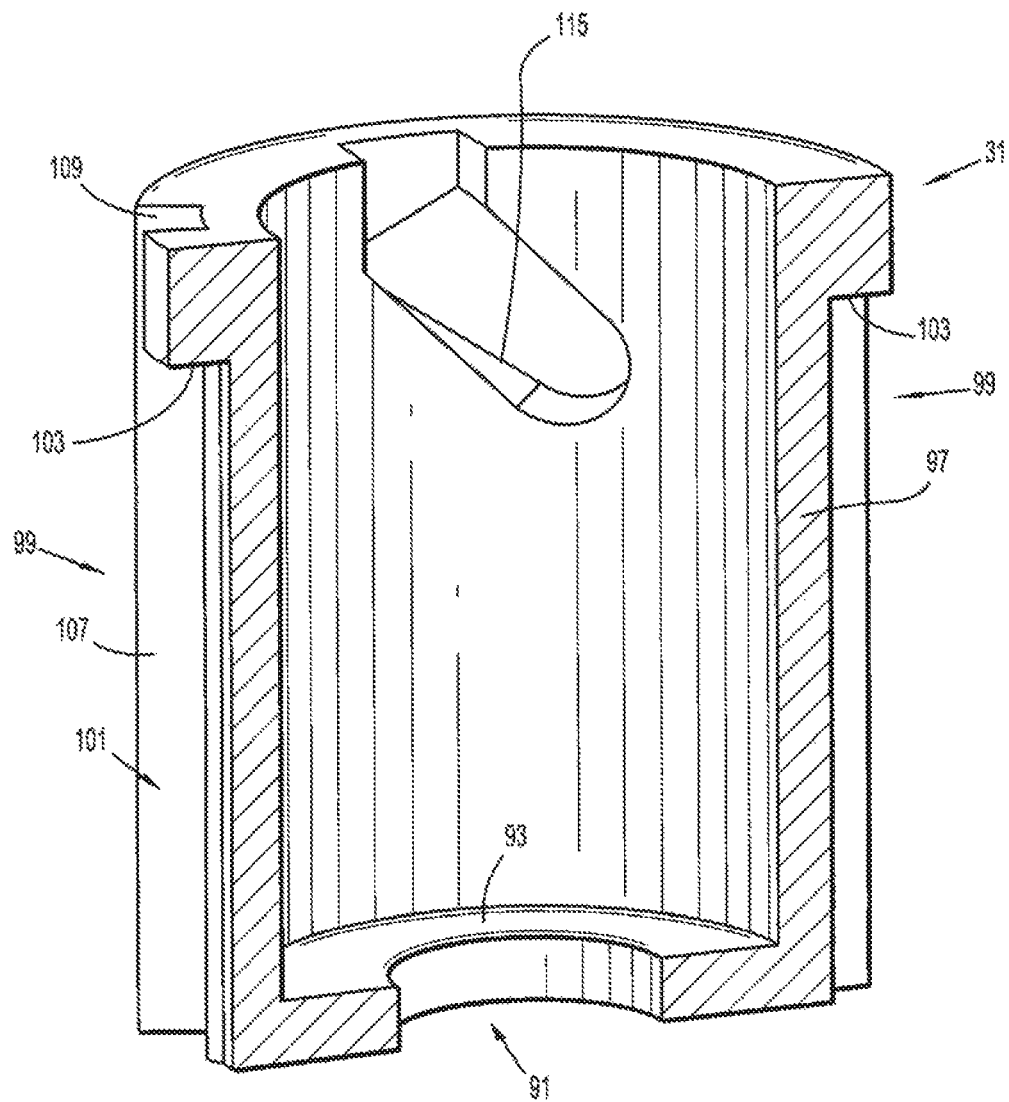
FIG. 7 is a longitudinal cross-sectional view of the collar of FIGS. 5 and 6.

Referring now to FIGS. 3-7, collar 31 is generally cylindrical in shape corresponding to the shape of cavity 41 of housing 25. Collar 31 includes a proximal end wall 93 and a side wall 97 extending from proximal wall 93. Side wall 97 of collar 31 includes two opposed exaggerated angled L-shaped tracks 99 formed in an outer surface thereof, one of which can be seen in FIGS. 6 and 7. The other L-shaped track is not shown but is a mirror image of L-shaped track 99 shown. For simplicity, reference numeral 99 will refer to both L-shaped tracks. As seen in FIG. 6, each track 99 has a lower portion 101 defined by an upper stop wall or shoulder 103 and first and second lateral, longitudinally extending side walls 105, 107. Each track 99 further has a through portion 109 defined by second side wall 107 and a third side wall 111 which is on an end of upper stop wall 103.

On the inside surface of housing 25, facing collar 31 and projecting into each of the two L-shaped tracks 99, are two opposed longitudinally extending male ribs 113, one of which 113 can be seen in FIG. 5. The other rib is not visible but is a mirror image of visible rib 113. For simplicity reference number 113 will refer to both ribs. Each of the two ribs 113 is parallel relative to axis 37. Each rib 113 has a width which is slightly less than the gap between the second side wall 107 and the third side wall 111 defining the through portion 109.

In operation, each rib 113 cooperates with a respective L-shaped track 99 in an identical manner to permit limited rotational and axial movement of collar 31, as described herein. Specifically, contact between each rib 113 and respective first side wall 105 and second side wall 107, with respective upper stop wall 103 riding along rib 113, limits the rotational movement of collar 31 to about 6°, while collar 31 is constrained to move axially along axis 37. In this position, collar 31 supports distal seal 73 of shuttle 29 across opening 39 of housing 25.

After approximately 6° of rotational movement of collar 31, each rib 113 enters respective through portions 109 of L-shaped tracks 99, wherein contact between each rib 113 and respective second side wall and third side wall 107, 111 permits collar 31 to move axially along axis 37, but constrains collar 31 from further rotational movement. With each rib 113 in respective through portions 109, collar 31 can move axially along axis 37 toward proximal end 35 of housing 25 so that tip 61 of needle 27 can pierce abutting seals 23, 73 to place the syringe adapter 11 in an open state. Alternatively, collar 31 can move axially toward distal end 33 of housing 25 so that tip 61 of needle 27 exits seals 23, 73 and re-enters lumen 81 of shuttle 29 to place syringe adapter 11 in the closed state.

Side wall 97 of collar 31 further includes helical tracks 115, 117 formed in an outer surface thereof. Guide pins 53, 55 of any male stem 19 are received in a respective helical track 115 or 117 for purposes of rotating collar 31 and holding seals 23, 73 in abutment with one another, as will now be described.

With reference to FIGS. 32-38, syringe adapter 11 (or syringe adapter 611, see FIGS. 17-24) operates in substantially a two-step manner. Initially, a male stem 19 supporting a seal 23, such as in the vial adapter 13 (not shown), the patient push adapter 15 (as shown in FIGS. 32-38) or the I.V. bag adapter 17 (not shown), is held in abutment with distal seal 73 of shuttle 29. Then, the held-together or abutting seals 23, 73 are pierced with the tip 61 of needle 27 so that needle 27 can enter the lumen 21 of male stem 19 to open the fluid path through syringe adapter 11, thereby placing syringe adapter 11 in the open state and in fluid communication with the vial adapter 13, the patient push adapter 15 or the I.V. bag adapter 17.

Figure 34:
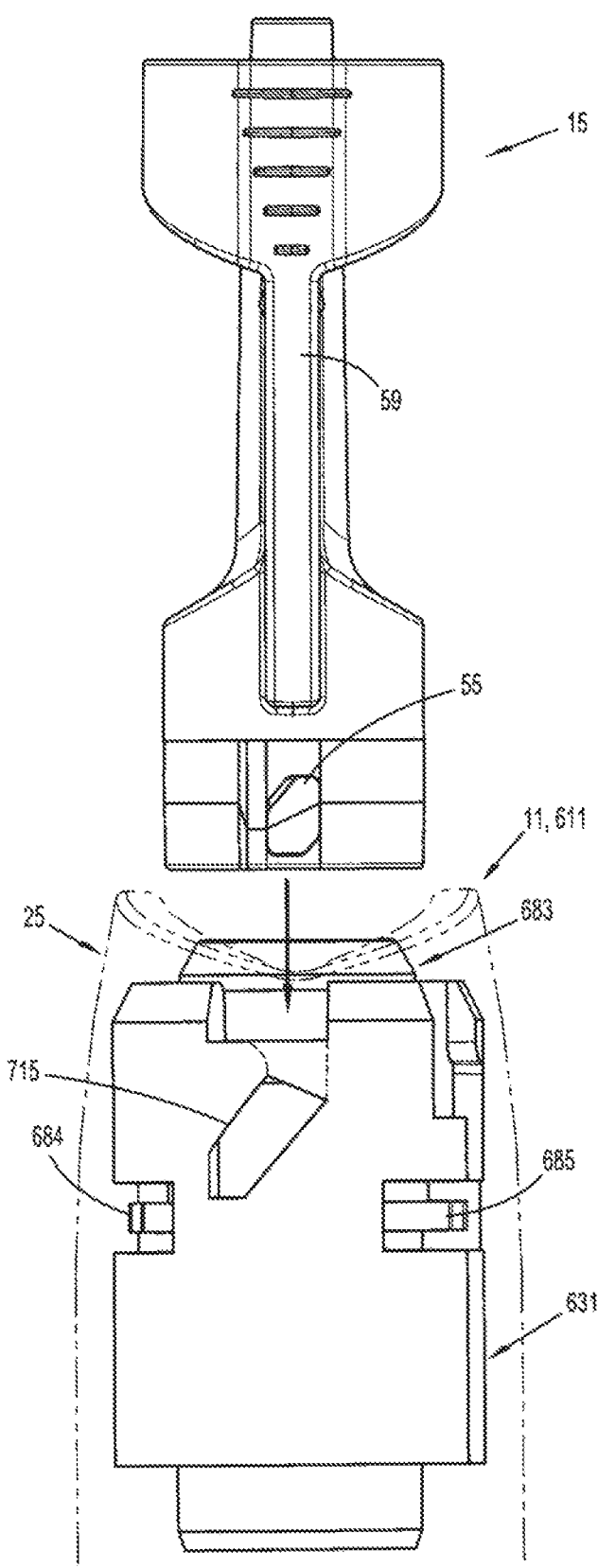
Figure 35:
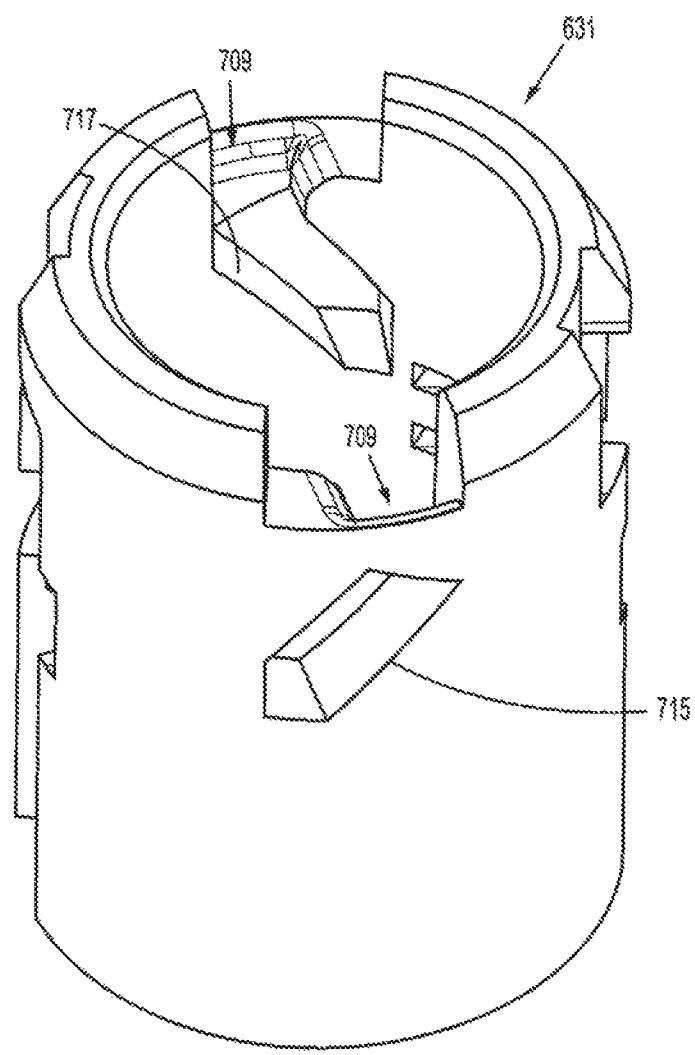
Figure 36:
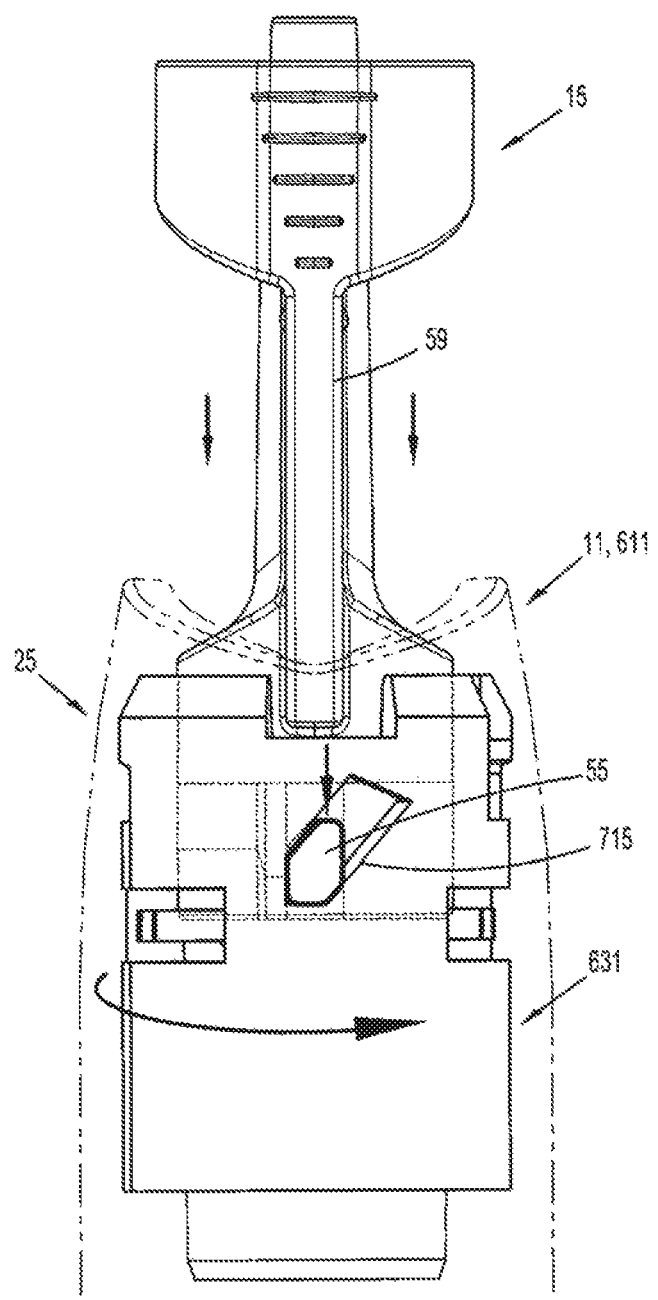
Figure 37:
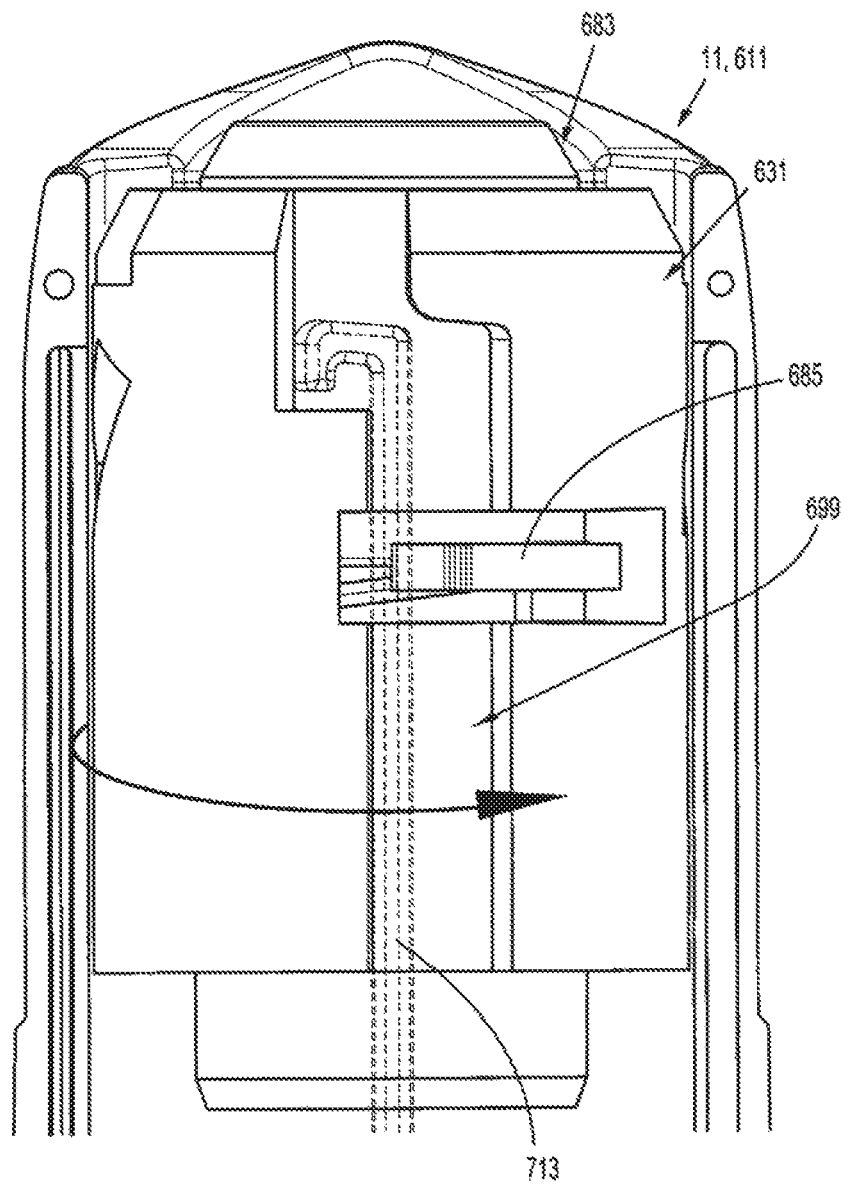

More specifically, in the initial step, as seen in FIGS. 32-34, diametrically opposed, radially extending guide pins 53, 55 of male stem 19 (of, for example, patient push adapter 15) and diametrically opposed, radially extending guide surfaces 57, 59 of male stem 19 are first inserted into respective slots 49, 51 of housing 25 with stem seal 23 of male stem 19 in abutment with distal seal 73 of shuttle 29. Next, stem seal 23 of male stem 19 enters cavity 41 (see FIGS. 4, 38) of housing 25 and guide pins 53, 55 of male stem 19 enter a respective helical track 115, 117 (or 715, 717) of collar 31 (or 631). Simultaneously, shuttle 29 moves axially along axis 37 toward end wall 93 of collar 31 (or 631) and proximal end 35 of housing 25, against spring 95 because collar 31 (or 631) is axially constrained by contact between each rib 113 (or 713) and a respective upper stop or side wall 103 of collar 31 (or 631). Due to the axial constraint imposed on collar 31 (or 631) by each rib 113 (or 713) and respective upper side walls 103, shuttle 29 will move axially toward proximal end 35 of housing 25 until barrel 83 of shuttle 29 bottoms out against end wall 93 of collar 31 (or 631).

Axial movement of guide pins 53, 55 of male stem 19, within a respective collar helical track 115, 117 (or 715, 717), while collar 31 (or 631) is axially constrained, causes collar 31 (or 631) to rotate (counterclockwise as illustrated in the FIGS. 36 and 37) and each of the two upper side walls 103 of collar 31 (or 631) to slide along a respective rib 113 (or 713). As mentioned above, this rotation of collar 31 (or 631) is limited to about 6° by contact between ribs 113 (or 713) and a respective second side wall 107. Male stem 19 is unable to rotate as male stem 19 is inserted into syringe adapter 11 (or 611) because guide surfaces 57, 59 of male stem 19 are constrained within slots 49 and 51 of housing 25.

The restraint on further rotation of collar 31 (or 631), provided by contact between the ribs 113 (or 713) and the respective second side walls 107, in turn, limits further axial movement of male stem 19 because the guide pins 53, 55 of male stem 19 are now axially constrained by the helical tracks 115, 117 (or 715, 717) of collar 31 (or 631). When shuttle 29 is bottomed out against end wall 93 of collar 31 (or 631), further axial movement of shuttle 29 relative to collar 31 (or 631) is prevented. The result is that seal 23 of male stem 19 is held in abutment against distal end seal 73 of shuttle 29. Tip 61 of needle 27 remains axially spaced from abutting seals 23, 73 and there is no fluid flow through syringe adapter 11 (or 611).

Figure 38:
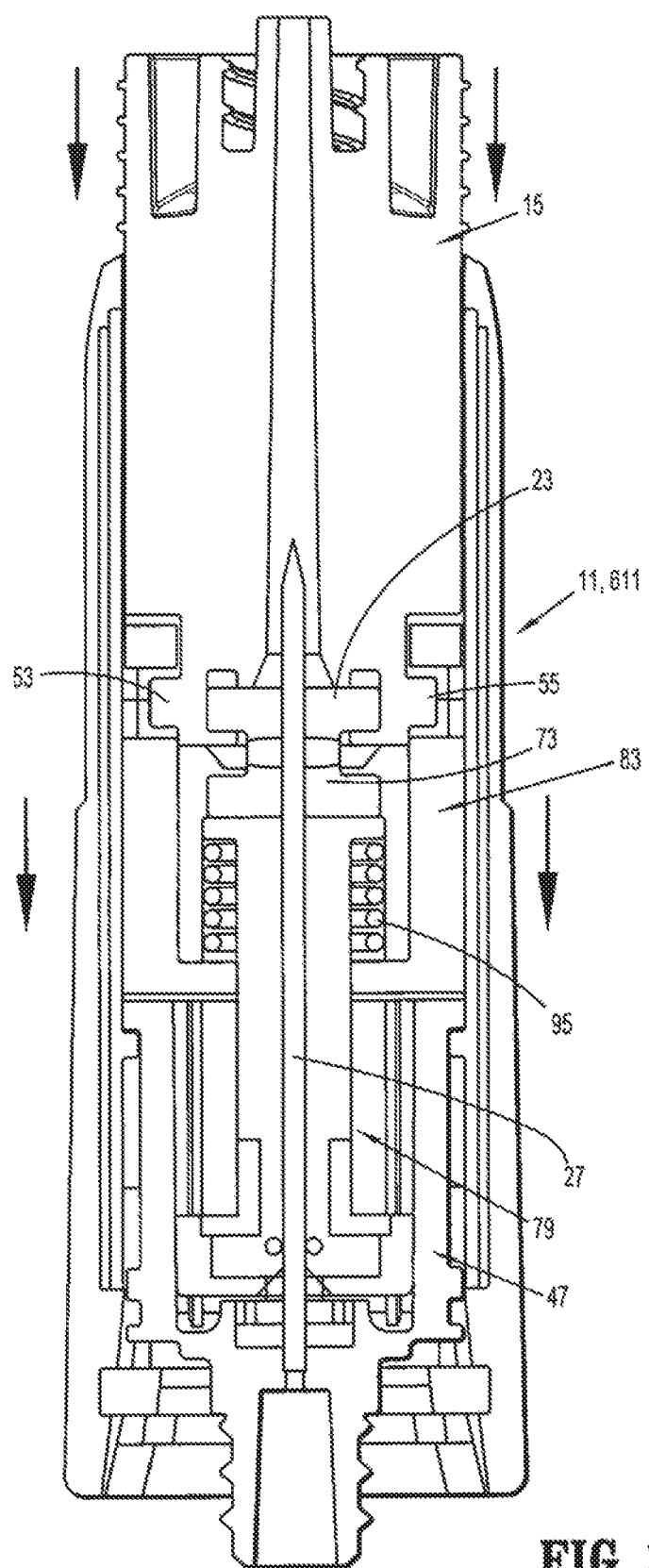

In the following step, as seen in FIG. 38, the user pushes male stem 19 and abutting seals 23, 73 further into cavity 41 of housing 25 (see FIGS. 4, 38) of syringe adapter 11 (or 611). Further axial movement of shuttle 29 and collar 31 is possible now because collar 31 has been rotated so that through portion 109 of each collar L-shaped track 99 (see FIGS. 5-7) is in alignment with a rib 113 (or 713), wherein ribs 113 (or 713) are between second and third side walls 107, 111 (see FIGS. 5-7). Further movement of male stem 19 into cavity 41 (see FIG. 4) moves collar 31 (or 631) and abutting seals 23, 73 toward tip 61 of needle 27 causing tip 61 of needle 27 to pierce the abutting seals 23, 73 and further causing needle 27 to enter lumen 21 of male stem 19 to open the fluid path through syringe adapter 11 (or 611), thereby placing syringe adapter 11 (or 611) in the open state and in fluid communication with the vial adapter 13 (not shown), the patient push adapter 15 or the I.V. bag adapter 17 (not shown). Fluids can now flow from needle 27 toward the vial adapter 13, the patient push adapter 15 or the I.V. bag adapter 17, or can flow in a reverse direction.

To remove the male stem 19 of the vial adapter 13 (not shown), the patient push adapter 15 or the I.V. bag adapter 17 (not shown) from syringe adapter 11 (or 611), the adapter 13, 15, or 17 is pulled fully away from the distal end 33 of housing 25. The process described above takes place in reverse, thereby stopping a flow of fluid once needle tip 61 is fully retracted within lumen 81 of shuttle 29 (see FIG. 4), thereby placing the syringe adapter 11 (or 611) into the closed state.

Figure 11:
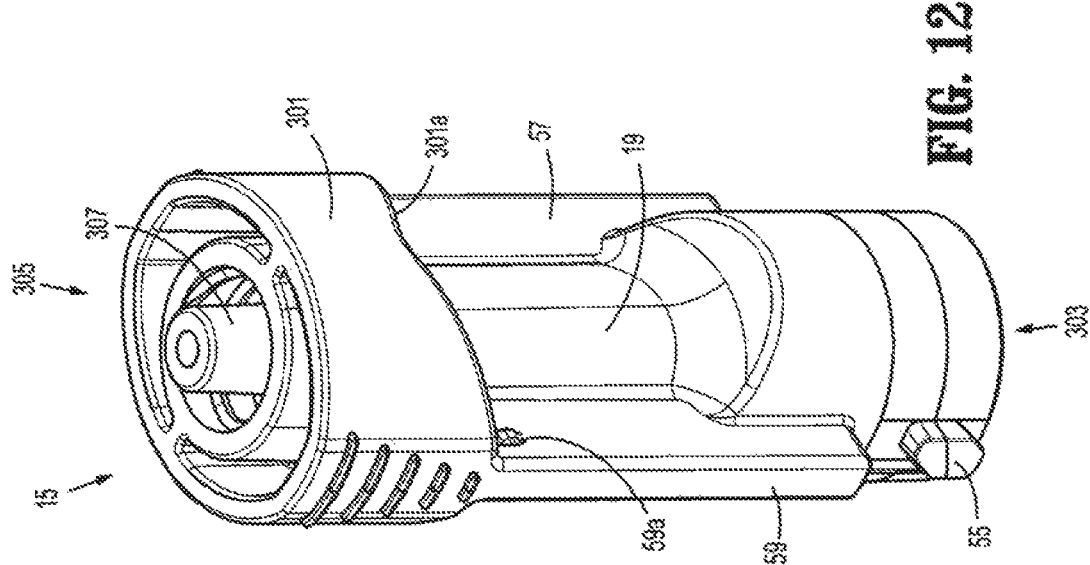
FIG. 11 is a top, perspective view of a patient push adapter of the closed fluid transfer system of FIG. 1.
Figure 12:
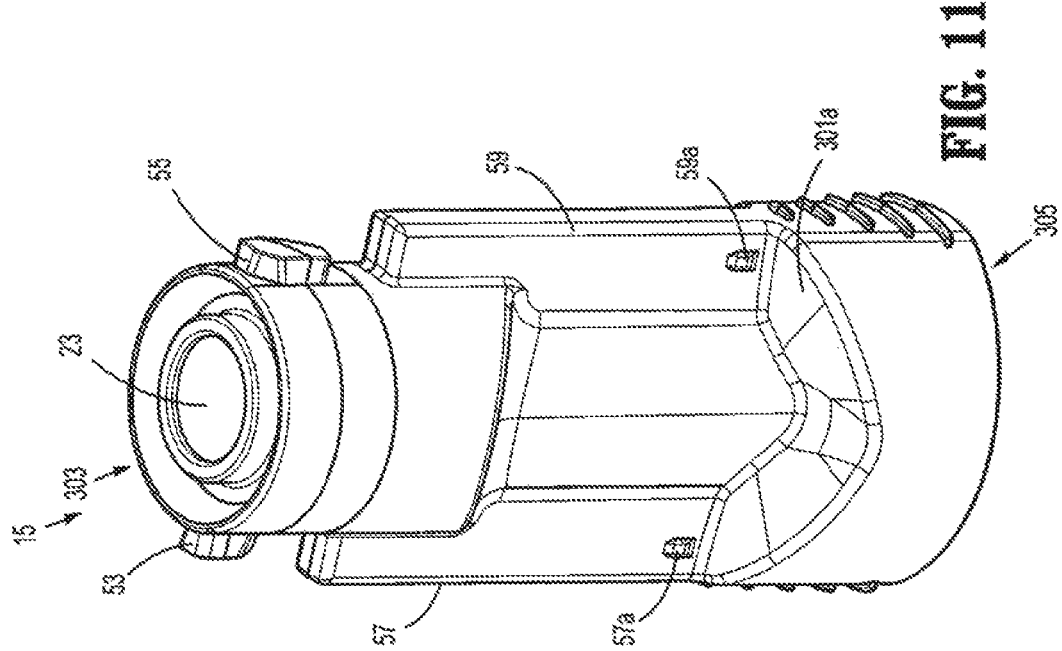
FIG. 12 is a bottom, perspective view of a patient push adapter of the closed fluid transfer system of FIG. 1.
Figure 13:
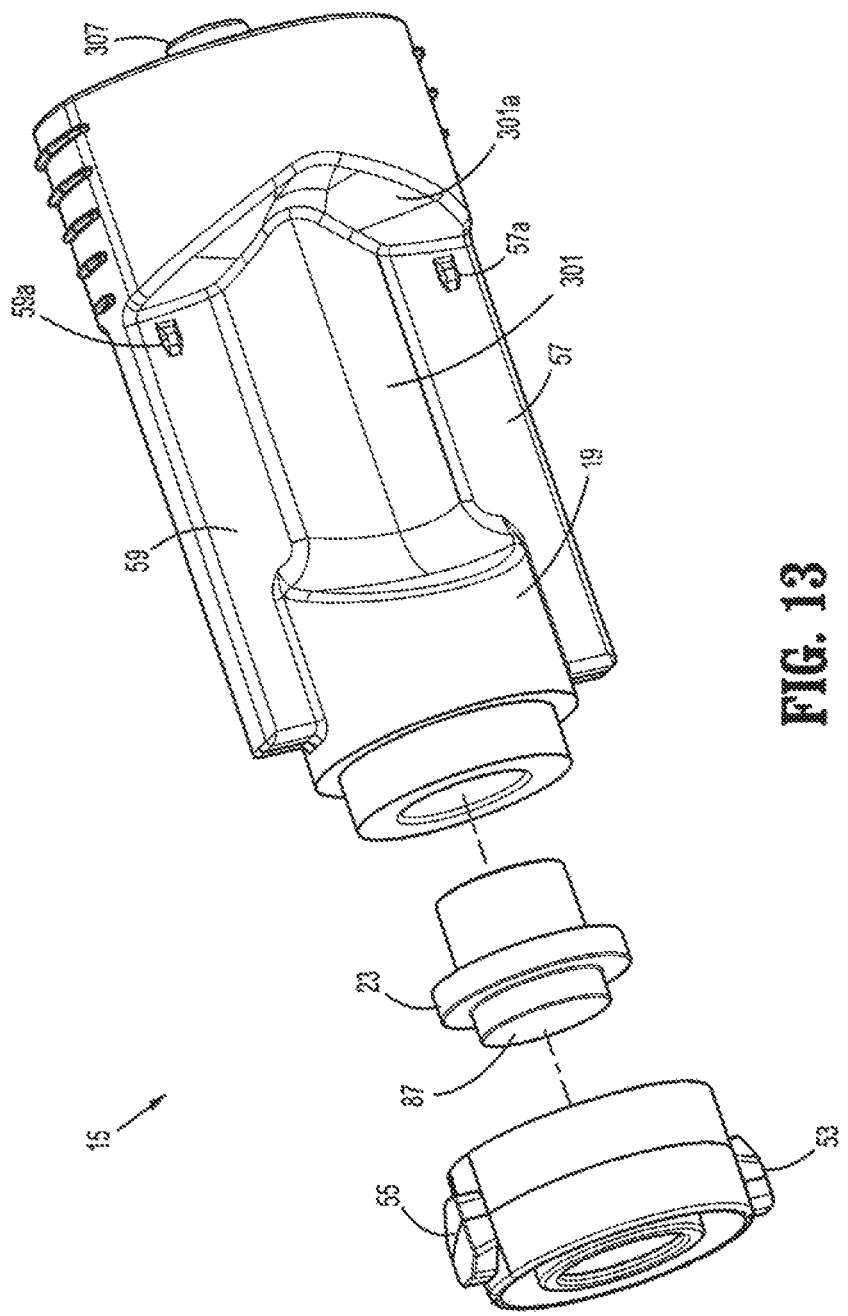
FIG. 13, is a perspective view, with parts separated, of the patient push adapter of FIGS. 11 and 12.
Figure 14:
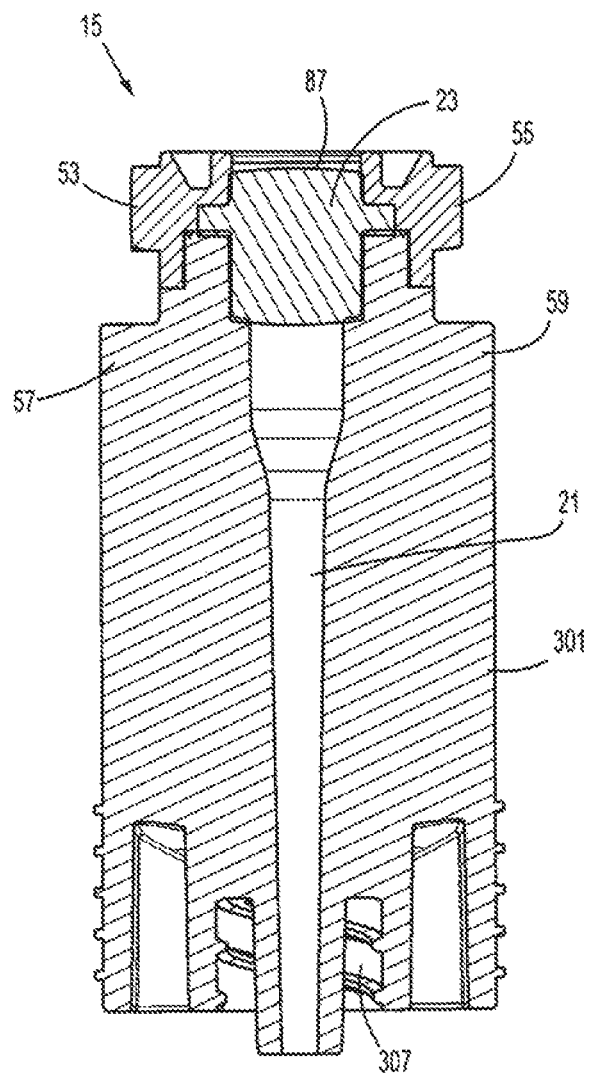
FIG. 14 is a longitudinal, cross-sectional view of the patient push adapter of FIGS. 11-13.

In accordance with the present disclosure, as seen in FIGS. 2-5, it is further contemplated that distal end 33 of housing 25 of syringe adapter 11 may have a substantially sinusoidal distal profile or distal end surface 33a (see FIG. 2), wherein opposed slots 49, 51 of syringe adapter 11 are disposed at a respective opposed nadir or low point of distal end surface 33a. Meanwhile, as seen in FIGS. 11-13, body 301 of patient push adapter 15 may include a substantially sinusoidal profile or surface 301a extending therearound, wherein opposed guide surfaces 55, 57 of patient push adapter 15 are disposed and a respective opposed apex or high point of surface 301a. It is contemplated that distal end surface 33a of syringe adapter 11 and surface 301a of patient push adapter 15 substantially complement one another.

Turning now to FIGS. 1 and 8-10, vial adapter 13 of the closed fluid transfer system 100 of the present disclosure, will be discussed in greater detail. Generally, vial adapter 13 connects to a neck "N" of a vial, bottle, or other container "V" holding liquid "L" to be extracted or into which liquid is to be delivered. For convenience, these containers will be referred to collectively by the term "vial." Vial adapter 13 may be provided in sizes and configurations as necessary to attach to commercially-available vials.

Figure 9:
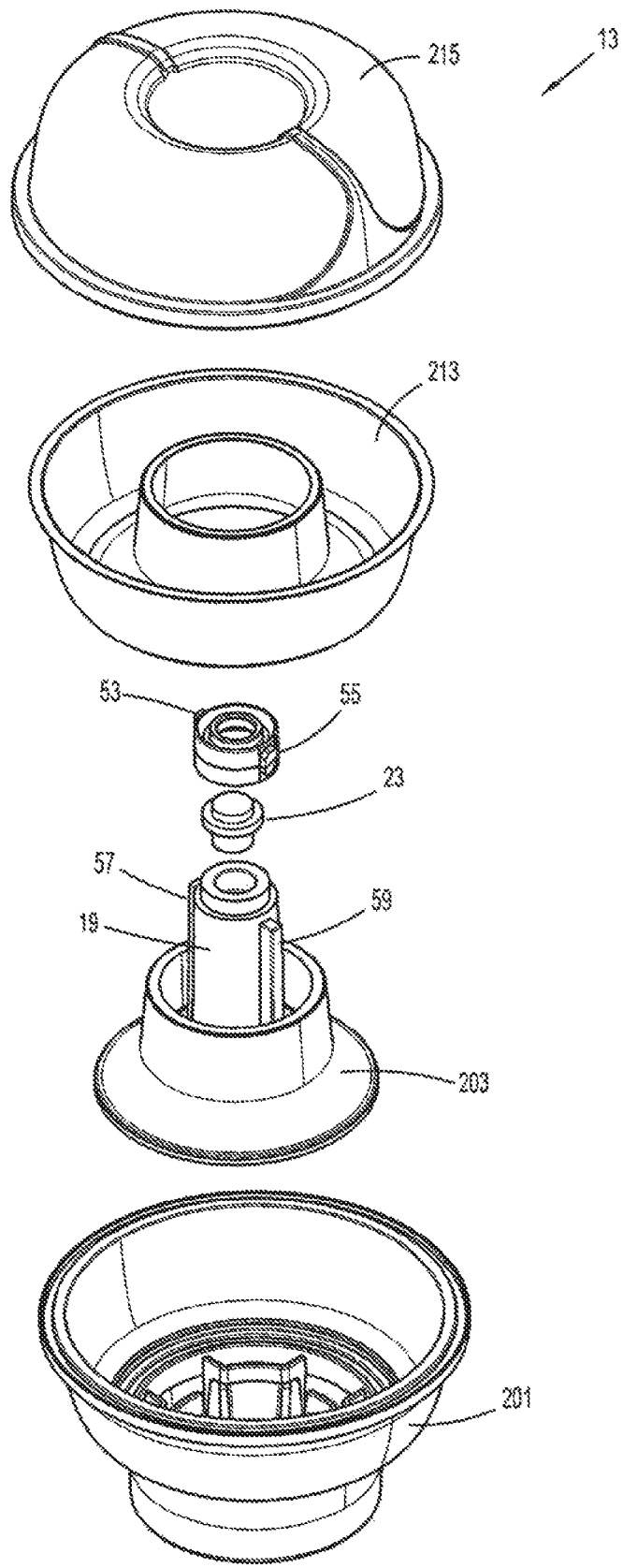
FIG. 9 is a perspective view, with parts separated, of the vial adapter of FIG. 8.
Figure 10:
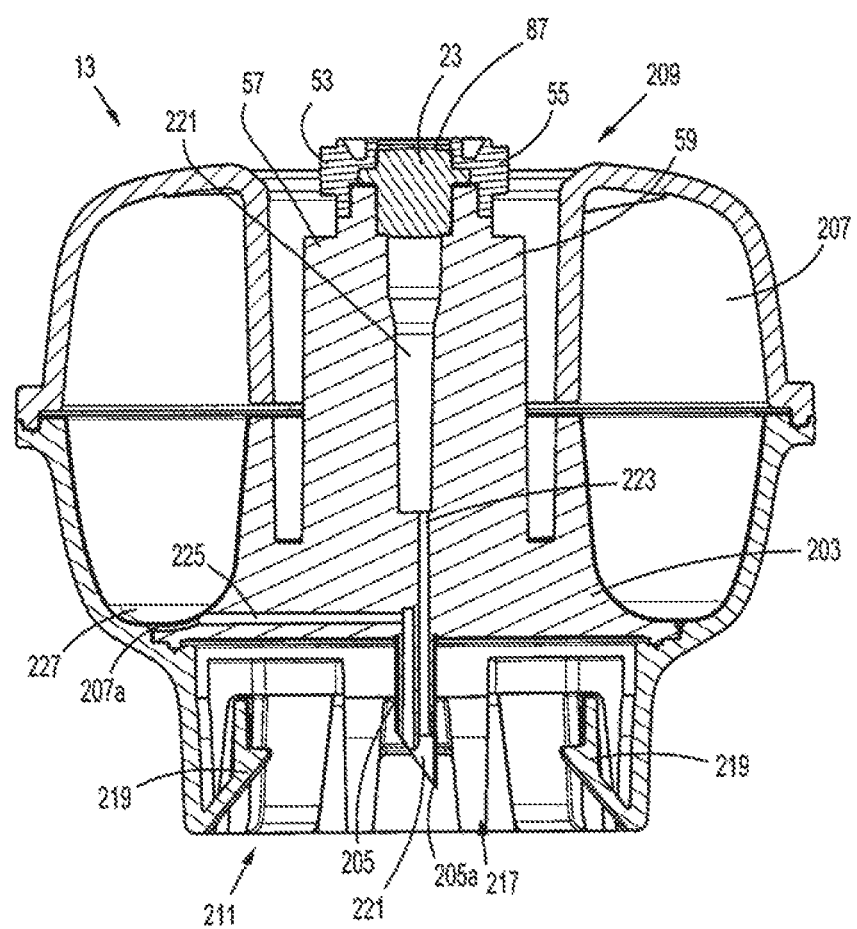
FIG. 10 is a longitudinal, cross-sectional view of the vial adapter of FIGS. 8 and 9.

As illustrated in FIGS. 8-10, vial adapter 13 includes a base 201, an adapter support 203 (including a male stem 19 supporting a seal 23 and including guide pins 53, 55, as described above), a spike 205, and an expansion chamber 207. Vial adapter 13 includes distal and proximal ends 209, 211.

As best shown in FIGS. 9 and 10, base 201 is substantially bowl-shaped and is configured to receive and/or seat an adapter support 203 thereon. Vial adapter 13 includes a toroid-shaped expansion chamber 207, including a bladder 227 and translucent cover 215, seated on an inner rim and an outer rim of base 201. Bladder 227 having a substantially U-shaped radial cross-section including a first annular rim captured between the outer annular rim of base 201 and the outer annular rim of cover 215, and a second annular rim captured between the inner annular rim of base 201 and the inner annular rim of cover 215.

Base 201 of vial adapter 13 includes a circular opening 217 along proximal end 211 thereof into which neck "N" of vial "V" is received. Retainers 219 are provided around the circumference of opening 217 to connect base 201 of vial adapter 13 to form a permanent connection once the neck "N" of the vial "V" is inserted into opening 217.

As seen in FIG. 10, spike 205 extends away from proximal end 211 of base 201 and includes a tip 221 configured to pierce a septum "S" provided on vial "V" when the neck "N" of the vial "V" is inserted into opening 217 of base 201. Spike 205 has a length sufficient to extend into the vial "V". Spike 205 is preferably made of plastic, however, it is envisioned that spike 205 may preferably support a metallic piercing member or hypo-tube 205a to assist in the ability of spike 205 to penetrate the septum "S" of the vial "V".

As seen in FIG. 10, spike 205 and adapter support 203 define two ducts 223, 225. A first duct 223 extends between tip 221 of spike 205 and lumen 21 of male stem 19, and is provided to permit fluid flow between the vial "V" and male stem 19. As described above, opening 63 of tip 61 of needle 27 extends into lumen 21 to extract or deliver liquid through duct 223 when syringe adapter 11 is in the open state. A second duct 225 extends between tip 221 of spike 205 and a first cavity 207a of chamber 207 defined within expansion chamber 207 when toroid-shaped bladder 227 is deflated. Chamber 207a of expansion chamber 207 expands upon a movement of bladder 227 when air or other gas is injected into male stem 19 and duct 223 from a syringe "I" that is attached to syringe adapter 11.

In operation, vial adapter 13 is initially connected to neck "N" of vial "V" with spike 205 piercing septum "S" of vial "V" such that ducts 223, 225 of spike 205 extend into the vial "V". Syringe adapter 11 (as shown and described above) is then attached to male stem 19 of vial adapter 13, as described previously. Liquid "L" may then be extracted from or delivered to the vial "V". If the user wishes to first charge the syringe "I" with air or other gas, then the air may be transferred through the ducts 223, 225 of spike 205 of vial adapter 13 and into first cavity 207a of chamber 207, wherein bladder 227 is moved to accommodate the air. Air in first cavity 207a of chamber 207 moves back into the vial "V" as liquid "L" is withdrawn from the vial "V" and into the syringe "I".

The vial "V" and vial adapter 13 are discarded once the liquid "L" is removed from the vial "V".

It is contemplated and understood that proximal end 211 of base 201 may be sized to accommodate different size necks of different size vials, such as, for example, a 20 mm vial cap of a 60 ml vial; a 28 mm vial cap of a 60 ml vial; and a 13 mm vial cap of a 20 ml vial. Accordingly, a diameter of proximal end of base 201 of vial adapter 13 may be sized appropriately so as to accommodate at least the caps of the vials identified above.

It is contemplated that at least one nub (not shown) may project from a surface of respective guide surfaces 57, 59 of vial adapter 13 and which are configured to snap-fit engage respective complementary detents or recesses defined in slots 49, 51 of syringe adapter 11, or more particularly, an appropriately sized annular rib 49a (see FIG. 3) formed in an inner surface of halves 43, 45 of housing 21 of syringe adapter 11. The interaction of the nubs of the guide surfaces 57, 59 of vial adapter 13 and complementary detents or recesses defined in slots 49, 51 or annular rib 49a (see FIGS. 3 and 4) of syringe adapter 11 provide a user with audible and/or tactile feedback that vial adapter 13 and syringe adapter 11 are properly and fully connected to one another.

Turning now to FIGS. 1 and 11-14, patient push adapter 15 of the closed fluid transfer system 100 of the present disclosure, will be discussed in greater detail. In general, patient push adapter 15 connects to tubing of a patient I.V. set permitting delivery of liquids directly to the patient from a syringe "I" attached to the patient push adapter 15.

The patient push adapter 15 includes a body 301 having respective distal and proximal ends 303, 305. Body 301 of patient push adapter 15 is preferably a one-piece molded plastic part. Distal end 303 of patient push adapter 15 includes a male stem 19 defining a lumen 21, having a seal 23 supported across lumen 21, having guide pins 53, 55 projecting radially outward from on outer surface thereof, and having guide surfaces 57, 59 projecting radially outward from on outer surface thereof. Proximal end 305 of patient push adapter 15 includes a conventional luer connector 307 configured to accept a mating luer connector of a patient I.V. set "IV" (see FIG. 1). Lumen 21 extends through body 301, between seal 23 and luer connector 307, permitting fluid flow between the opening 63 of tip 61 of needle 27 and the luer connector 307, when patient push adapter 15 is properly connected to syringe adapter 11, as described above.

With reference to FIGS. 11-13, it is contemplated that at least one nub 57a, 59a may project from a surface of respective guide surfaces 57, 59 of patient push adapter 15 and which are configured to snap-fit engage respective complementary detents or recesses defined in slots 49, 51 of syringe adapter 11, or more particularly, an appropriately sized annular rib 49a (see FIG. 3) formed in an inner surface of halves 43, 45 of housing 25 of syringe adapter 11. The interaction of nubs 57a, 59a, and complementary detents or recesses defined in slots 49, 51 or annular rib 49a (see FIGS. 3 and 4) of syringe adapter 11 provide a user with audible and/or tactile feedback that patient push adapter 15 and syringe adapter 11 are properly and fully connected to one another.

Guide surfaces 57, 59 of patient push adapter 15 provide a convenient and comfortable surface for a user to grip patient push adapter 15 and to rotate patient push adapter 15 relative to a conventional luer of I.V. set.

Figure 15:
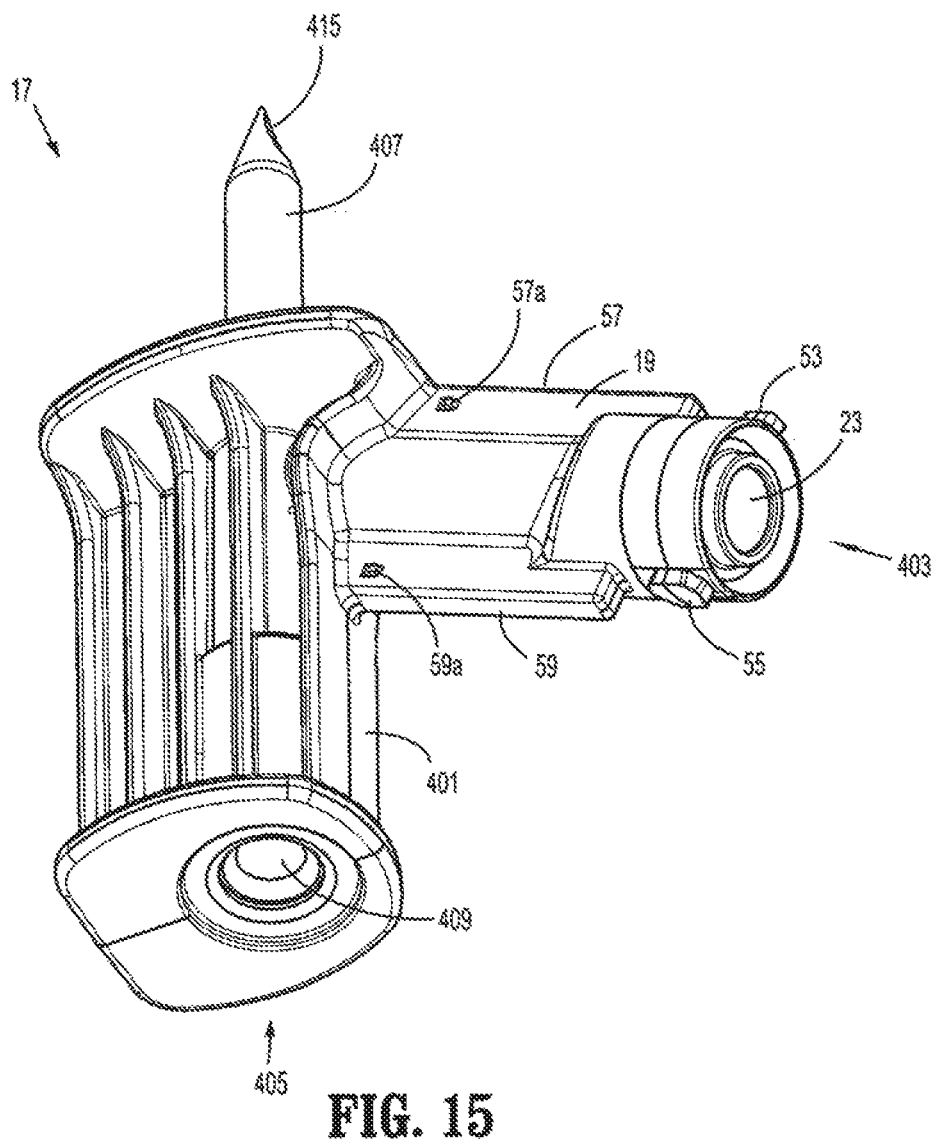
FIG. 15 is a bottom, perspective view of an I.V. bag adapter of the closed fluid transfer system of FIG. 1.
Figure 16:
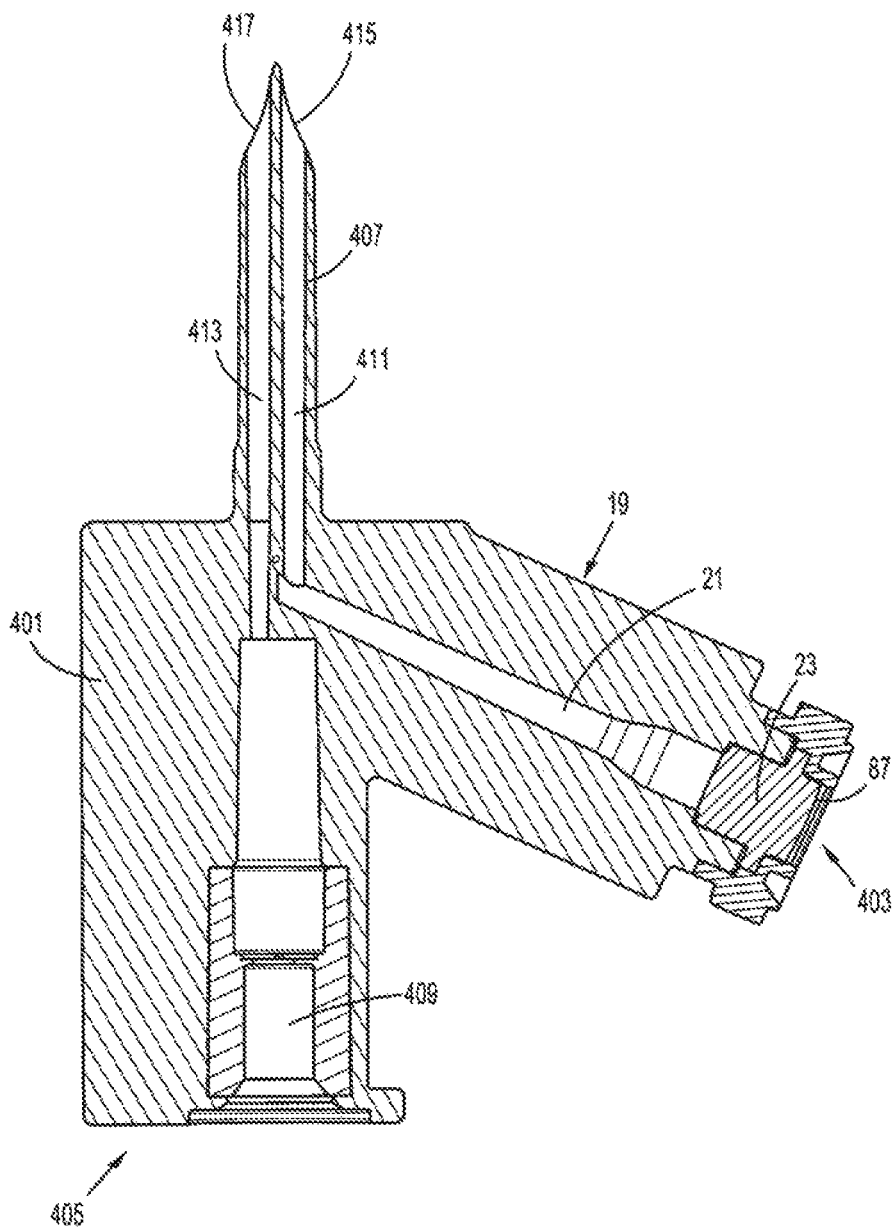
FIG. 16 is a longitudinal, cross-sectional view of the I.V. bag adapter of FIG. 15.

Turning now to FIGS. 1 and 15-16, I.V. bag adapter 17 of the closed fluid transfer system 100 of the present disclosure, will be discussed in greater detail. In general, the I.V. bag adapter 17 enables liquid to be delivered to, or extracted from, a conventional I.V. bag "B" (see FIG. 1). The I.V. bag adapter 17 could also be used as a source of ventilation, permitting air to be delivered from a syringe "I" or other source into the I.V. bag to more rapidly drain the I.V. bag "B" of its liquid contents.

The I.V. bag adapter 17 includes a body 401 having respective distal and proximal ends 403, 405, and a spike 407 extending from body 401. Distal end 403 of I.V. bag adapter 17 includes a male stem 19 defining a lumen 21, having a seal 23 supported across lumen 21, having guide pins 51, 53 projecting radially outward from on outer surface thereof, and having guide surfaces 57, 59 projecting radially outward from on outer surface thereof. Body 401 of I.V. bag adapter 17 is preferably a one-piece molded plastic part. Proximal end 405 of body I.V. bag adapter 17 includes a conventional port 409 which receives a conventional tapered male connector (not shown) of a conventional infusion chamber (not shown) into which liquid drips from the I.V. bag "B". Spike 407 is tapered between distal and proximal ends 403, 405 for insertion into a conventional port (not shown) of I.V. bag "B".

Body 401 of I.V. bag adapter 17 includes two ducts 411, 413. First duct 411 is essentially an extension of lumen 21 through spike 407 extending to an opening 415 in spike 407 which would be within I.V. bag "B" when I.V. bag adapter 17 is attached to the I.V. bag "B". Second duct 413 extends between a second opening 417 in spike 407 and a port 409 for attachment to the infusion chamber (not shown). As described above, opening 63 of tip 61 of needle 27 extends into lumen 21 of male stem 19, when I.V. bag adapter 17 is properly connected to syringe adapter 11, to extract or deliver liquid (or gas) through duct 411 while syringe adapter 11 is in the open state.

In accordance with the present disclosure, a component other than a syringe adapter 11 could be connected to male stem 19 of I.V. bag adapter 17 to deliver gas to I.V. bag "B". Liquid medication delivered through duct 411 may be mixed with the contents of the I.V. bag "B". The liquid in the I.V. bag "B" may then exit the I.V. bag "B" through port 409 and into the infusion chamber for delivery to the patient.

With reference to FIGS. 15 and 16, it is contemplated that at least one nub 57a, 59a may project from a surface of respective guide surfaces 57, 59 of I.V. bag adapter 17 and which are configured to snap-fit engage respective complementary detents or recesses defined in slots 49, 51 of syringe adapter 11, or more particularly, an appropriately sized annular channel 49a (see FIG. 3) formed in an inner surface of halves 43, 45 of housing 25 of syringe adapter 11. The interaction of nubs 57a, 59a and complementary detents or recesses defined in slots 49, 51 or annular rib 49a (see FIGS. 3 and 4) of syringe adapter 11 provide a user with audible and/or tactile feedback that I.V. bag adapter 17 and syringe adapter 11 are properly and fully connected to one another.

Turning now to FIGS. 17-24, a syringe adapter, according to another embodiment of the present disclosure, is generally designated as 611. Syringe adapter 611 is substantially similar to syringe adapter 11 and thus will only be discussed in detail hereinbelow to the extent necessary to describe differences in construction and operation therebetween.

Figure 18:
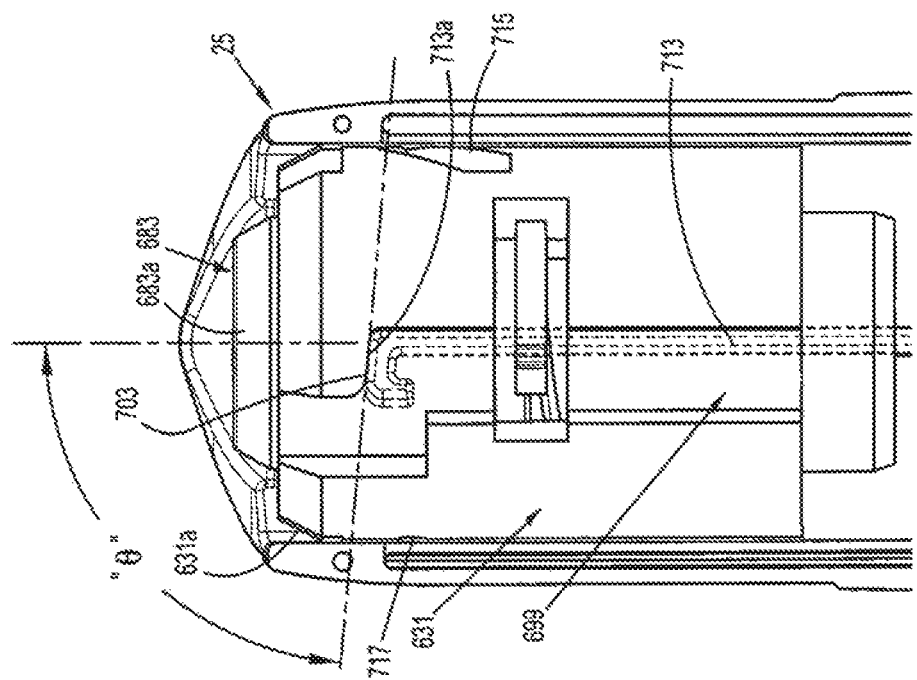
FIG. 18 is a side, elevational view of a distal end of the syringe adapter of FIG. 17, with one housing half removed.
Figure 17:
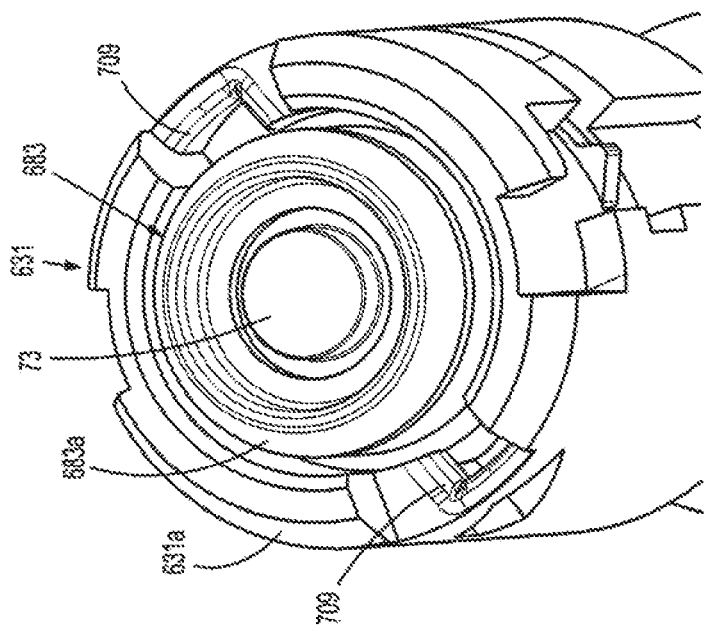
FIG. 17 is a distal, perspective view of a syringe adapter, with the housing removed, according to another embodiment of the present disclosure.

As seen in FIGS. 17-19, a respective distal or leading edge 631a, 683a of collar 631 and barrel 683 is chambered to thereby improve the mating of syringe adapter 611 with vial adapter 13, patient push adapter 15, and I.V. bag adapter 17. Additionally, a lead in for each through portion 709, defined in an outer surface of collar 631, has been chamfered so as to better guide the guide pins 53, 55 of any male stem 19 into through portions 709.

As seen in FIG. 18, upper stop wall 703 of each track 699 of collar 631 is oriented at an angle relative to a longitudinal axis of track 699. In particular, upper stop wall 703 is oriented at an angle "O" of approximately 85° relative to the longitudinal axis of track 699. It is also contemplated that a distal-most surface 713a of ribs 713 is also oriented at an angle that substantially compliments the angle of upper stop wall 703. Such an angle of incline for upper stop wall 703 of each track 699 of collar 631 and of distal-most surface 713a of each rib 713, facilitates the ability of collar 631 to rotate relative to housing 25 of syringe adapter 611.

As illustrated in FIG. 19, collar 631 includes helical tracks 715, 717 formed in an outer surface thereof. Each track 715, 717 defines a pitch or angle relative to a longitudinal axis of collar 631 equal to approximately 50°. In this manner, the angle or pitch of helical tracks 715, 717 of collar 631 is greater than the angle or pitch of helical tracks 115, 117 of collar 31.

Referring now to FIGS. 21-24, syringe adapter 611 includes a lock-out feature that prevents an inadvertent rotation of collar 631, relative to housing 25, prior to engagement of seal 73 by the seal 23 of any of the male stems 19. The lock-out feature includes a shuttle 629 having a relatively larger diameter proximal portion 683a of barrel 683 transitioning to a relatively smaller diameter distal portion 683b of barrel 683. The lock-out feature includes a pair of diametrically opposed resilient lock arms 684, 685 formed in collar 631. Each lock arm 684, 685 extends in a radial direction about collar 631 and includes a first end 684a, 685a integrally formed or extending from collar 631, and a free second end 684b, 685b. The free second end 684b, 685b of each lock arm defines a tooth for engaging a respective rib 713.

In use, when shuttle 629 is in a non-depressed condition, as seen in FIGS. 21 and 22, proximal portion 683a of barrel 683 of shuttle 629 is dimensioned so as to press against resilient lock arms 684, 685 formed in collar 631 or act as a barrier or wall against resilient lock arms 684, 685 formed in collar 631, so as to prevent resilient lock arms 684, 685 from deflecting radially inward and disengaging respective ribs 713. Since the tooth of lock arms 684, 685 is in engagement with respective ribs 713 of housing 25, collar 631 is prevented from rotating relative to housing 25 and thus prematurely enabling collar 631 from being depressed (after rotation) relative to housing 25.

As illustrated in FIGS. 23-24, in use, as shuttle 629 is pressed into collar 631, upon a coupling with any of the male stems 19, as described above, distal portion 683b of barrel 683 of shuttle 629 aligns with or comes into registration with lock arms 684, 685 of collar 631. With the resilient lock arms 684, 685 overlying distal portion 683b of barrel 683 of shuttle 629, distal portion 683b of barrel 683 of shuttle 629 is spaced a distance radially inward of lock arms 684, 685 by an amount sufficient to allow lock arms 684, 685 to deflect radially inward and snap over respective ribs 713 as collar 631 is rotated relative to housing 25.

As seen in FIGS. 22 and 24, lock arms 684, 685 are mirrored about a plane extending parallel to a longitudinal axis of collar 631 and extending substantially equally between lock arms 684, 685.

Referring now to FIGS. 25-31, closed fluid transfer system 100, of the present disclosure, may include a universal vial adapter 813. Generally, universal vial adapter 813 connects to various sized caps or necks of vials holding a liquid to be extracted or into which liquid is to be delivered. For example, universal vial adapter 813 may be configured to connect to vials having either a 20 mm vial cap or a 28 mm vial cap. While 20 mm and 28 mm vial caps are identified, it is contemplated that universal vial adapter 813 may be configured and dimensioned to accommodate and/or connect to any size cap of any vial or the like.

Figure 25:
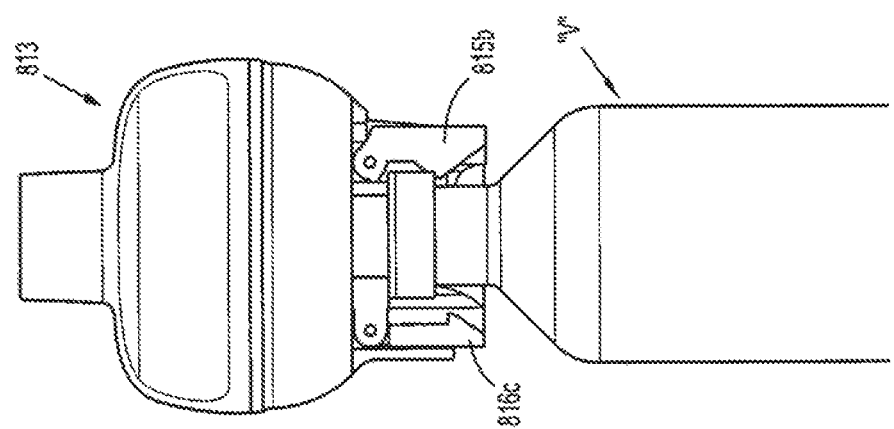
FIG. 25 is a schematic, elevational view of a universal vial adapter according to an embodiment of the present disclosure, shown connected to a vial neck having a first diameter.
Figure 26:
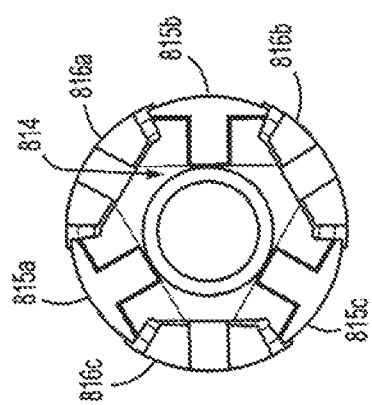
FIG. 26 is a top, plan view of a hub of the universal vial adapter as connected to the vial of FIG. 25.
Figure 27:
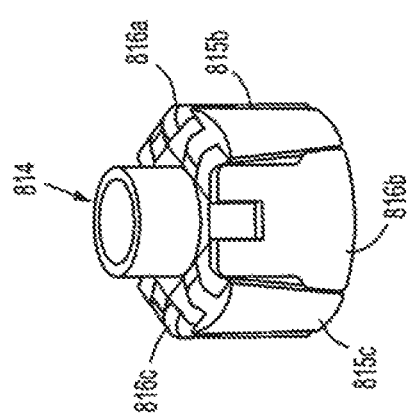
FIG. 27 is a perspective view of the hub of the universal vial adapter as connected to the vial of FIG. 25.
Figure 31:
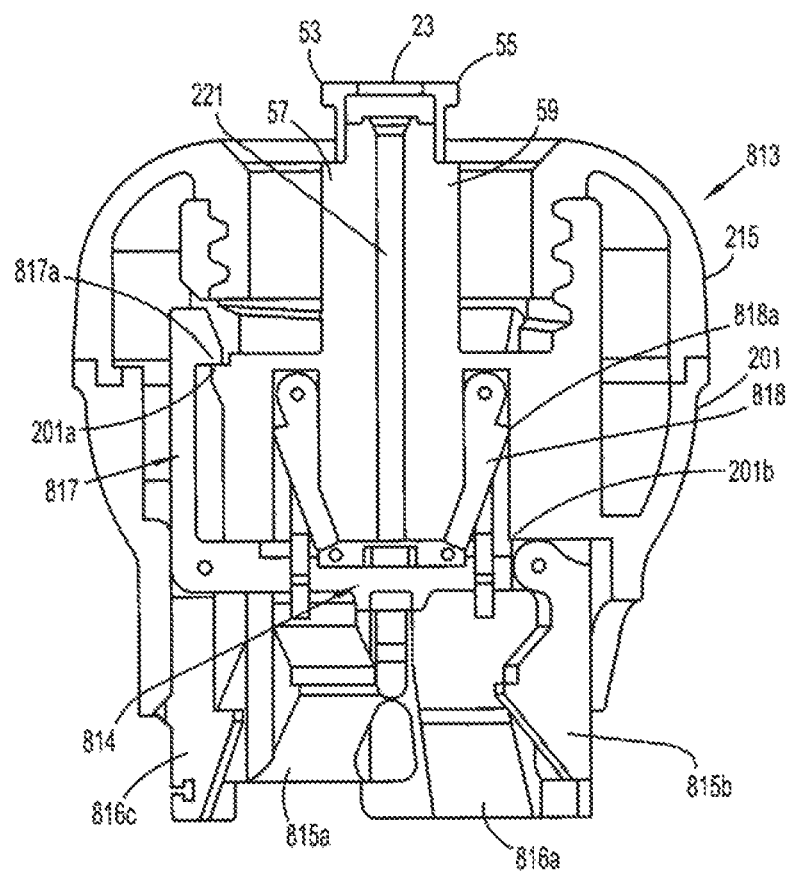
FIG. 31 is a schematic, longitudinal, cross-sectional view of the universal vial adapter of FIGS. 25-30.

Universal vial adapter 813 includes three, equally radially spaced apart first claws 815a, 815b, 815c supported on a hub 814 and which are configured to engage an outer rim of a relatively smaller diametered cap (e.g., a 20 mm vial cap as seen in FIG. 25). Universal vial adapter 813 also includes three, equally radially spaced apart second claws 816a, 816b, 816c supported on a hub 814 and which are configured to engage an outer rim of a relatively larger diametered cap (e.g., a 28 mm vial cap as seen in FIG. 28). Each second claw 816a, 816b, 816c is interposed between adjacent first claws 815a, 815b, 815c.

It is contemplated that each claw 815a, 815b, 815c and each claw 816a, 816b, 816c is biased to a closed condition.

It is further contemplated that hub 814 is slidably disposed within base 201 of universal vial adapter 813. Universal vial adapter 813 includes a locking system including at least one first latch arm 817 having a shoulder 817a which engages a first shoulder 201a of base 201 when hub 814 is in a fully pressed-in condition. The locking system of universal vial adapter 813 includes at least one second latch arm 818 having a shoulder 818a which engages a second shoulder 201b of base 201 when hub 814 is in a fully non-pressed-in condition.

In use, the at least one second latch arm 818 of the locking system maintains hub 814 in the fully non-pressed-in condition until a relatively smaller cap is fully engaged by first claws 815a, 815b, 815c or until relatively larger cap is fully engaged by second claws 816a, 816b, 816c. Once the cap is fully engaged by first claws 815a, 815b, 815c or second claws 816a, 816b, 816c, the at least one second latch arm 818 of the locking system disengages from second shoulder 201b of base 201, allowing hub 814 to be moved to the pressed-in condition. When hub 814 is moved to the pressed-in condition, the shoulder 817a of the at least one first latch arm 817 engages the first shoulder 201a of base 201 to maintain hub 814 in the pressed-in condition.

An important aspect of the present disclosure is the alignment and contact of seal 73 of syringe adapters 11 or 611 with seal 23 of male stems 19 of patient push adapter 13, vial adapters 15 and 815, and I.V. bag adapter 17. Ensuring that seals 73 and 23 are in proper alignment with one another is important to ensure that needle 27 penetrates through both seals 73 and 23 upon complete coupling/connecting of syringe adapters 11, 611 with patient push adapter 13, vial adapters 15 and 815, and I.V. bag adapter 17.

Another important aspect of the present disclosure is the ability of the user to swab, wipe, clean and/or disinfect seals 73 and 23 prior to or following their use.

Also in accordance with the present disclosure, each seal 23 and 73 is provided with a constant pressure radially inward along an entire length of seal 23, 73 such that the distal and proximal surfaces of seals 23, 73 are convex or arc outward. As such, the seal to seal contact between abutting seals 23 and 73 is improved.

While the above disclosure and related figures illustrate syringes, vials, I.V. sets, and I.V bags as exemplary embodiments, it is envisioned and within the scope of the present disclosure that any of the adapters described herein may be used in cooperation with any fluid container, such as, for example, bottles, test tubes, trays, tubs, vats, jars, bathes, pools, pressure vessels, balloons, ampoules, etc.

Reference may be made to U.S. Patent Publication No. 2013-0066293, filed on Nov. 26, 2012, entitled "CLOSED FLUID TRANSFER SYSTEM," the entire content of which is incorporated herein by reference, for a detailed discussion and illustration of syringe adapters 11, patient push adapters 13, vial adapters 15 and 815, and I.V. bag adapters 17.

In accordance with the present disclosure, a preparation system 1000 for automatically or semi-automatically preparing hazardous medicines using syringes, vials, I.V. sets, and I.V bags of the present disclosure, is also provided and set forth below, illustrated in FIGS. 40A-40G.

Preparation system 1000 includes, as seen in FIGS. 40A-40G, at least the following sub-systems and/or stations, namely, a rotation station (RS), a weigh station (WS), a transfer station (TS), component holders (CH), at least one manipulator (M), at least one gripper (G), and at least one barcode scanner (BS). Preparation system 1000 may be considered a Closed System Transfer Device (CSTD).

The Closed System Transfer Device (CSTD) of the present disclosure, has been produced for the safe transfer of potentially hazardous drugs used in the compounding of cancer treatments. The CSTD provides a means to make drug transfers between vials, syringes and IV bags without exposing the health care provider to the drug.

Early concepts for the CSTD included the possibility of applying the CSTD technology to an automated/robotic application. In this application, the CSTD, vials, syringes, etc. would be introduced to a standard pharmaceutical hood, then an automatic or semi-automatic preparation system would provide the motion, mixing, etc. required to develop a suitable drug for administration to a patient. The primary objective of such an approach would be the reliability, accuracy and repeatability afforded by an automated or semi-automated method. Further, the preparation system could be applied to multi-hood environments, improving throughput, and reducing the need for additional personnel, in particular physicians and pharmacologists to scrub and suit up.

Preparation System Design:

The preparation system 1000 includes a number of components that make up subsystems which integrate into the top level preparation system. This approach was conceived for two reasons; it allows the preparation system 1000 to be discretized for easier development, and in the production case it will allow for 'plug & play' operation for maintenance, repair and upgrade.

The subsystems of the preparation system 1000 include, as mentioned above, at least a motion controller and drives; a manipulator (M); component holders (CH); a carousel/frame (1100); a gripper (G); a rotation station (RS); a transfer station (TS); and a weigh station (WS).

The motion controller and drives is the overarching electronic controls system that ties each subsystem into the control system. In this case the motion controller is a Galil DMC4050. There are five servo axes that are centrally controlled and can operate independently of each other, each driven by a 500 W onboard amplifier. Additionally, the controller provides for additional digital and analog I/O for the control of solenoid valves, input signals, analog weight measurements, etc.

The manipulator (M) includes a three mutually orthogonal axis system based on integrated linear guide/ballscrew slides or rails 1110, 1112, 1114, in this case Accutech USA KM slides. Each of the slides is driven by a servo motor, with closed-loop encoder position feedback. Commutation of each motor is afforded by Hall sensors.

Figure 40B:
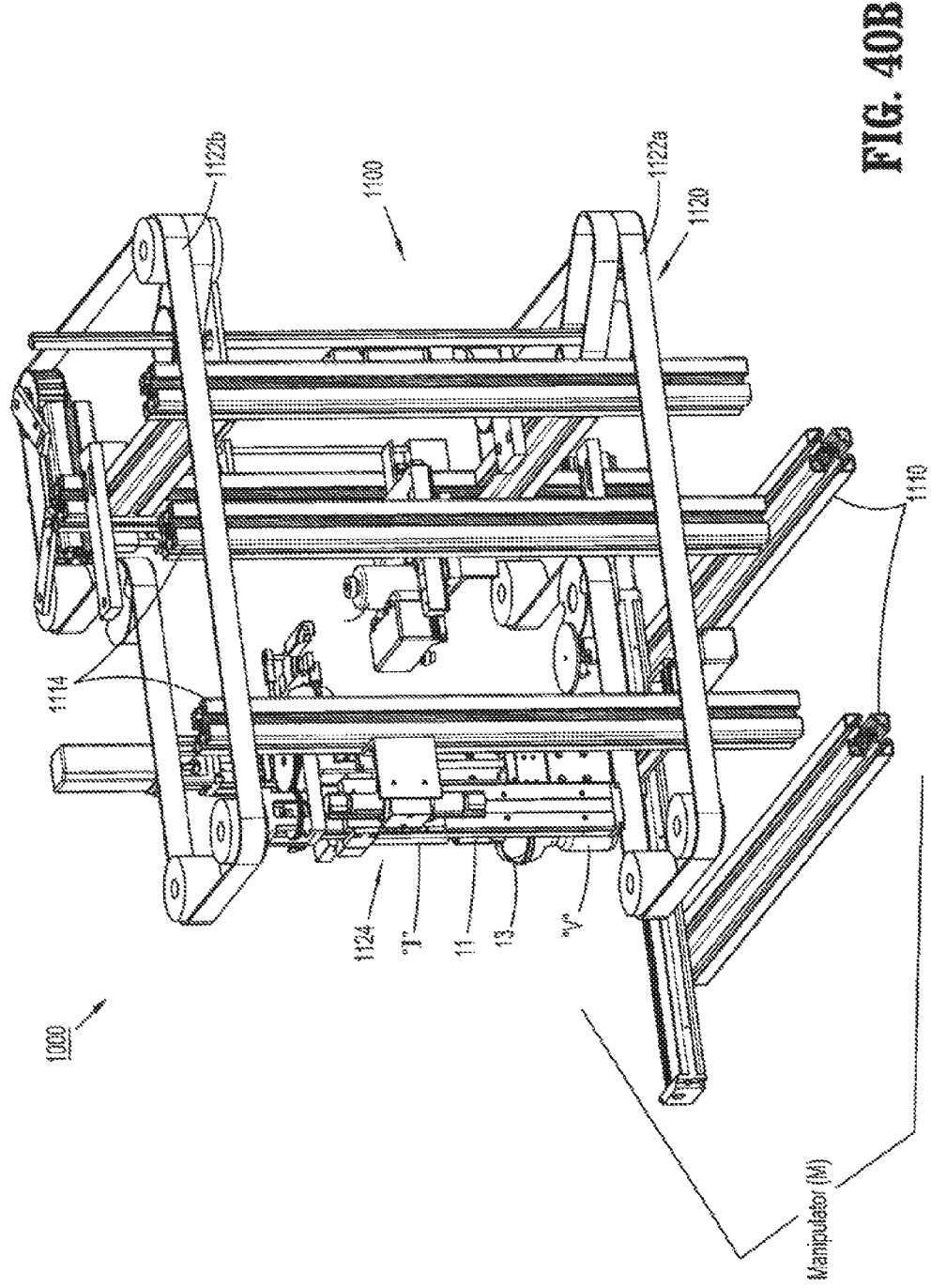
Figure 40D:
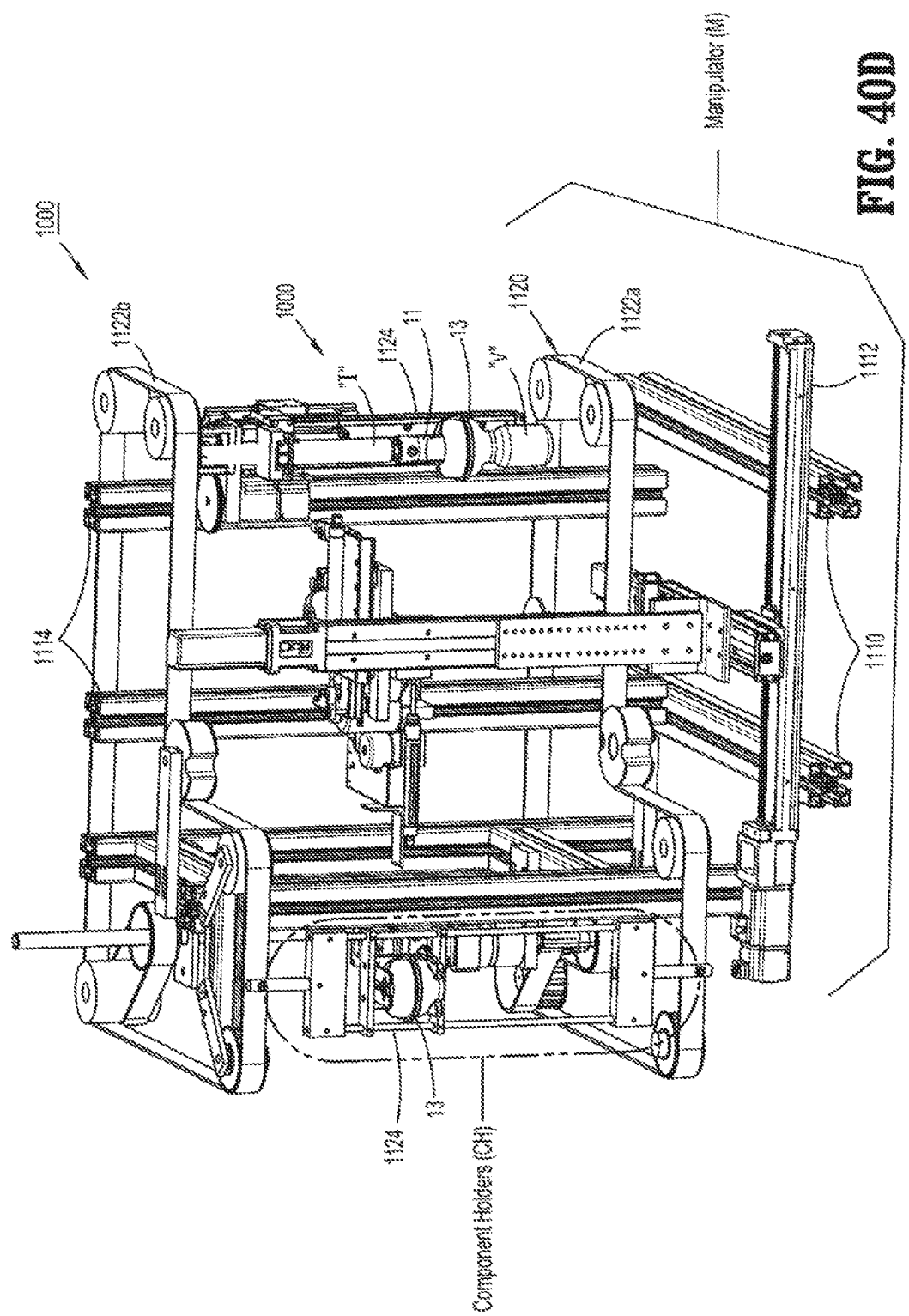

A carousel 1120 of the preparation system 1000 is responsible for the translation of the various compounding components, i.e. vials "V", syringes "I", vial adapters 13, and syringe adapters 11, from a loading position to a gripping position. The carousel 1120 is based on two horizontal axis gearbelts, one upper and one lower gearbelt 1122a, 1122b, respectively, that operate in concert. Each gearbelt 1122a, 1122b is movably supported on a series of sprockets and the like. At least one of the gearbelts 1122a, 1122b may be driven by a motor to move the gearbelts 1122a, 1122b, in the manner of a conveyor belt, around carousel 1120. In an embodiment, as seen in FIG. 40B, a motor may be used to drive a drive shaft 1126, which drive shaft 1126 drives a pair of driving belts, i.e., a first lower driving belt 1126a, and a second upper driving belt 1126b, wherein the driving belts 1126a, 1126b are operatively connected to respective gearbelts 1122a, 1122b via respective sprockets and the like.

Component holders 1124 are affixed to each gearbelt 1122a, 1122b and are positioned between them, and translate between them. In this manner, as the gearbelts 1122a, 1122b are moved around carousel 1120, component holders 1124 are moved around carousel 1120 to the various stations of preparation system 1000 (e.g., rotation station (RS), transfer station (TS) and/or weigh station (WS)).

The component holders 1124, positioned at intervals along the carousel belts or gearbelts 1122a, 1122b, provide locations for the user to introduce compounding components for subsequent pull and use by a gripper (G). Each of the component holders 1124 features a pair of jaws that are operated on by a meshed gearset and a torsion spring, so the two jaws will operate in coordination about the center plane, and provide sufficient engagement pressure to maintain a hold on the component until extraction by the gripper (G).

The gripper (G) is responsible for grasping a compounding component in the component holder 1124, removing it from one station or the component holder 1124, and then placing it in another station. The gripper (G) is also responsible for returning a component from a station to the component holder 1124. The gripper (G) is further responsible for effecting the assembly and disassembly of the sub-assemblies, specifically the vial (V) and vial adapter 13 sub-assembly, and the syringe "I" and syringe adapter 11 sub-assembly. With reference to FIG. 40G, the gripper (G) includes two jaws that can adapt to four components, by way of hermaphroditic jaws 1130 (including a first pair of fixed, opposed jaws 1132, and a second pair of translatable, opposed jaws 1134, wherein one jaw of the first pair of jaws 1132 is interposed between the second pair of jaws 1134, and wherein a second jaw of the second pair of jaws 1134 is interposed between the first pair of jaws 1132) thereof. The gripper (G) features jaws 1130 that are coordinated by way of two gear racks and a pinion so that the jaws always open and close on a fixed center plane.

As illustrated in FIG. 40G, the gripper (G) functions by translating the first pair of jaws 1132 and the second pair of jaws 1134 relative to one another to grip a component (e.g., a syringe "I", a vial "V", a syringe adapter 11, a vial adapter 13, etc.) in one of a first gripping position (G1), a second gripping position (G2) and a third gripping position (G3). The first gripping position (G1) may be located between the first jaw of the first pair of jaws 1132 and the first jaw of the second pair of jaws 1134; the second gripping position (G2) may be located between the second jaw of the first pair of jaws 1132 and the first jaw of the second pair of jaws 1134; and the third gripping position (G3) may be located between the second jaw of the first pair of jaws 1132 and the second jaw of the second pair of jaws 1134.

By way of example only, the first gripping position (G1) of gripper (G) may be used to grip a syringe "I", the second gripping position (G2) of gripper (G) may be used to grip a vial adapter 13, and the third gripping position (G3) of gripper (G) may be used to grip a syringe adapter 11.

A rotation station (RS) of the preparation system 1000 provides, as seen in FIG. 40E, a clamping feature 1140 for the assembly of sub-assemblies and, if desired or required, for the rotation and/or oscillation of the various sub-assemblies. A pneumatic actuator located beneath the station provides 360 degrees of rotation to one of the rollers 1142 of the clamping feature 1140. The rotation is used in the assembly of the syringe "I" and syringe adapter 11 by way of a Luer lock thread. Further the rotation station (RS) is used to rotate the vial "V" past a scanner (optical or otherwise) for identification of the vial "V" and its contents. The rotation station (RS) is also equipped with two gear racks and a pinion to maintain centrality to the center plane.

Figure 40F:
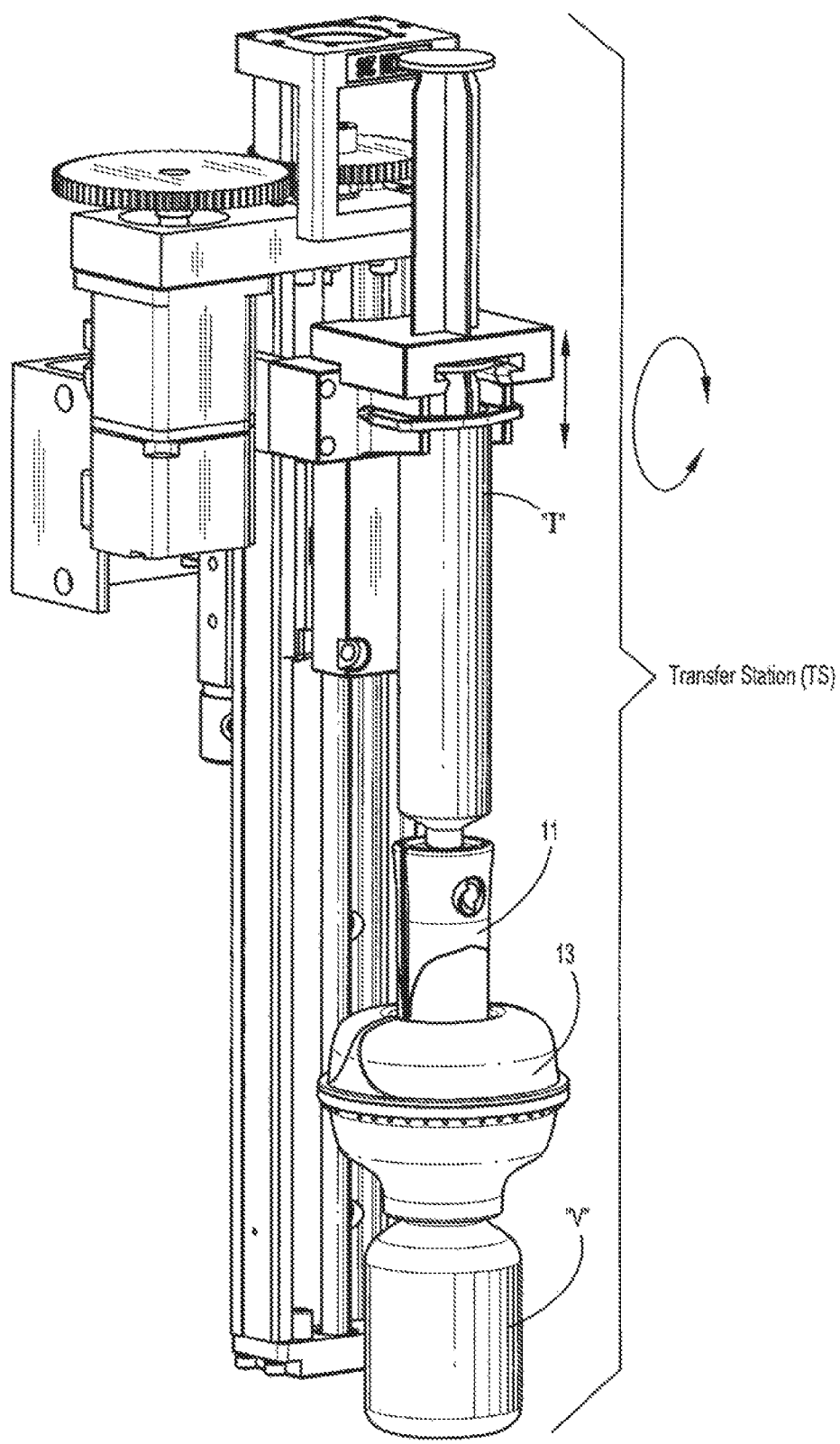
Figure 41A:
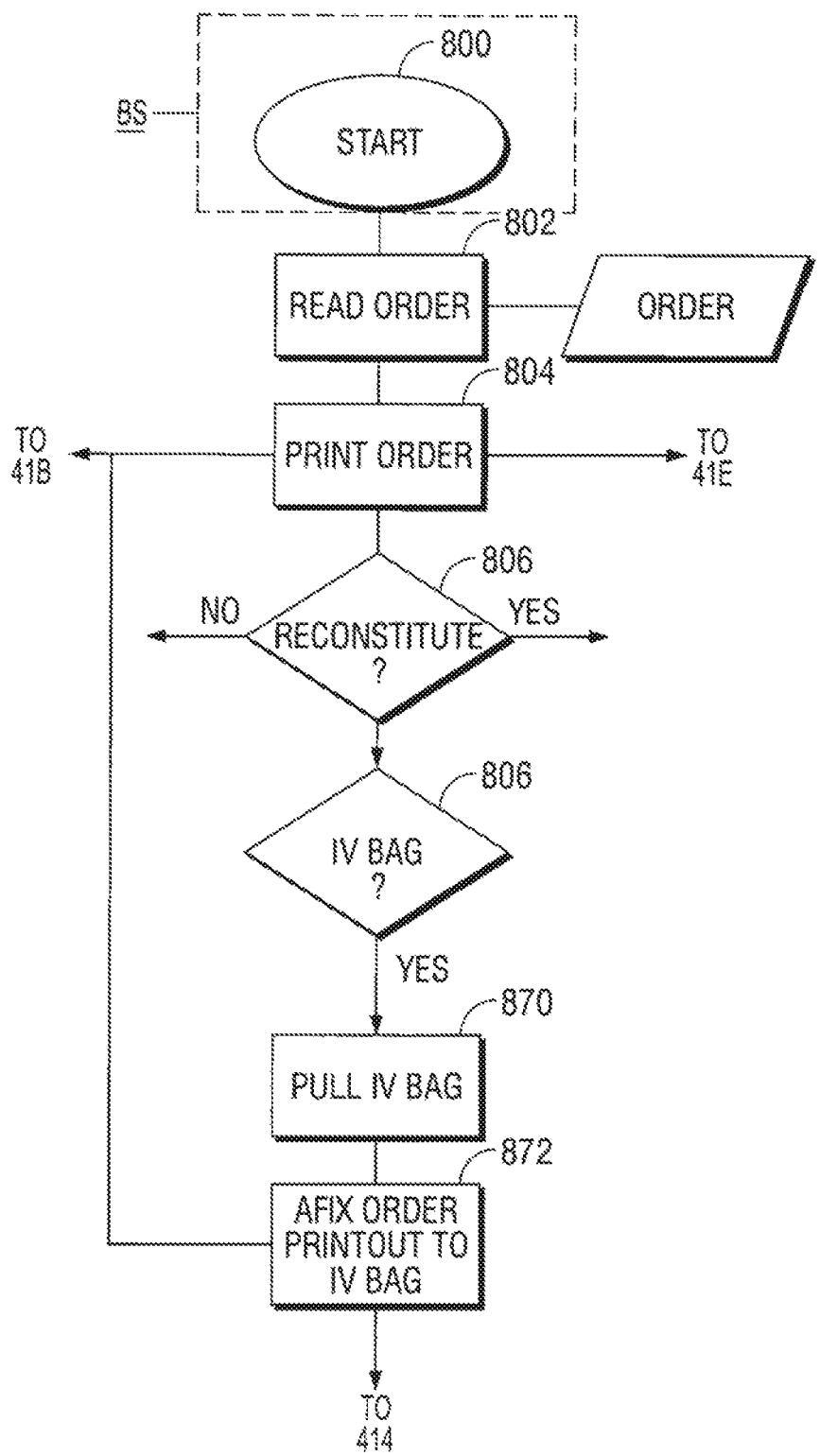
FIGS. 41A-41H is an annotated process flow diagram illustrating the method of use of FIGS. 38A-38H, of the automated system of FIGS. 26-37 together with a medicament transport system of the present disclosure, as accomplished with the various sub-systems and/or stations of the preparation system illustrated in FIGS. 40A-40G.
Figure 41B:
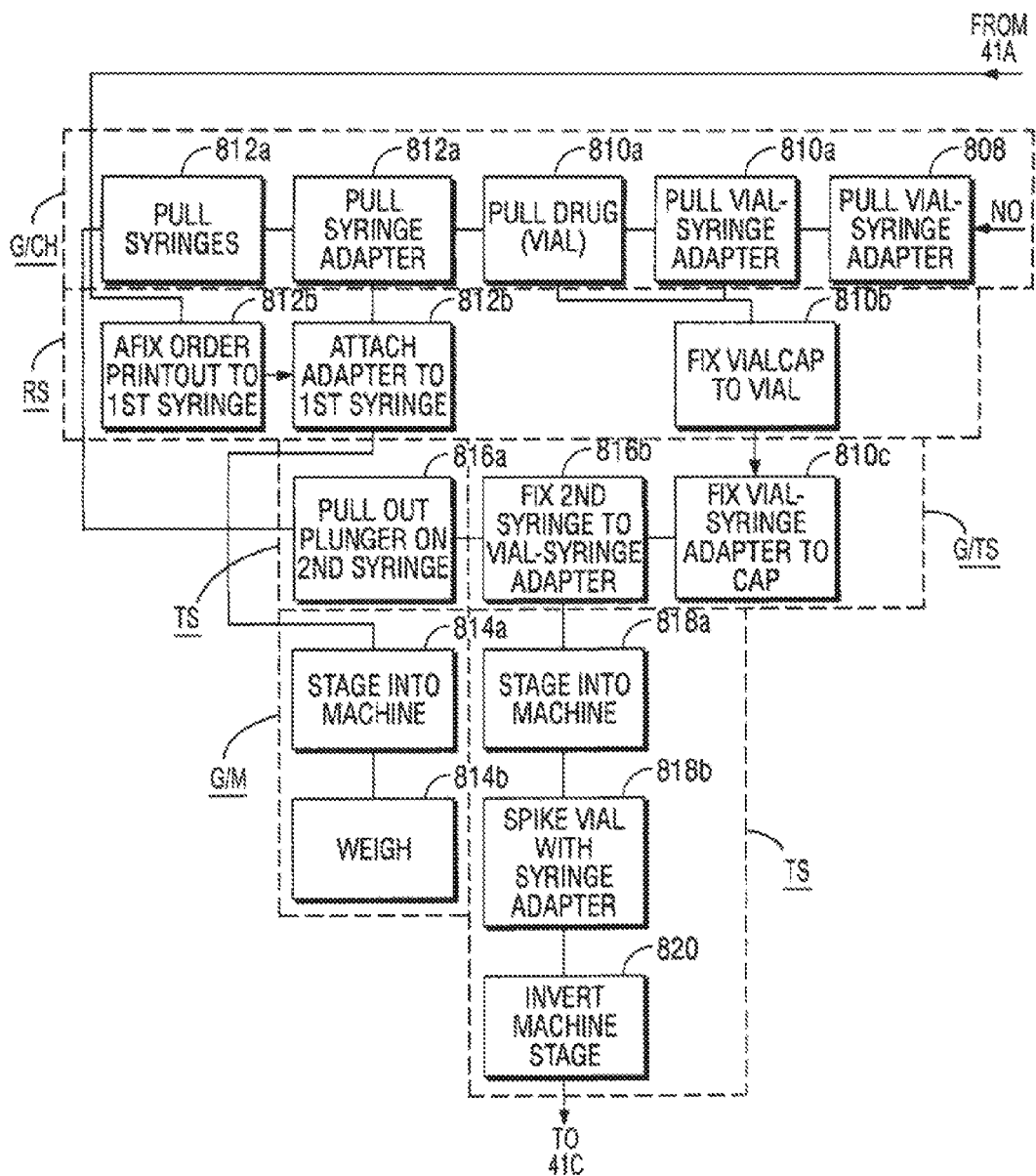
Figure 41C:
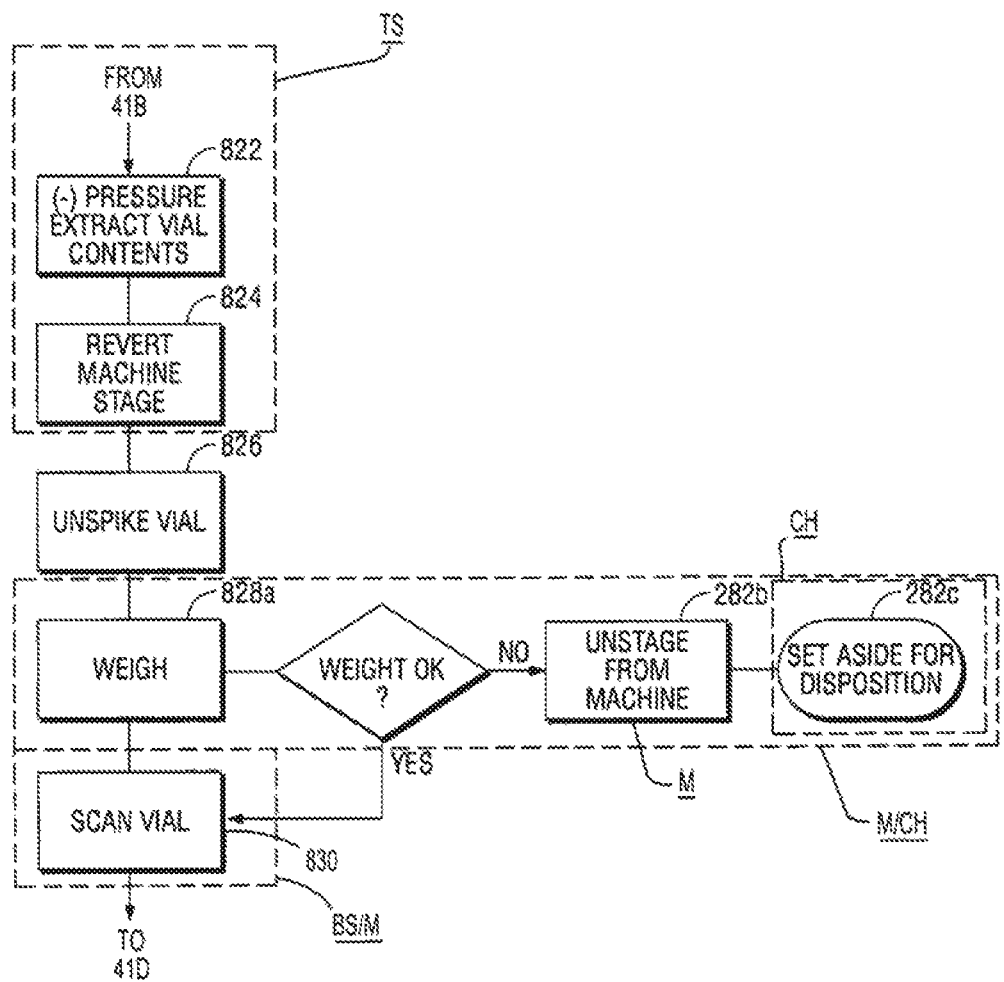
Figure 41D:
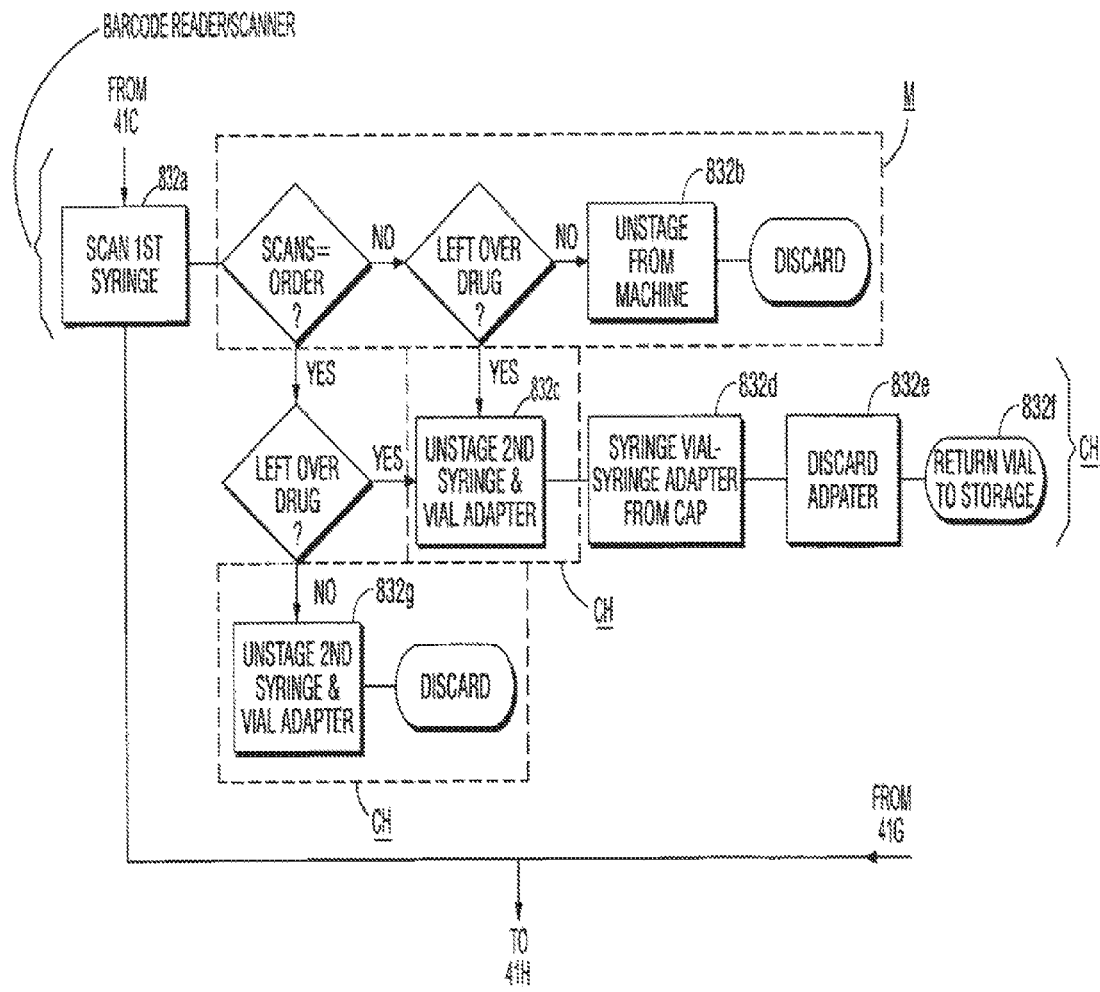
Figure 41E:
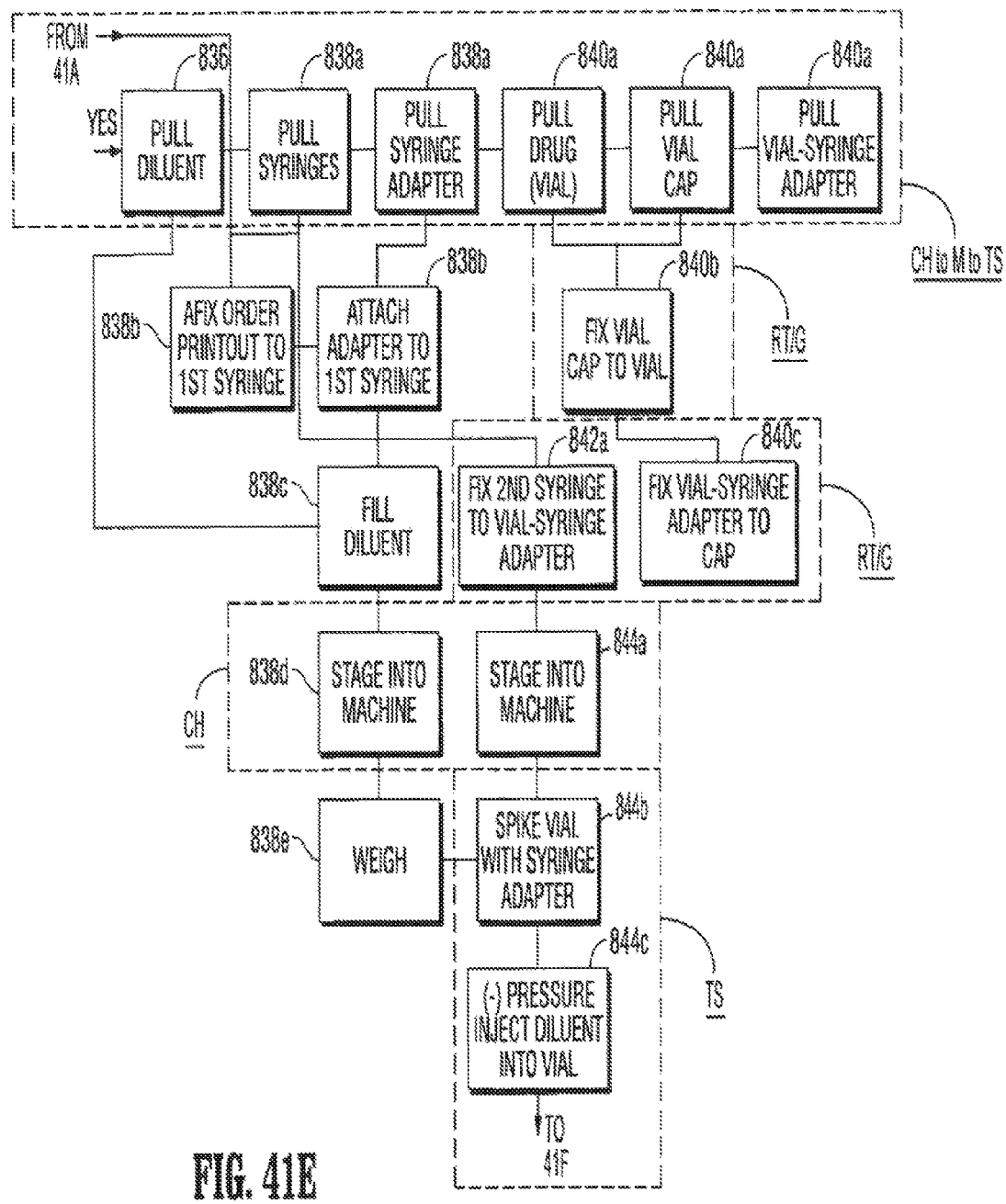
Figure 41F:
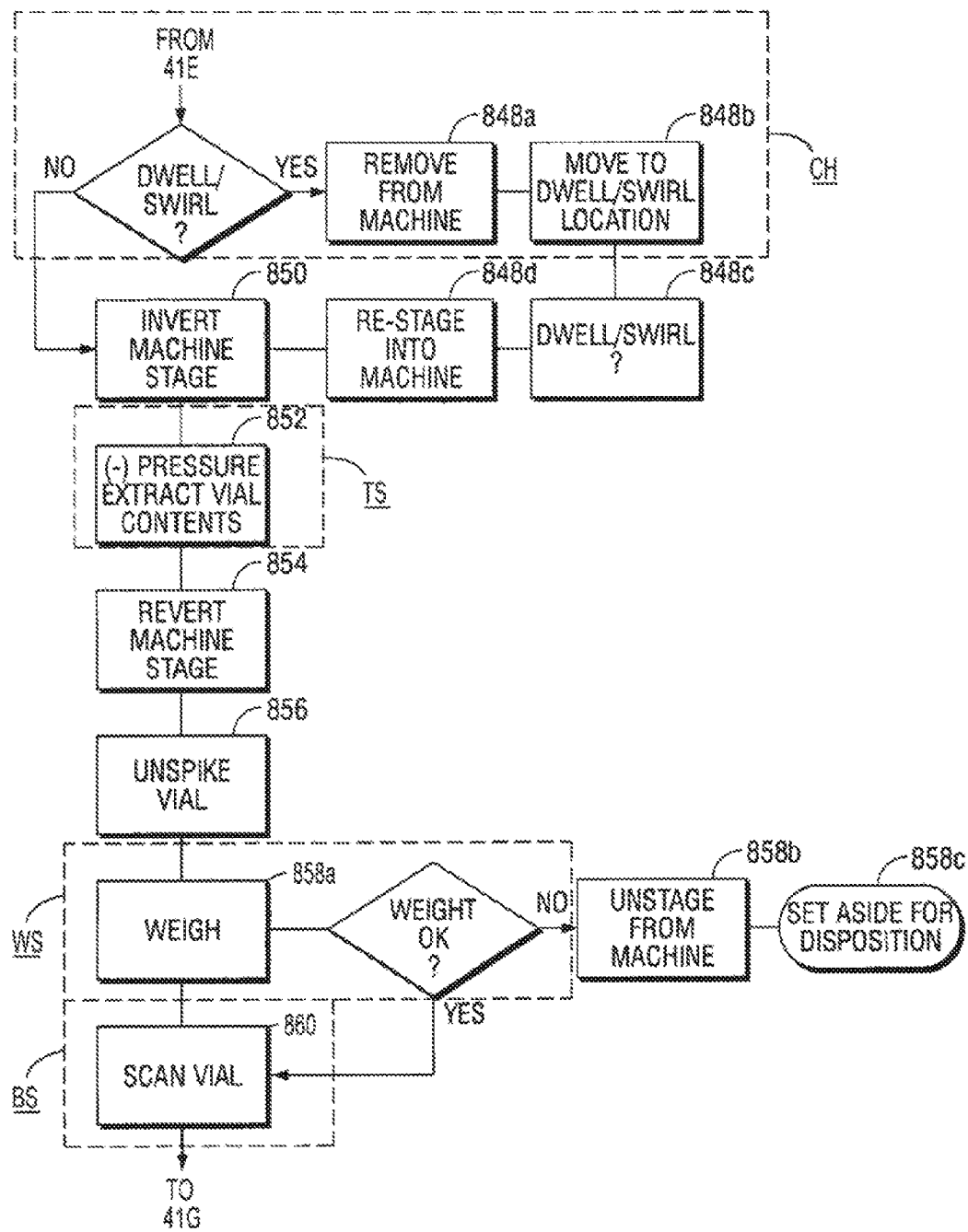
Figure 41G:
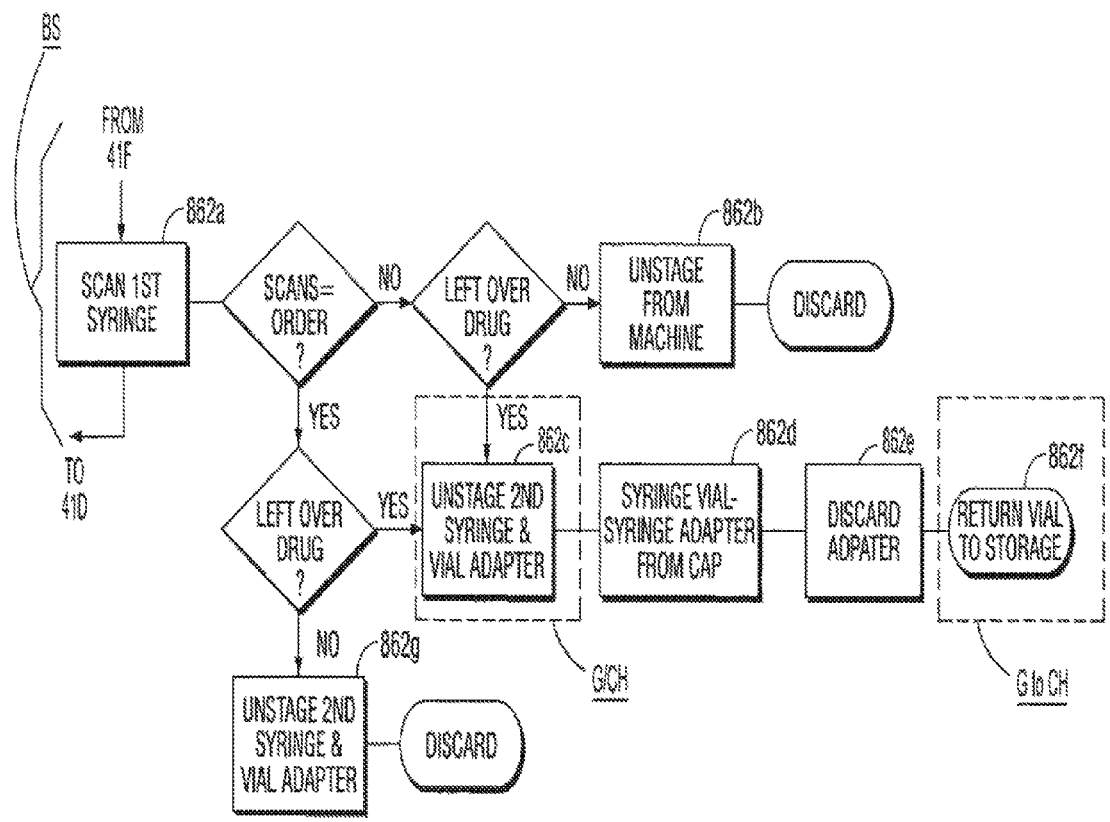
Figure 41H:
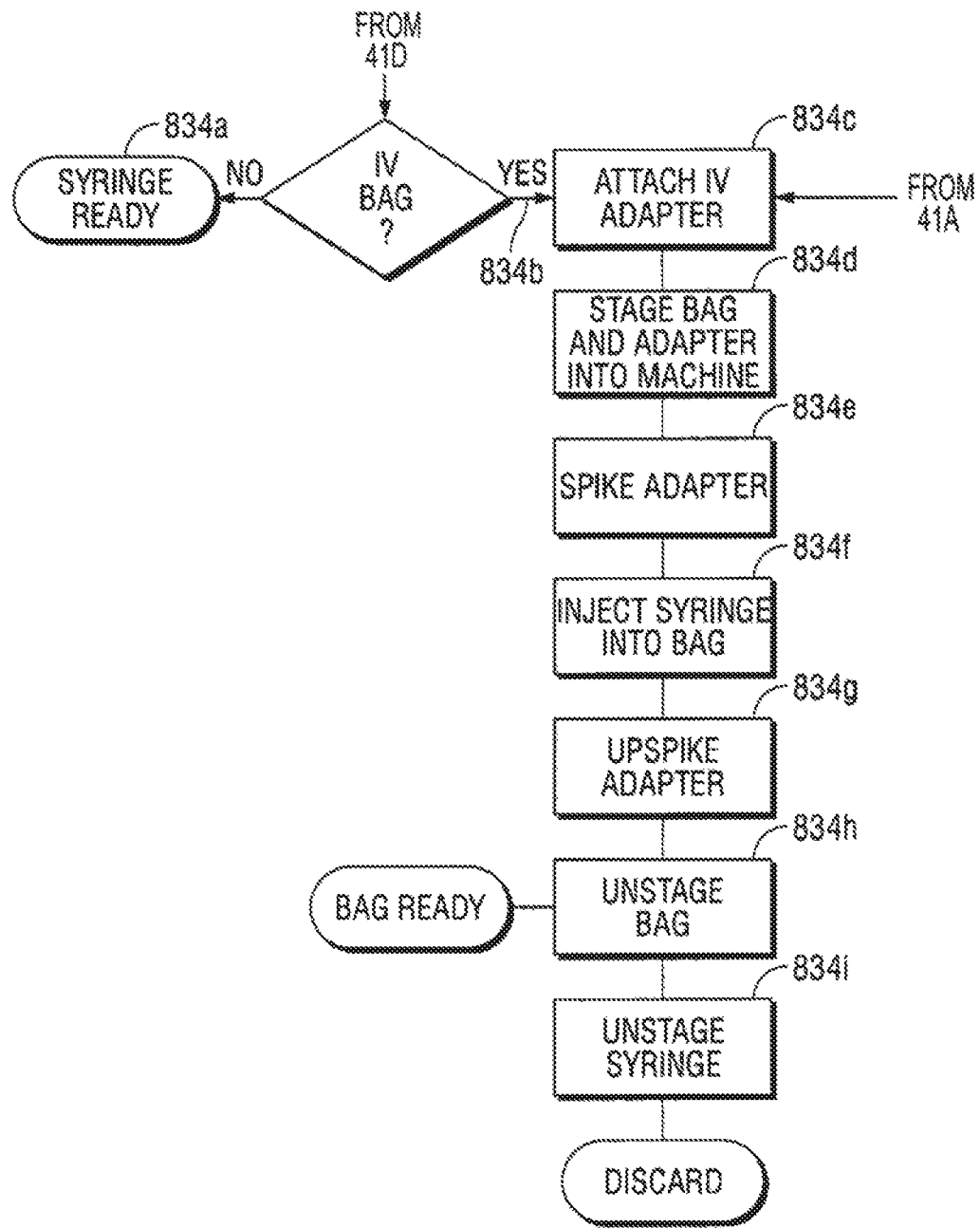
Figure 42A:
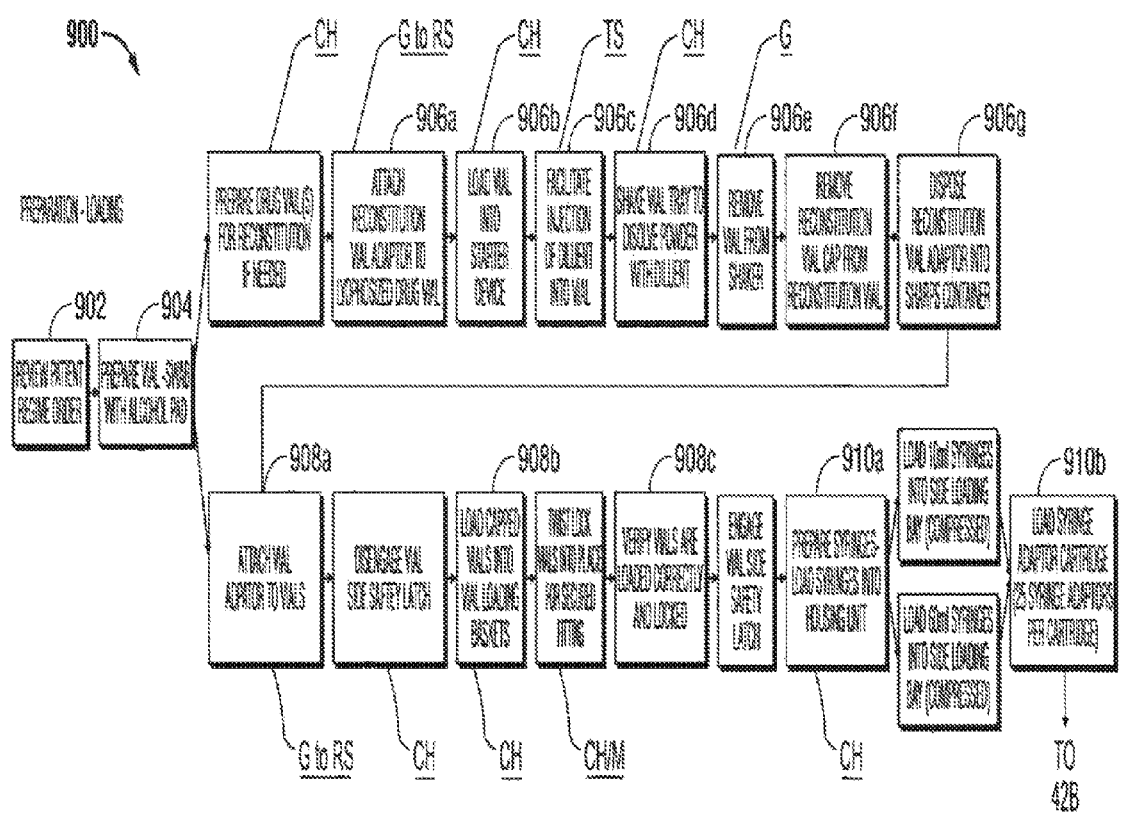
FIGS. 42A-42C is an annotated process flow diagram illustrating the further method of FIGS. 39A-39C, of the automated system of FIGS. 26-37 together with a medicament transport system of the present disclosure as accomplished with the various sub-systems and/or stations of the preparation system illustrated in FIGS. 40A-40G.
Figure 42B:
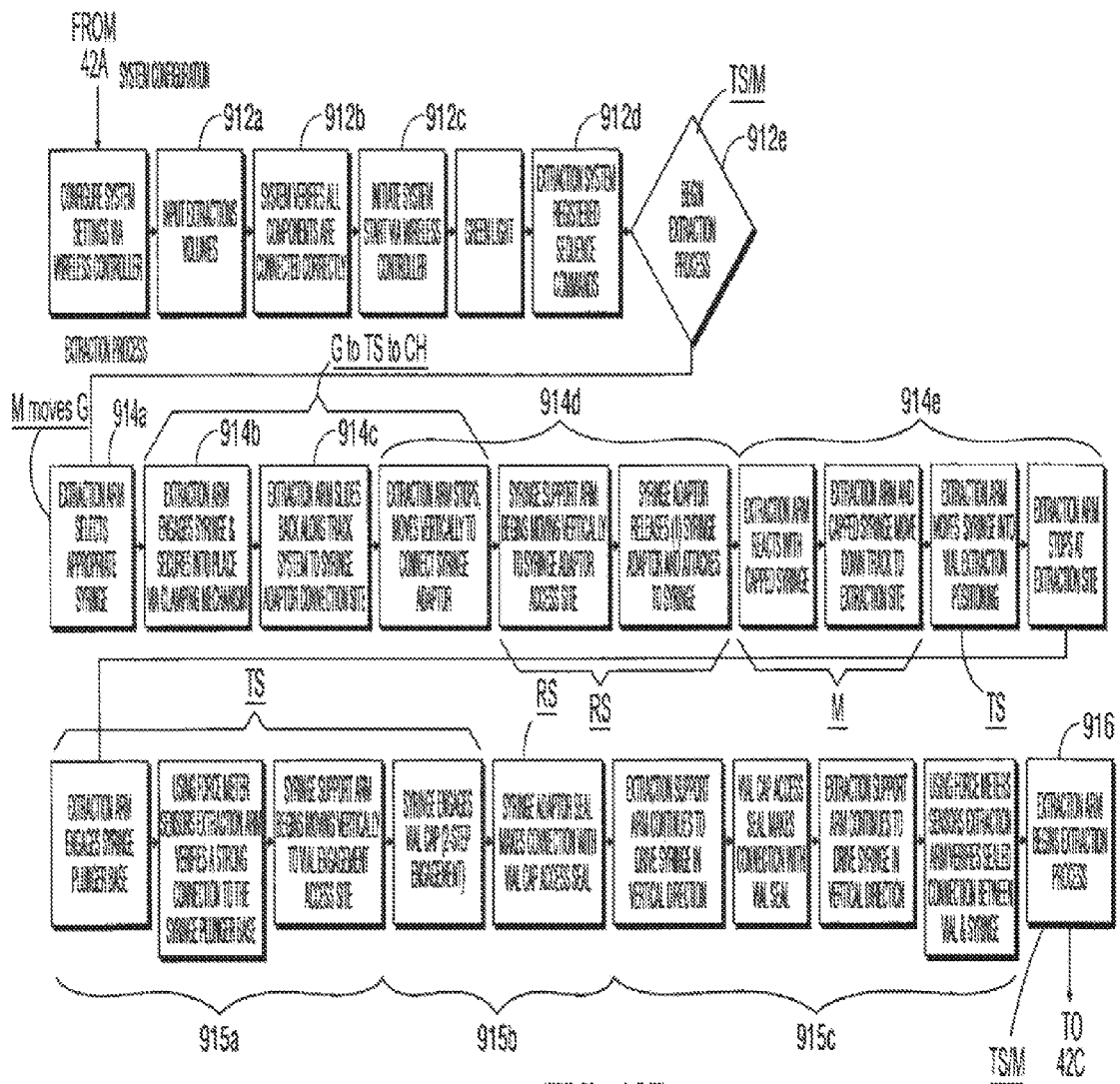
Figure 42C:
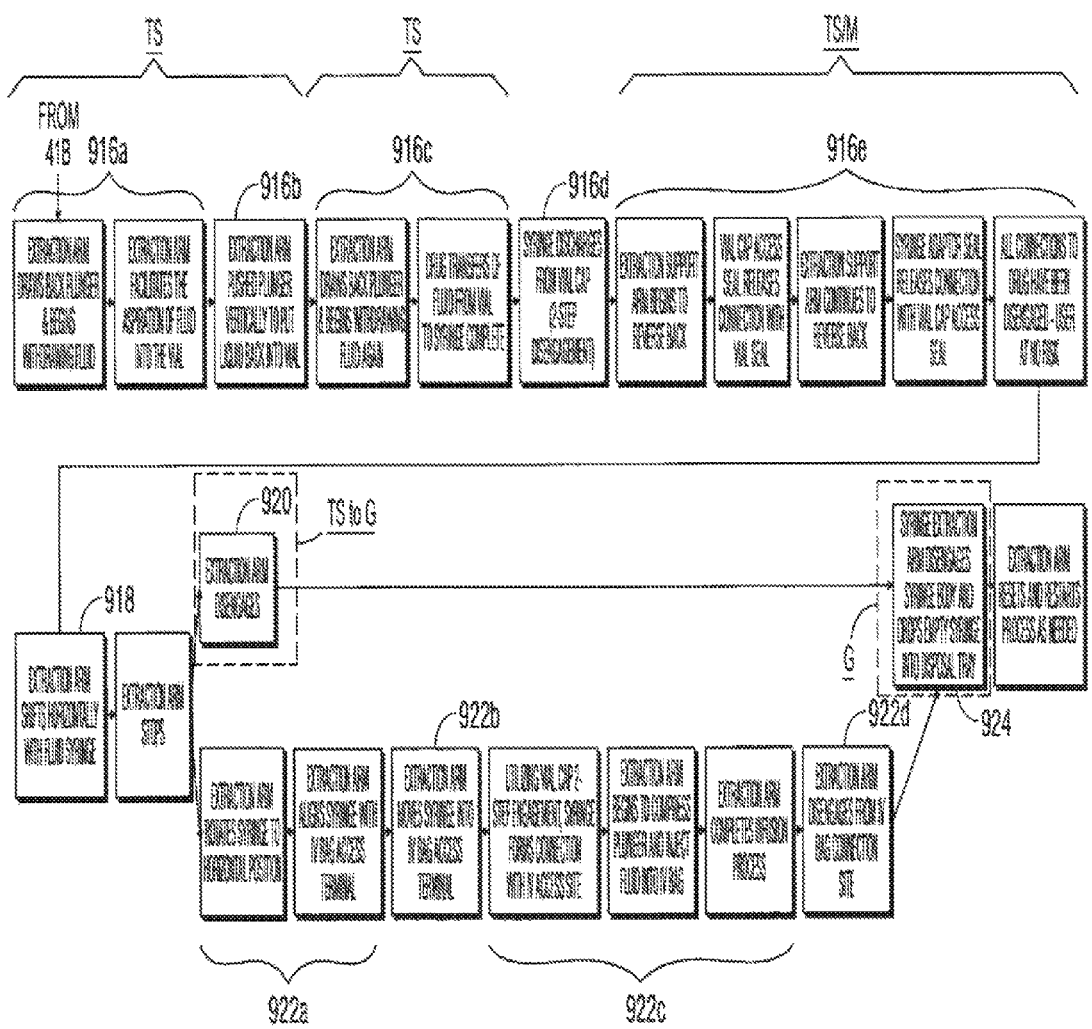

Fluid transfer is realized at a transfer station (TS) of the preparation system 1000. The transfer station (TS), as seen in FIG. 40F, is configured as a linear slide, similar to those in the manipulator (M), and is likewise driven by a closed loop servo motor controlled by the motion controller. Adapters are configured to provide axial displacement of a syringe plunger "IP" relative to a syringe body "IB" (FIG. 40F). In operation, prior to assembling a new or empty syringe "I" to the syringe adapter 11, the transfer station (TS) draws a prefill of air. Once the compounding assembly (syringe, syringe adapter, vial adapter and vial) is placed in the transfer station (TS) the prefilled air is pushed into the vial adapter 13, the entire transfer station (TS) is inverted, and the drug (contained in the vial "V") is drawn into the syringe "I" from the vial "V".

Operation:

The operation of the preparation system 1000 relies upon a number of independent sub-routines. The preparation system 1000 is capable of executing a transfer of fluid "L" (i.e., drug, etc.) from a vial "V" to a syringe "I", utilizing one each of a syringe "I", a syringe adapter 11, a vial "V" and a vial adapter 13. The program flow follows in Table 1 below.

TABLE 1 basic program and function

| SEQUENCE NO. | SUBROUTINE | FUNCTION |
|---|---|---|
| 1 | VARIABL | SETS POSITIONS, SPEEDS, ETC. |
| 2 | INITIAL | ZEROES B, C, D, E |
| 3 | VPICK | GRABS VIAL |

TABLE 1-continued basic program and function

| SEQUENCE NO. | SUBROUTINE | FUNCTION |
| --- | --- | --- |
| 4 | VPLACE | PLACES VIAL INTO ROTATION STATION |
| 5 | VAPICK | GRABS VIAL ADAPTER |
| 6 | VSUB | MAKES VIAL AND VIAL ADAPTER SUB-ASSEMBLY (VIAL SUB) BY FLUIDLY CONNECTING (BY ROTATION) VIAL ADAPTER AND VIAL |
| 7 | WEIGH | MOVES VIAL SUB TO WEIGH STATION, WEIGHS VIAL SUB, MESSAGES MASS |
| 8 | VSUBPLC | PLACES VIAL SUB BACK INTO VIAL ADAPTER HOLDER |
| 9 | SAPICK | GRABS SYRINGE ADAPTER |
| 10 | SAPLACE | PLACES SYRINGE ADAPTER INTO ROTATION STATION |
| 11 | SPICK | GRABS SYRINGE |
| 12 | TRAN | MOVES SYRINGE TO TRANSFER STATION |
| 13 | PREFILL | RETRACTS PLUNGER OF SYRINGE BY A PRESET VOLUME |
| 14 | SPLACE | GRABS SYRINGE FROM TRANSFER STATION, MOVES TO ROTATION STATION AND MAKES SYRINGE AND SYRINGE ADAPTER SUB-ASSEMBLY (SYRINGE SUB) BY FLUIDLY CONNECTING SYRINGE (BY ROTATION) TO SYRINGE ADAPTER |
| 15 | SSTORE | PLACES SYRINGE SUB INTO SYRINGE HOLDER |
| 16 | VAPICK | GRABS VIAL SUB |
| 17 | VSUBROT | RETURNS VIAL SUB TO ROTATION STATION |
| 18 | SPICK | GRABS SYRINGE SUB |
| 19 | ASSEMBL | ASSEMBLES SYRINGE SUB TO VIAL SUB |
| 20 | TRAN | MOVES SYRINGE SUB TO TRANSFER STATION |
| 21 | FLUIDX | PUSHES AIR INTO VIAL ADAPTER, INVERTS, RETRACTS FLUID INTO SYRINGE, REVERTS |
| 22 | DISASS | DISASSEMBLES VIAL SUB AND SYRINGE SUB ASSEMBLIES |
| 23 | SSTORE | PLACES SYRINGE SUB INTO SYRINGE HOLDER |

This sequence entails initializing the preparation system 1000, assembling the vial "V" and vial adapter 13, prefilling the syringe "I", assembling the syringe adapter 11 to the syringe "I", assembling the syringe sub to the vial sub, injecting the prefill air into the vial adapter 13 and drawing the prescribed volume of fluid from the vial "V".

In addition to the demonstration of feasibility of manipulating compounding components, the preparation system 1000 is capable of a relatively high degree of accuracy and repeatability in the transfer of fluids to and from the syringe "I" and vial "V". A test comprised of the steps described in Table 2 (below) was performed to evaluate the accuracy and repeatability of the preparation system.

TABLE 2 testing protocol for volumetric transfer accuracy and repeatability

| Step | Action |
| --- | --- |
| 1 | make up vial sub |
| 2 | weigh vial sub |
| 3 | record weight |
| 4 | introduce syringe to transfer station |
| 5 | prefill air |
| 6 | remove from transfer station |
| 7 | make up syringe sub |
| 8 | make up assembly (syringe sub to vial sub) |
| 9 | introduce to transfer station |
| 10 | push prefill air into vial sub |
| 11 | invert |

TABLE 2-continued testing protocol for volumetric transfer accuracy and repeatability

| Step | Action |
| --- | --- |
| 12 | draw fluid from vial |
| 13 | revert |
| 14 | remove from transfer station |
| 15 | break down assembly |
| 16 | weigh vial sub |
| 17 | record weight |
| 18 | empty syringe into graduated cylinder |
| 19 | verify volume |

This test sequence was performed 6 times for 3 different volumes; 10, 15 and 20 ml. The results are summarized in Table 3.

TABLE 3

Volumetric transfer test results

| Specimen | Actual volume |
| --- | --- |
| Commanded volume: 10 | |
| 1 | 9.3 |
| 2 | 9.4 |
| 3 | 9.4 |
| 4 | 9.3 |
| 5 | 9.4 |
| 6 | 9.7 |
| average | 9.32 |

TABLE 3-continued

Volumetric transfer test results

| Specimen | Actual volume |
|---|---|
| std dev | 0.05 |
| accuracy | 0.93 |
| repeatability | 0.99 |
| Commanded volume: 15 | |
| 1 | 9.2 |
| 2 | 9.3 |
| 3 | 9.3 |
| 4 | 9.2 |
| 5 | 9.3 |
| 6 | 9.6 |
| average | 9.29 |
| std dev | 0.05 |
| accuracy | 0.62 |
| repeatability | 1.00 |
| Commanded volume: 20 | |
| 1 | 18.9 |
| 2 | 19.1 |
| 3 | 19.1 |
| 4 | 18.9 |
| 5 | 19.2 |
| 6 | 18.8 |
| average | 19.02 |
| std dev | 0.15 |
| accuracy | 0.95 |
| repeatability | 0.99 |

For the purposes of this study, the accuracy is represented the difference of average reading to commanded volume, and the repeatability is represented by the standard deviation divided by the commanded volume.

The preparation system 1000 demonstrates the basic feasibility of manipulating a set of CSTD's as well as vials "V" and syringes "I". The preparation system 1000 performed these tasks autonomously and can be operated semi-autonomously.

The preparation system 1000 further demonstrates very good accuracy and repeatability for the first pass assembly. Note especially the repeatability figures, which are in the 99% range. The repeatability is the more important of the two measurements, as calibration can bring the average (accuracy) into range, while maintaining the high level of precision.

Figure 38A:
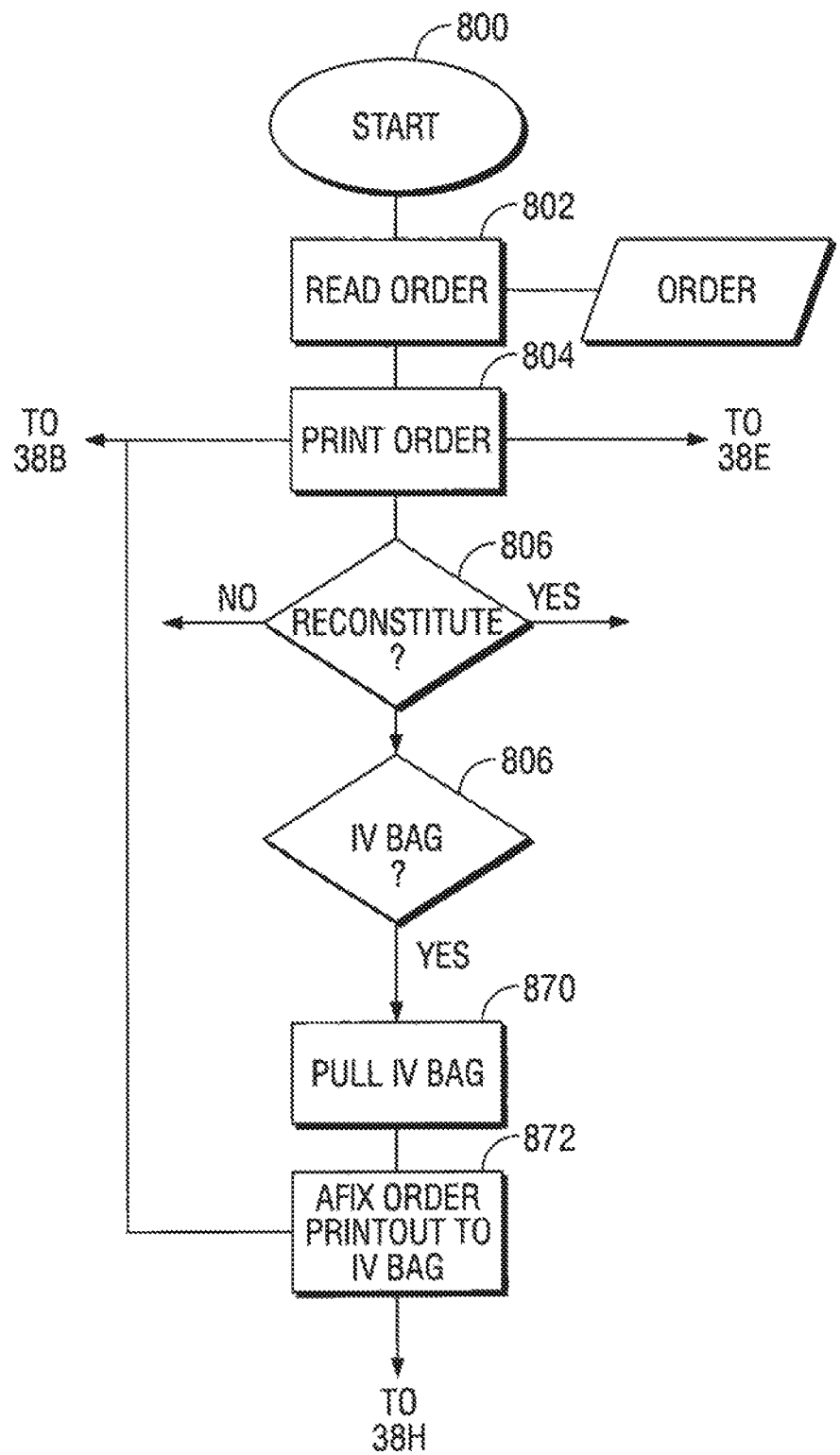
FIGS. 38A-38H is a process flow diagram illustrating a method of use of the automated system of FIGS. 26-37 together with a medicament transport system of the present disclosure.

With reference to FIGS. 38A-38H, a process of operating automated preparation system 1000, in accordance with the principles of the present disclosure, is provided. As seen in FIG. 38A, at step 800, the process is initiated. At Step 802, an order is read by preparation system 1000, and at Step 804, an order is printed. At Step 806, it is determined if the order requires a medicament to be reconstituted or if the order is to be used in an IV bag "B". Reconstitution may be achieved by rocking, agitating and the like of the vial "V" following addition of diluents thereto.

Figure 38B:
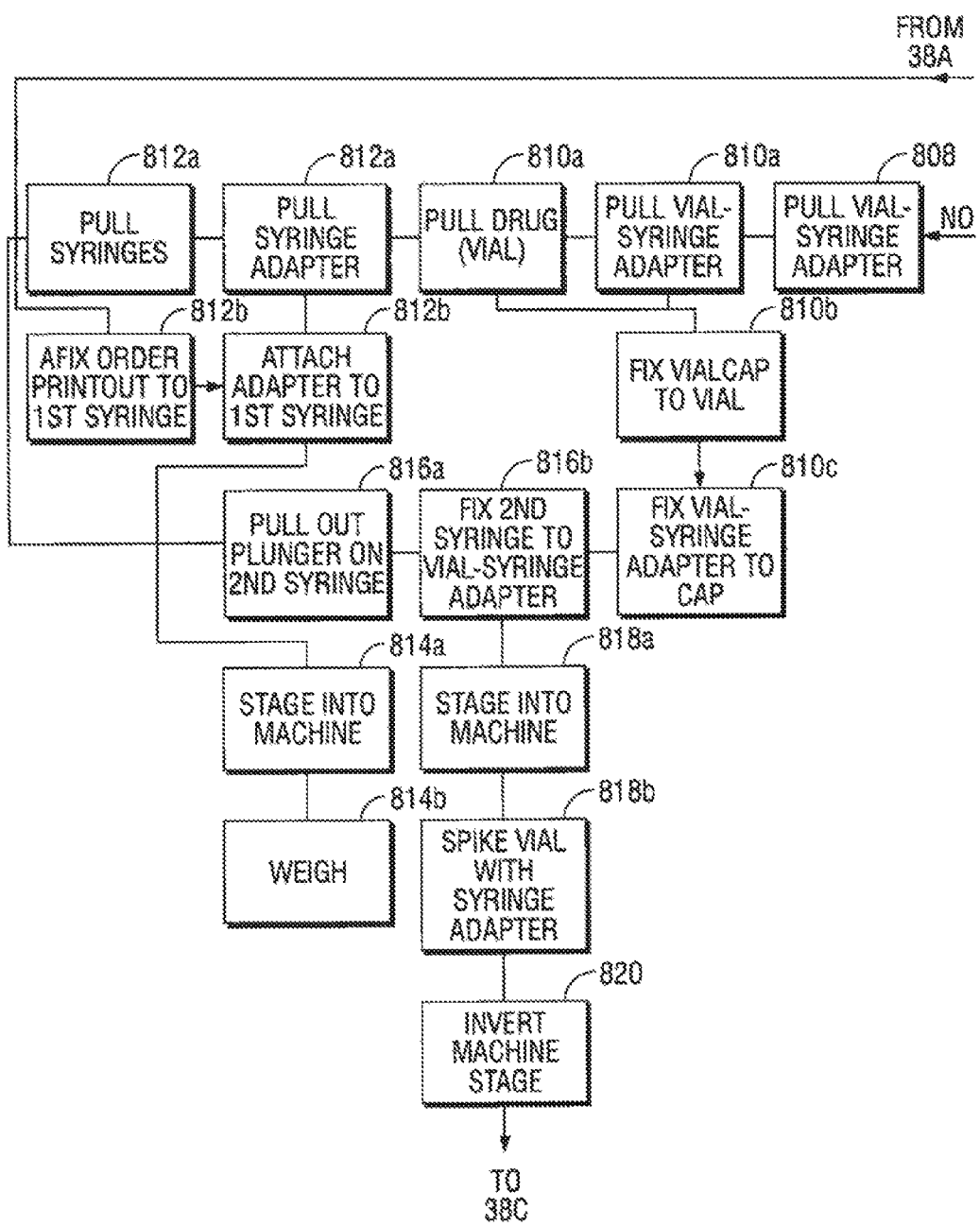

If the order does not require reconstitution, then, as seen in FIG. 38B, at Step 808 a vial-syringe adapter is pulled. At Step 810a, a vial "V" containing the medicament is pulled and a vial cap assembly is pulled. At Step 810b, the vial cap assembly is affixed to the vial "V". At Step 810c, the vial-syringe adapter in connected to the vial cap assembly. At Step 812a, a first and a second syringe are pulled and a first syringe adapter is pulled. At Step 812b, the order printed at Step 804 is affixed to the first syringe, and the first syringe adapter is attached to the first syringe. At Step 814a, the first syringe is staged in the carousel 1100 of preparation system 1000 and at Step 814b, the first syringe is weighed (for example, in weigh station (WS)). At Step 816a, a plunger of the second syringe is pulled out, and at Step 816b, the second syringe is connected to vial-syringe adapter that was pulled at Step 808. At Step 818a, the second syringe is staged in the carousel 1100 of preparation system 1000, and at Step 818b, the vial "V" is spiked by the vial-syringe adapter. At Step 820, the first syringe, the second syringe and the vial "V" are inverted.

Figure 38C:
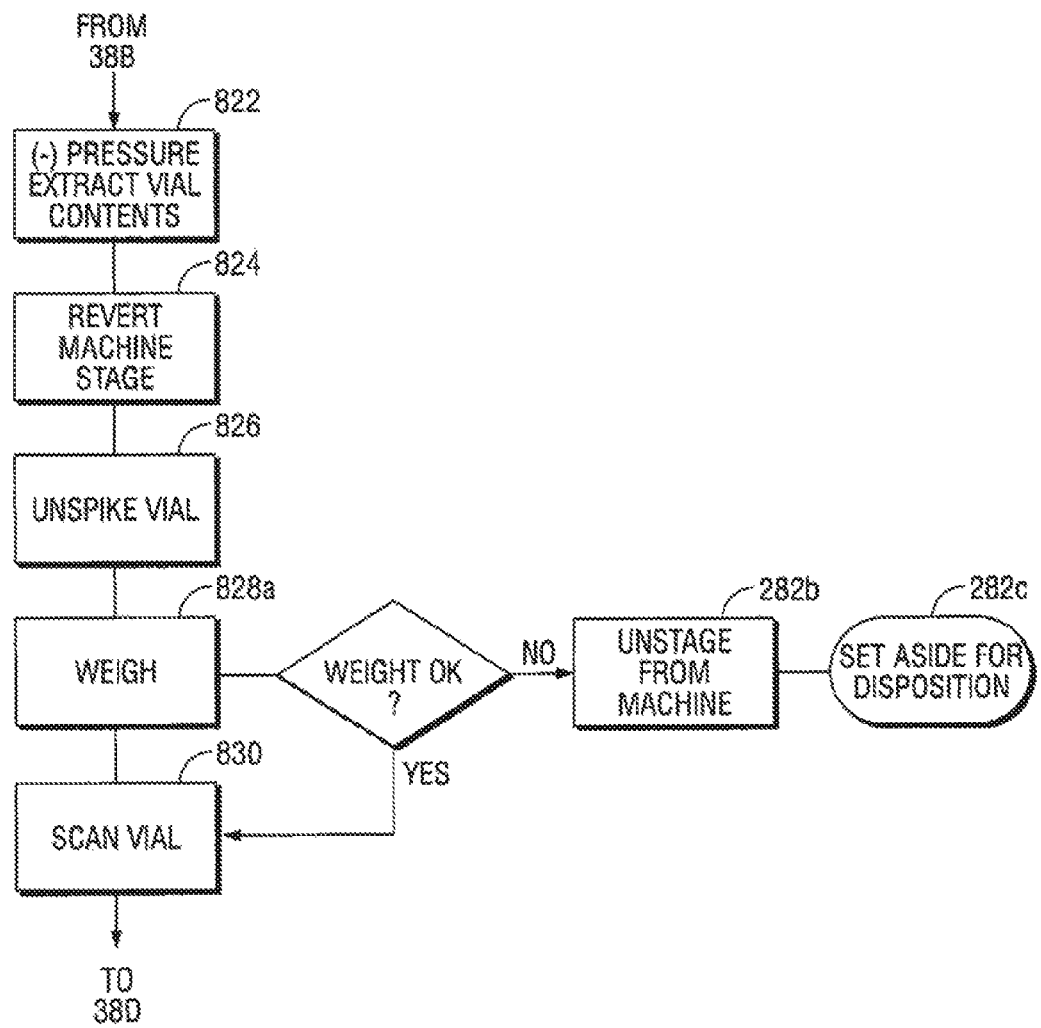

As seen in FIG. 38C, at Step 822 a negative pressure or vacuum is applied to the vial "V" to extract contents from the vial "V" (e.g., medicament). At Step 824, the first syringe, the second syringe and the vial "V" are reverted. At Step 826, the vial "V" is unspiked. At Step 828a, the vial "V" is weighed. If the weight of the vial "V" is not correct or not equal to an expected weight, at Step 828b, the vial "V" is unstaged from the carousel 1100 of preparation system 1000, and at Step 828c, the vial "V" is set aside for disposition. If the weight of the vial "V" is correct or is equal to an expected weight, than at Step 830, the vial "V" is scanned.

Figure 38D:
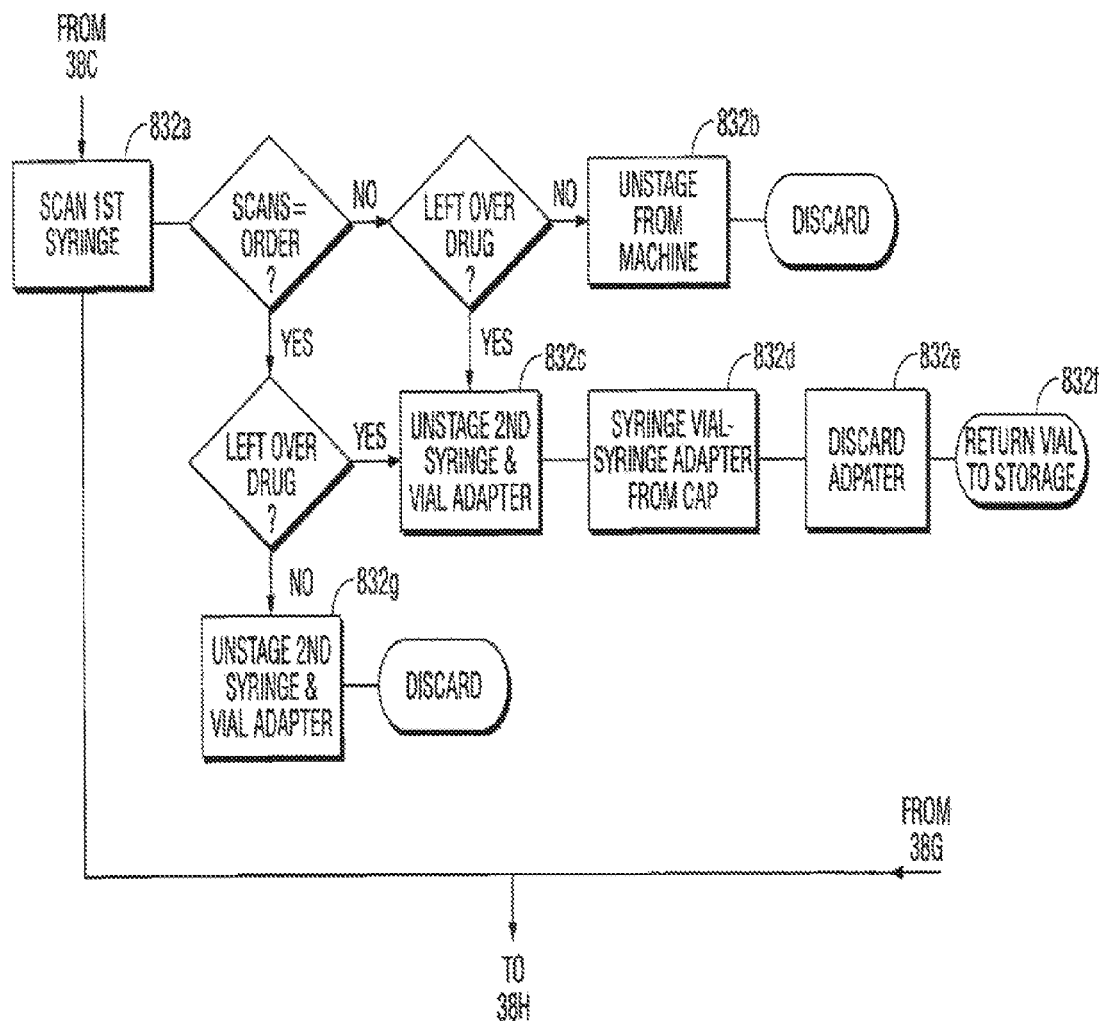

As seen in FIG. 38D, at Step 832a, the first syringe is scanned. If the information from the scan does not equal the information of the order and if there is no remaining drug, then at Step 832b, the first syringe is unstaged from the carousel 1100 of the preparation system 1000 and discarded. If the information from the scan does not equal the information of the order and if there is drug remaining, then at Step 832c, the second syringe and the vial-syringe adapter are unstaged from the carousel 1100 of the preparation system 1000. Then, at Step 832d, the vial-syringe adapter is separated from the cap, at Step 832e, the vial-syringe adapter is discarded and, at Step 832f, the vial "V" is returned to storage. If the information from the scan does equal the information of the order and if there is drug remaining, then Steps 832c-832f are once again performed. If the information from the scan does equal the information of the order and if there is no drug remaining, then at Step 832g, the second syringe and the vial-syringe adapter are unstaged and discarded.

Figure 38E:
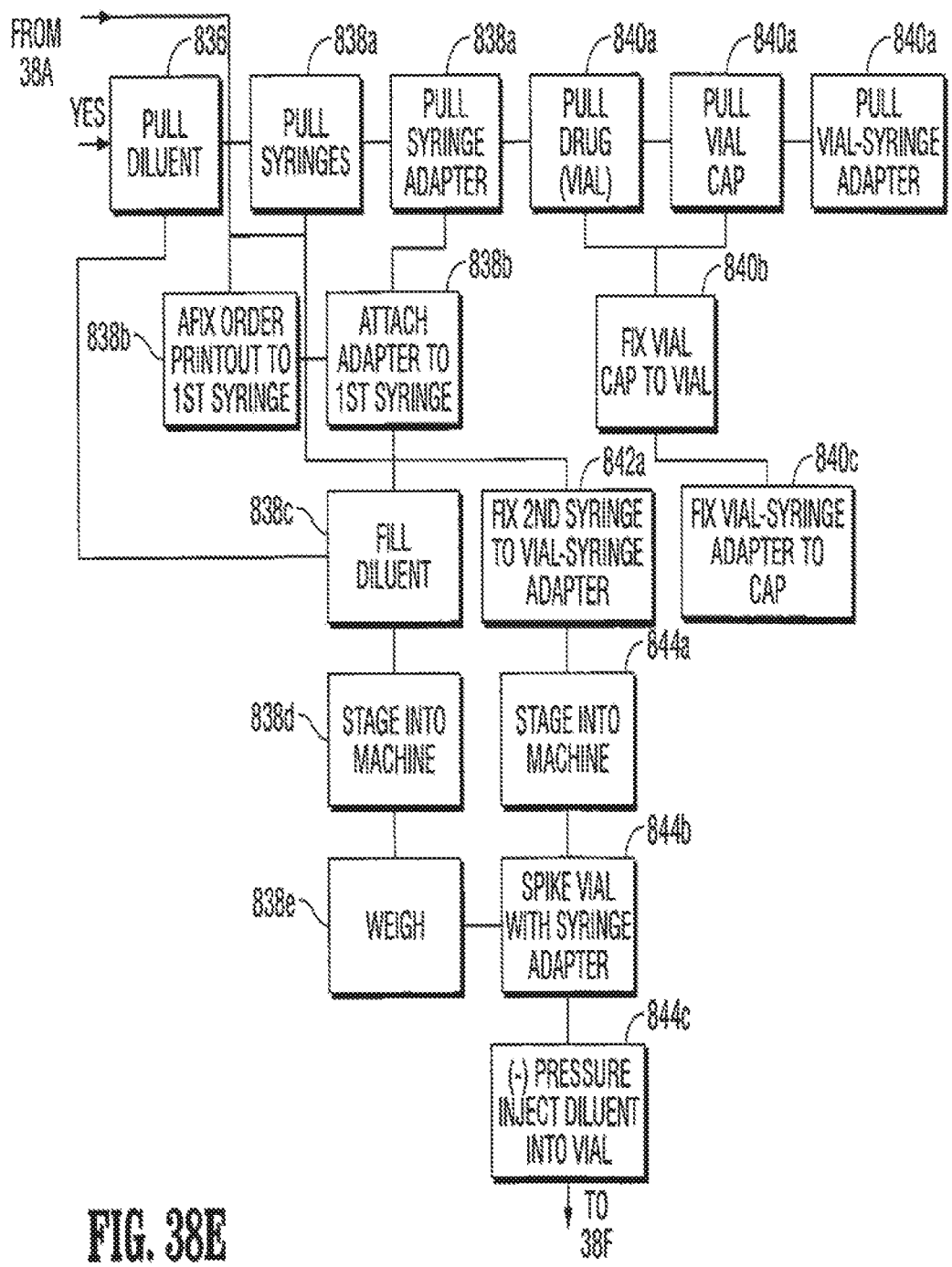
Figure 38F:
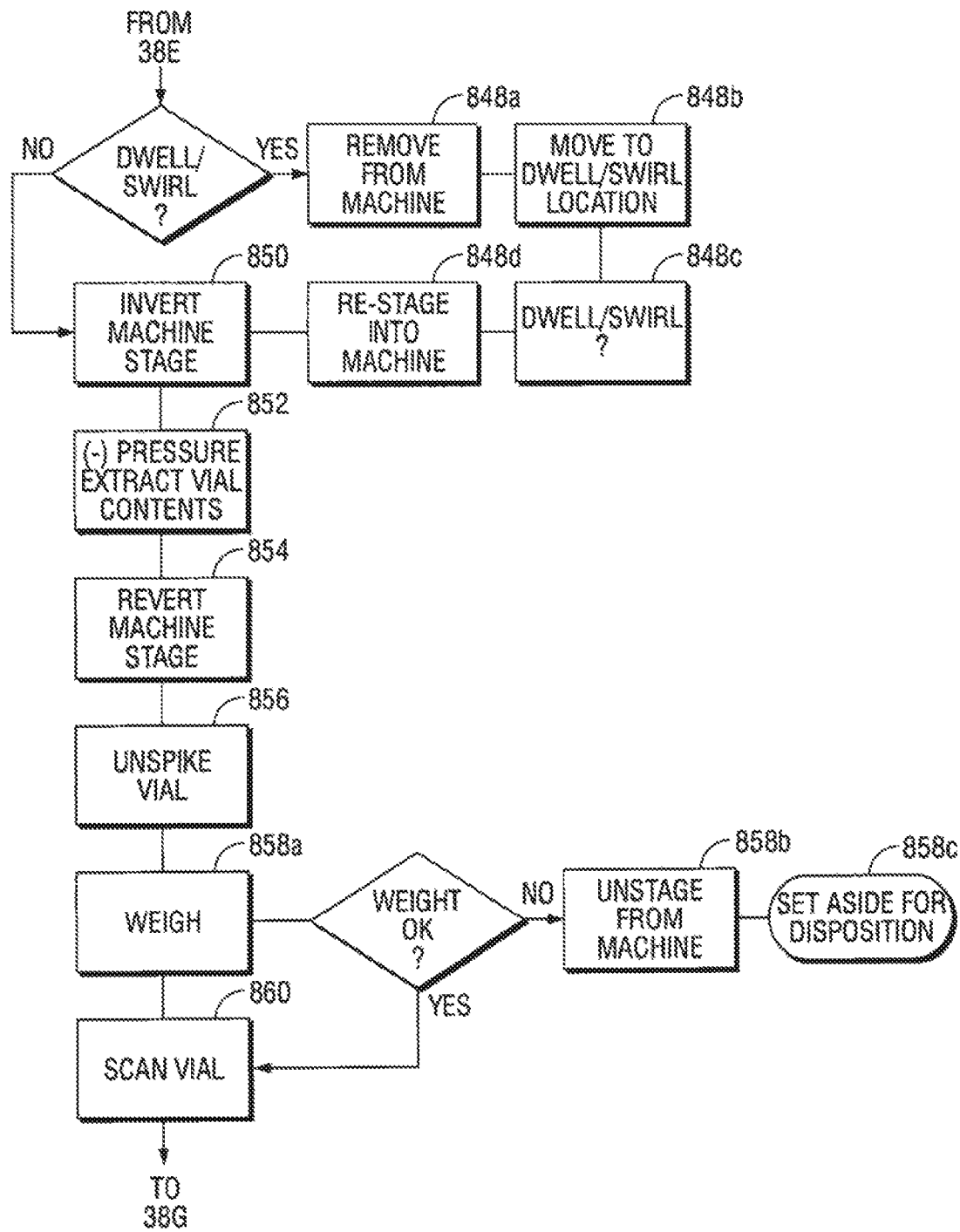
Figure 38G:
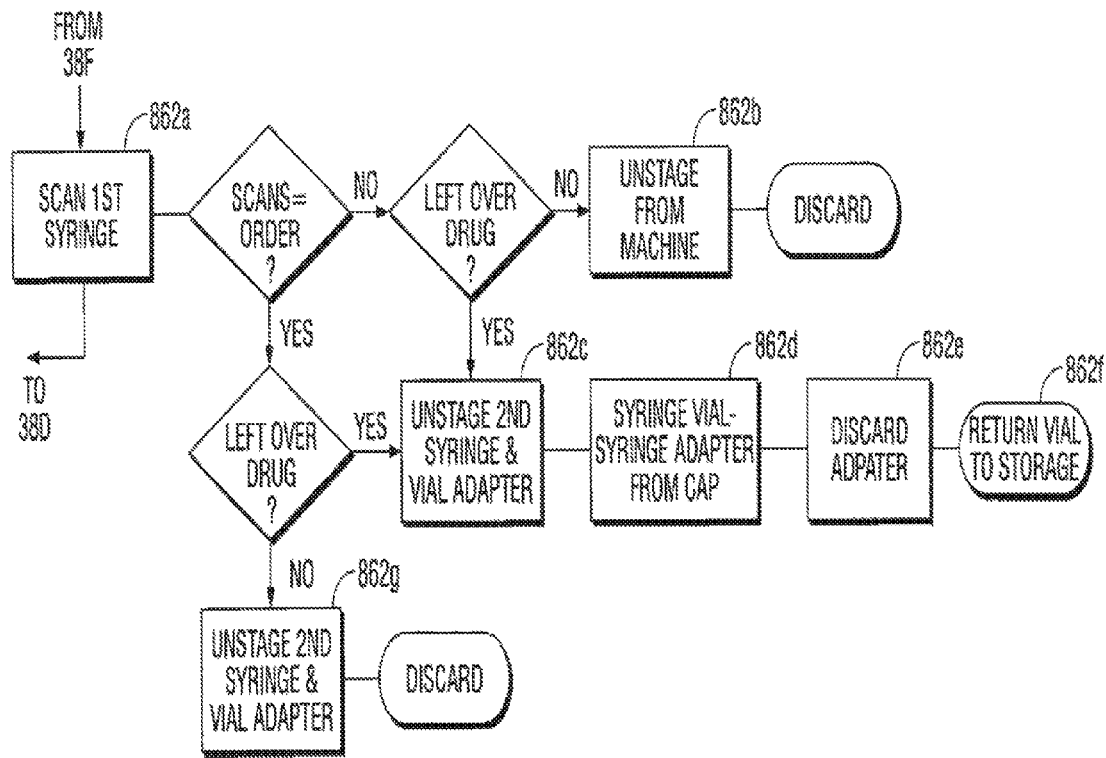
Figure 38H:
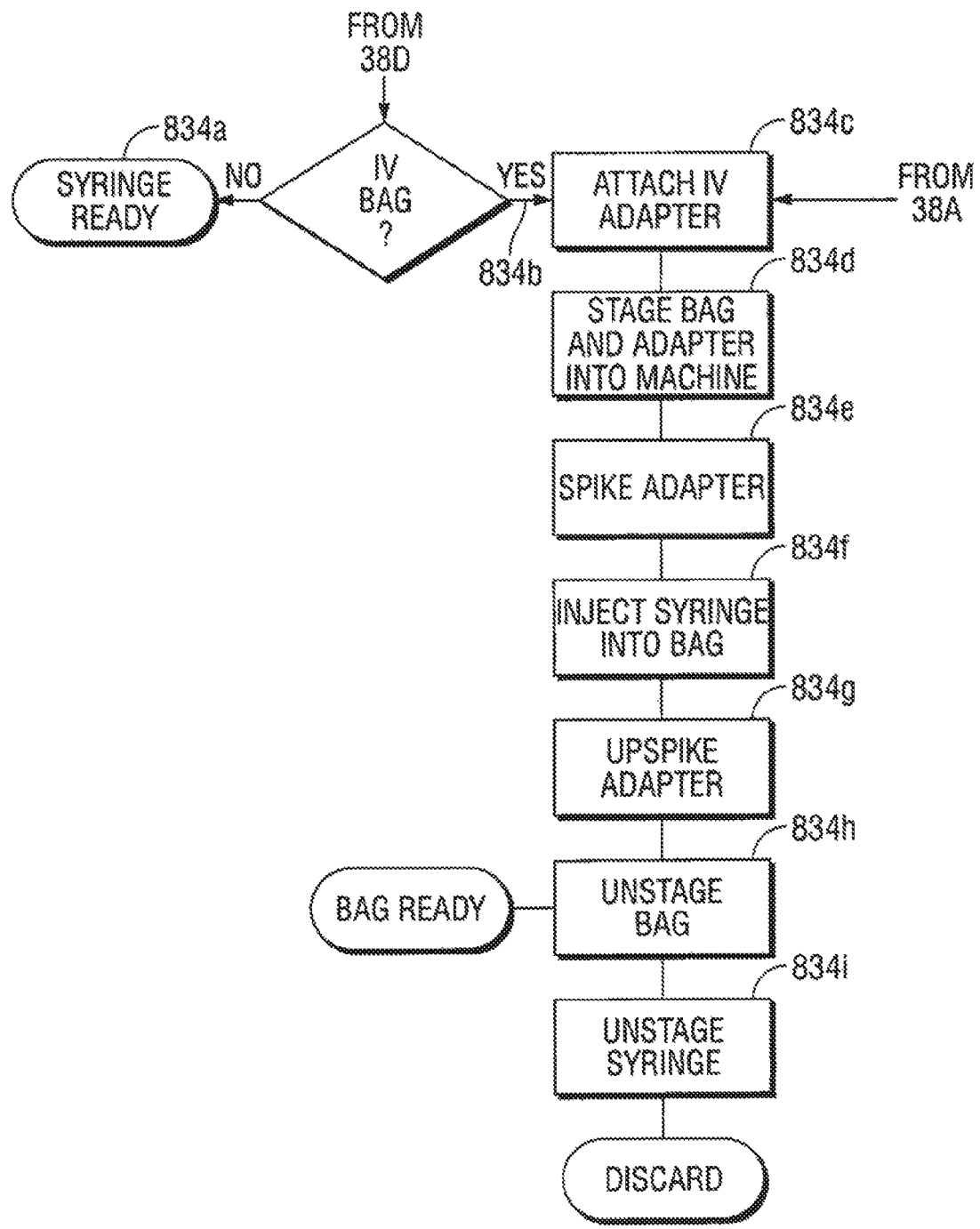

Simultaneously with the performance of some or all of Steps 832b-832g, as seen in FIG. 38H, following the scanning of the first syringe at Step 832a, then at Step 834a, if the first syringe is not to be used in an IV bag "B" (see FIG. 37), then the first syringe is ready. Alternatively, at Step 834b, if the first syringe is to be used in an IV bag "B", then an IV bag adapter 17 is attached to the first syringe at Step 834c. Then, at Step 834d, the IV bag "B" and the IV bag adapter 17 are staged in the machine, at Step 834e, the IV bag adapter 17 is spiked, at Step 834f, the contents of the first syringe are injected into the IV bag "B", and at Step 834g, IV bag "B" is unspiked. Then at Step 834h, the IV bag "B" is unstage as the IV bag "B" is ready, and at Step 834i, the first syringe is unstaged and discarded.

Referring back to FIG. 38A and with reference to FIG. 38E, if the order does require reconstitution, then, at Step 836, a diluent is pulled. Then, at Step 838a, a first and a second syringe are pulled and a first syringe adapter is pulled. At Step 838b, the order printed at Step 804, is affixed to the first syringe, and the first syringe adapter is attached to the first syringe. At Step 838c, the first syringe is filled with the diluent, at Step 838d, the first syringe is staged in the carousel 1100 of the preparation system 1000, and at Step 838e, the first syringe is weighed.

Substantially simultaneously therewith, at Step 840a, a vial "V" containing the medicament, a vial cap and a vial-syringe adapter 13 is pulled. At Step 840b the vial cap is connected to the medicament vial "V" and, at Step 840b, the vial-syringe adapter 13 is connected to the vial cap. At Step 840c the vial-syringe adapter 13 is connected to the vial cap. At Step 842a, the second syringe is connected to the vial-syringe adapter 13, and at Step 842b, the second syringe is connected to vial-syringe adapter 13 that was pulled at Step 838a. At Step 844a, the second syringe is staged in the carousel 1100 of the preparation system 1000, and at Step 844b the medicament vial "V" is spiked by the vial-syringe adapter 13. At Step 846, a negative pressure or vacuum is applied to the medicament vial while the diluent is injected into the medicament vial "V".

As seen in FIG. 38F, if there needs to be a dwell time or a swirling of the vial "V", at Step 848a, the vial "V" is removed from the carousel 1100 of the preparation system 1000, at Step 848b, the vial "V" is taken to a dwell/swirl location, at Step 848c, the vial "V" is then allowed to dwell or is swirled as needed, and at Step 848d, the vial "V" is then re-staged in the carousel 1100 of the preparation system 1000.

With continued reference to FIG. 38F, following dwelling/swirling of the vial "V" at steps 848a-848c, or if no dwelling/swirling is required, at Step 850, the first syringe, the second syringe and the vial "V" are inverted. At Step 852, a negative pressure or vacuum is applied to the vial "V" to extract contents from the vial "V" (e.g., the reconstituted medicament). At Step 854, the first syringe, the second syringe and the vial "V" are reverted. At Step 856, the vial "V" is unspiked. At Step 858a, the vial "V" is weighed. If the weight of the vial "V" is not correct or not equal to an expected weight, at Step 858b, the vial "V" is unstaged from the machine, and at Step 858c, the vial "V" is set aside for disposition. If the weight of the vial "V" is correct or is equal to an expected weight, then at Step 860, the vial "V" is scanned.

As seen in FIG. 38G, at Step 862a, the first syringe is scanned. If the information from the scan does not equal the information of the order and if there is no remaining drug, then at Step 862b, the first syringe is unstaged from the carousel 1100 of the preparation system 1000 and discarded. If the information from the scan does not equal the information of the order and if there is drug remaining, then at Step 862c, the second syringe and the vial-syringe adapter are unstaged from the carousel 1100 of the preparation system 1000. Then, at Step 862d, the vial-syringe adapter is separated from the cap of the vial "V", at Step 862e, the vial-syringe adapter is discarded and, at Step 862f, the vial "V" is returned to storage. If the information from the scan does equal the information of the order and if there is drug remaining, then Steps 862c-862f, are once again performed. If the information from the scan does equal the information of the order and if there is no drug remaining, then at Step 862g, the second syringe and the vial-syringe adapter are unstaged and discarded.

Following the scanning of the first syringe at Step 862a, and simultaneously with the performance of some or all of Steps 862b-862g, as seen in FIG. 38H, following the scanning of the first syringe at Step 862a, then Steps 834a-834h may be performed, as described above.

Alternatively, referring back to FIG. 38A, if the order is to require the use of an IV bag "B", then at Step 870, an IV bag "B" is pulled, and at step 872, the order is affixed to the IV bag "B". Following the fixation of the order to the IV bag "B", then Steps 834a-834h may be performed, as described above.

Figure 39A:
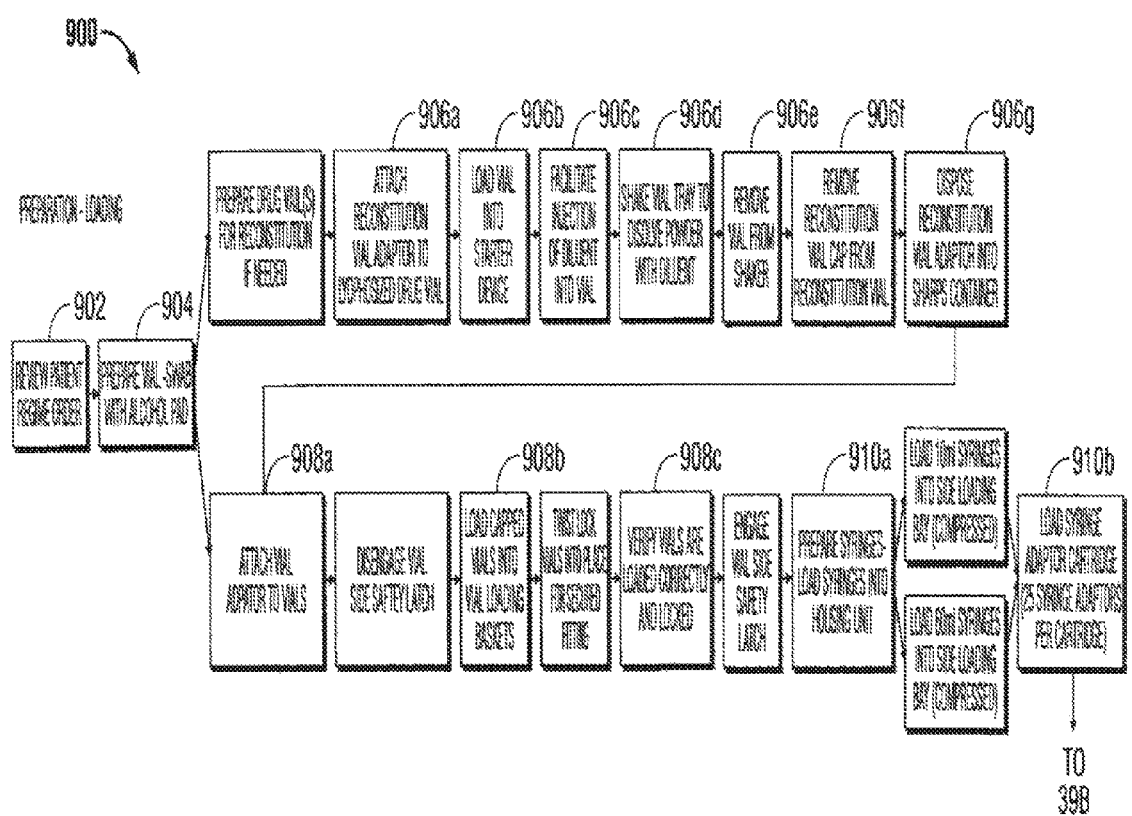
FIGS. 39A-39C is a process flow diagram illustrating a further method of use of the automated system of FIGS. 26-37 together with a medicament transport system of the present disclosure.
Figure 39B:
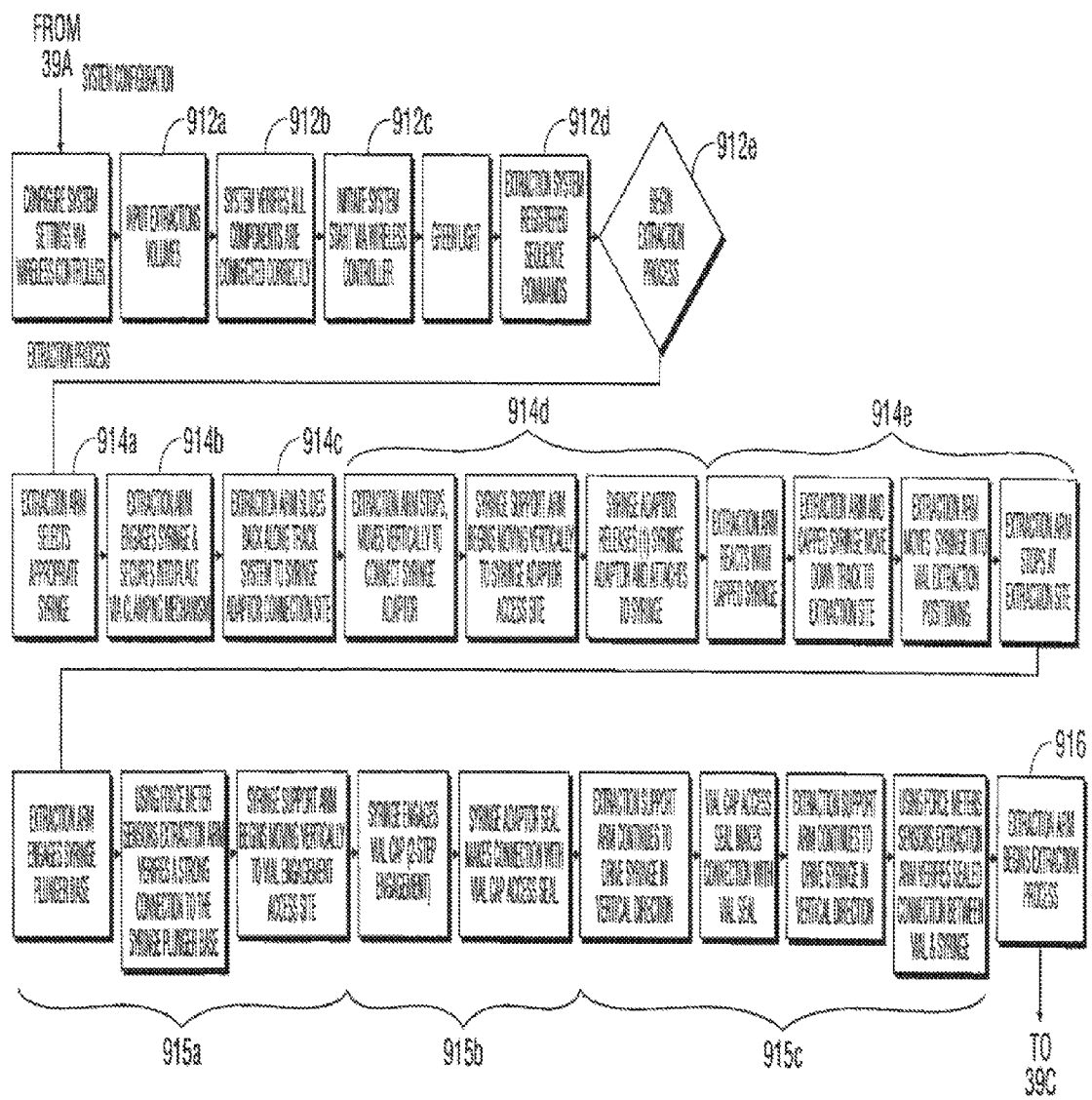
Figure 39C:
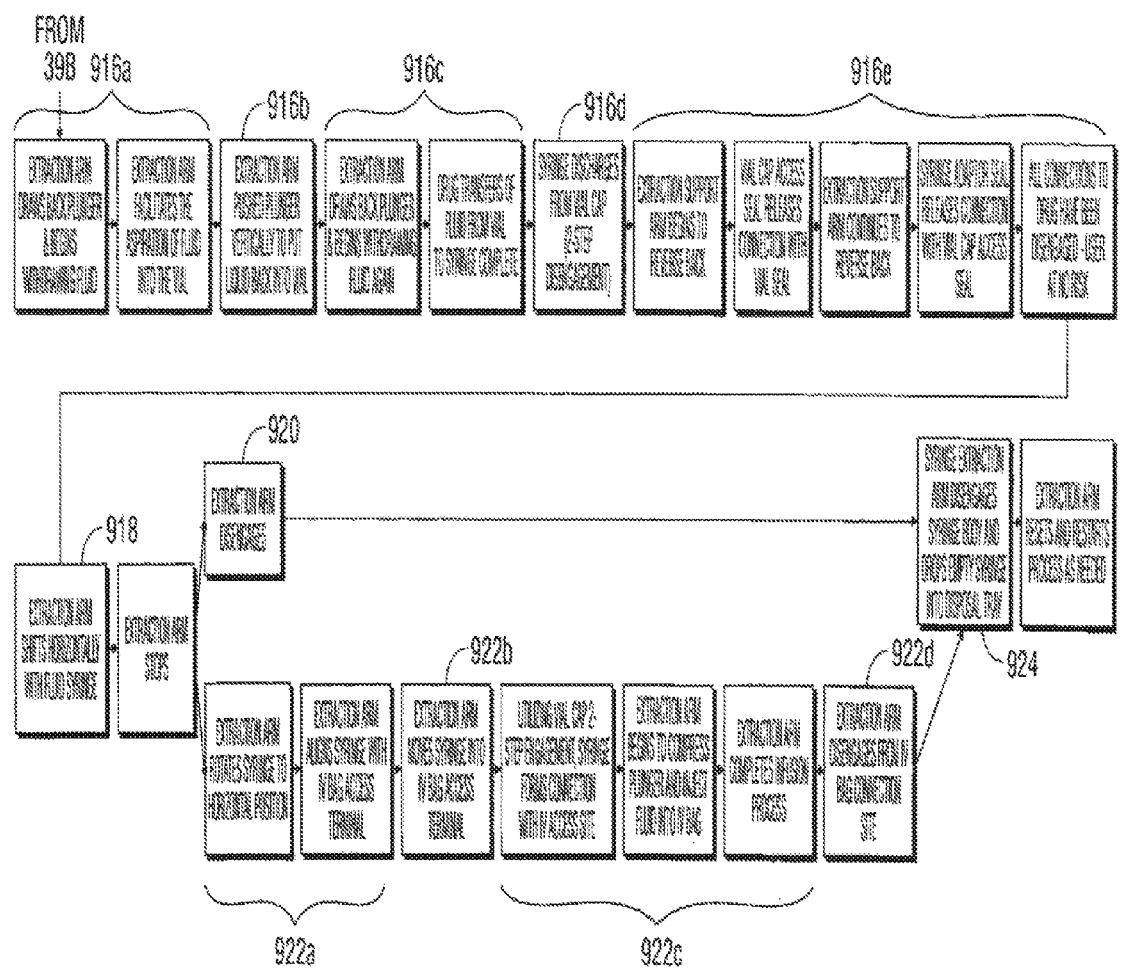

With reference to FIGS. 39A-39C, a further process of operating automated preparation system 1000, in accordance with the principles of the present disclosure, is provided. As seen in FIG. 39A, at step 900, the process is initiated by preparing and loading preparation system 1000. At Step 902, the patient regime order is reviewed, and at Step 904, the appropriate vial is swabbed with an alcohol pad or the like.

If the medicament in the vial "V" requires reconstitution, then at Step 906a, a reconstitution vial adapter assembly 13 is attached to the lyopholized medicament vial "V". At Step 906b the lyopholized medicament vial "V" is loaded into a shaker device, at Step 906c, a diluent is injected into the lyopholized medicament vial "V", and at Step 906d, the shaker device is activated to dissolve the powdered medicament with the diluent. At Step 906e, the vial "V" is removed from the shaker, at Step 906f, the reconstitution vial "V" adapter assembly 13 is removed, and at Step 906g, the reconstitution vial adapter assembly 13 is discarded.

Thereafter or if the medicament in the vial "V" does not require reconstitution, at Step 908a a vial adapter assembly 13 is attached to the vial "V", and at Step 908b, the vials "V" that are capped with the vial adapter assemblies 13 may be loaded into baskets or trays (not shown). The vials "V" may be locked into place by means of a twist lock arrangement or the like. At Step 908c, the proper loading of the vials "V" is verified.

At Step 910a, syringes are prepared by loading the syringes into the housing of preparation system 1000. Either 10 ml or 60 ml syringes (in a compressed state) are loaded. At Step 910b, a cartridge having a plurality of syringe adapters is loaded into the housing of preparation system 1000.

As seen in FIG. 39B, at Step 912, preparation system 1000 is configured. At Step 912a, the extraction volumes are imputed into system 1000, at Step 912b, preparation system 1000 verifies that all the components are connected correctly, at Step 912c, a system start is initiated (optionally via wireless controller), at Step 912d, preparation system 1000 registers sequence commands, and at Step 912e, an extraction process begins.

At Step 914, the extraction process is performed. At Step 914a, as seen in FIG. 39B, a component holder (CH) selects an appropriate syringe. At Step 914b, component holder (CH) engages the selected syringe and secures the selected syringe into place via clamping mechanism or fingers. At Step 914c, component holder (CH) is slid back along track or rails to a syringe adapter assembly connection site (i.e., transfer station (TS)). At Step 914d, a syringe adapter 11 is connected to the syringe "I". At Step 914e, the syringe "I" having the syringe adapter 11 connected thereto is moved by component holder (CH) to an extraction site (i.e., transfer station (TS)) corresponding to a loaded vial "V".

With component holder (CH) engaging a plunger of the syringe "I", at Step 915a, component holder (CH) moves the syringe to a vial engagement access site. At Step 915b, the syringe "I" engages the capped vial "V", wherein a seal of the syringe adapter 11 makes connection with a seal of the vial adapter 11. At Step 915c, component holder (CH) continues to advance the syringe "I" toward the vial "V" until a seal or stopper of the vial "V" is engaged by a seal of the vial adapter 11 and until a sealed connection is established between the vial "V" and the syringe "I". At Step 916, the extraction process begins.

As seen in FIG. 39C, at Step 916a, component holder (CH) withdraws the plunger relative to the syringe barrel of the syringe "I" to begin withdrawing fluid from the vial "V" and facilitate aspiration of fluid into the vial "V." At Step 916b, component holder (CH) advances the plunger relative to the barrel of the syringe "I" to inject fluid back into the vial "V". At step 916c, component holder (CH) once again withdraws the plunger relative to the barrel of the syringe "I" to again withdraw fluid from the vial "V" to complete the transfer of drug from the vial "V" to the syringe "I". At Step 916*d*, the syringe "I" filed with the medicament is disengaged from the vial adapter 13. At Step 916*e*, component holder (CH) moves away from the vial "V" such that the seal of the vial adapter 13 is disengaged from the seal of the vial "V" and the seal of the syringe adapter 11 is disengaged from the seal of the vial adapter 13.

At Step 918, as seen in FIG. 39C, component holder (CH), holding the filled syringe, is moved horizontally away from a tray (not shown) of vials "V". At Step 920, loading arm 714 may disengage and release the filled syringe. It is contemplated that at least one tray (not shown) may be provided within the carousel 1100 of the preparation system 1000. Each tray may be configured to store vials "V" prior to and following manipulation by component holders (CH) to the various stations about carousel 1100.

Alternatively, at Step 922*a*, as seen in FIG. 39C, component holder (CH) reorients the filled syringe "I" to align a nose of the syringe with an access terminal of an IV bag "B". At Step 922*b*, component holder (CH) moves the nose of the syringe into the access terminal of the IV bag "B". With the nose of the syringe connected to the access terminal of the IV bag "B", at Step 922*c*, component holder (CH) actuates the plunger of the syringe to inject the fluid of the syringe into the IV bag "B". At Step 922*d*, component holder (CH) disengages the syringe from the access terminal of the IV bag "B".

At Step 924, component holder (CH) disengages the used and empty syringe and drops the used and empty syringe to a disposal tray. The entire process may be repeated as many times as necessary.

With reference to FIGS. 41A-42C, the process of operating automated preparation system 1000 of FIGS. 38A-39C has been annotated to illustrate which sub-systems and/or stations, namely, a rotation station (RS), a weigh station (WS), a transfer station (TS), component holders (CH), at least one manipulator (M), at least one gripper (G), and at least one barcode scanner (BS), are used to achieve or accomplish the various steps and the like thereof.

Preparation system 1000 may include an error trapping protocol, wherein preparation system 1000 preforms and check and confirmation, at various stages of the process, to ensure that the correct components are being manipulated and that the correct materials (i.e., drugs) are being reconstituted and/or reformulated.

For example, as described above, the gripper (G) includes jaws that are opened closed to grasp and release vials "V", vial adapters 13, syringes "I" and syringe adapters 11. The jaws of gripper (G) are coordinated by way of a single pinion engaged in two racks, one per jaw set. The relative distance between the jaw sets can be measured directly with a linear measuring device, such as a linear potentiometer or a Linear Variable Displacement Transformer (LVDT), or by an angular measuring device, such as a rotary potentiometer or encoder. The pinion can be driven by an electric motor which can have either an encoder or resolver integrated into the main shaft.

In use, the distance measurements made by the gripper (G) can be used to qualify and quantify the component (e.g., syringe adapter 11, vial adapter 13) being grasped. The error trapping protocol can, for instance determine that the size of the component being grasped is not consistent with the programmed component size. The error trapping protocol can flag the operator to clear the anomaly, or it can shut down the compounding operation. Likewise, if a component has become mis-oriented within the equipment, the size will likely be reported as inconsistent with the expected size. The measurement can be used to quantify the diameter of a syringe, as well. With the diameter of the syringe known, the error trapping protocol can anticipate the required stroke required in the transfer station (TS) to accommodate the required volume.

A same or similar error trapping protocol can be implemented for the rotation station (RS) and for each of the component holders (CH).

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. An automatic or semi-automatic preparation system for forming a medicament solution from a vial containing one of a liquid and a non-liquid material, the preparation system comprising:
    a carousel configured to provide three axes of motion, the carousel including a manipulator having:
        at least one first rail defining a first axis;
        at least one second rail defining a second axis, the second axis being oriented orthogonal to the first axis;
        at least one third rail defining a third axis, the third axis being oriented orthogonal to the each of the first axis and the second axis;
        a first gear belt movably supported on at least one of the first rails, the second rails or the third rails, wherein the first gear belt, the first gear belt is movably supported on a series of sprockets;
        a second gear belt movably supported on at least one of the first rails, the second rails or the third rails, wherein the second gear belt, the first gear belt is movably supported on a series of sprockets; the first gear belt and the second gear belt being spaced apart from one another and being arranged in parallel with one another;
        at least one component holder supported on at least one of the first gearbelt and the second gear belt, each component holder being configured to selectively hold a syringe, a vial, a syringe adapter or a vial adapter; and
        at least one of a rotation station, a transfer station, and a weigh station disposed about the carousel;
    wherein the rotation station is configured for inverting and reverting a syringe and vial assembly;
    wherein the transfer station is configured for transferring material from a vial to a syringe; and
    wherein the weigh station is configured for weighing at least one of the syringe, the vial, and the syringe and vial assembly.

2. The preparation system according to claim 1, wherein the first gearbelt is movable in a first plane defined by the first axis that is defined by the first rail and the second axis that is defined by the second rail.

3. The preparation system according to claim 2, wherein the second gearbelt is movable in a second plane defined by the first axis that is defined by the first rail and the second axis that is defined by the second rail, the second plane being parallel to the first plane and being spaced a distance therefrom.

4. The preparation system according to claim 3, wherein at least one component holder is movable along the third axis, between the first plane and the second plane.

5. The preparation system according to claim 1, further comprising:
at least one syringe adapter manipulatable by a component holder of the carousel, each syringe adapter including:
a body portion defining a lumen therethrough; and
a seal member connected to a distal end of the body portion and extending across the lumen thereof; and
at least one vial adapter connectable to a neck of a vial and configured to receive the body portion of the syringe adapter, the vial adapter including:
a base having at least one retainer configured to engage the neck of the vial, the base defining an opening having a seal member disposed therewithin;
a stem extending from the base, the stem defining a lumen therethrough and being in operative communication with the opening of the base, the stem defining an opening through a wall thereof;
a needle shuttle valve slidably disposed within the lumen of the stem, the needle shuttle valve forming a fluid tight seal with the stem, the needle shuttle valve supporting a transfer needle such that the transfer needle extends from a first and a second end thereof and supporting a vacuum needle such that the vacuum needle extends from the first end of the needle shuttle valve; and
a vacuum cup slidably supported on the stem, the vacuum cup being in fluid tight contact with the stem and with the base, wherein a vacuum chamber is defined in the space between the base, the stem and the vacuum cup, the vacuum chamber being in fluid communication with the lumen of the stem through the opening formed in the wall of the stem.

6. The preparation system according to claim 5, further comprising a transfer station having a first condition in which the needle shuttle valve of the vial adapter is in a retracted position such that the transfer needle and the vacuum needle do not extend through the seal member of the base of the vial adapter, and the vacuum cup is in an advanced position such that the volume of the vacuum chamber is at a minimum.

7. The preparation system according to claim 6, wherein the transfer station has a second condition in which the body portion of the syringe adapter is advanced through the lumen of the stem such that the second end of the transfer needle penetrates through the seal member of the body portion and the needle shuttle valve is advanced through the lumen of the stem to penetrate the first end of the transfer needle and a tip of the vacuum needle through the seal member of the vial adapter, and wherein the vacuum needle is brought into fluid communication with the opening formed in the wall of the stem.

8. The preparation system according to claim 7, wherein the transfer station has a third condition in which the vacuum cup is moved to a proximal position thereby enlarging the vacuum chamber and drawing a vacuum through the vacuum needle.

9. The preparation system according to claim 8, wherein the carousel is configured to connect a syringe adapter to a syringe, and to transport the assembled syringe and syringe adapter to a vial having a vial adapter connected thereto.

10. The preparation system according to claim 9, wherein the carousel is configured to connect the syringe adapter, that is connected to the syringe, to the vial adapter, that is connected to the vial.

11. The preparation system according to claim 1, wherein a component holder includes a gripper having:
a first pair of fixed, spaced apart jaws, the first pair of jaws including a first jaw and a second jaw; and
a second pair of fixed, spaced apart jaws, the second pair of jaws including a first jaw and a second jaw;
wherein the first pair of jaws is translatable relative to the second pair of jaws; and
wherein the first jaw of the first pair of jaws is interposed between the second pair of jaws, and the second jaw of the second pair of jaws is interposed between the first pair of jaws.

12. The preparation system according to claim 11, wherein operation of the gripper includes translation of the first pair of jaws relative to the second pair of jaws to grip a component at:
a first gripping position located between the first jaw of the first pair of jaws and the first jaw of the second pair of jaws;
a second gripping position located between the second jaw of the first pair of jaws and the first jaw of the second pair of jaws; and
a third gripping position located between the second jaw of the first pair of jaws and the second jaw of the second pair of jaws.

13. The preparation system according to claim 12, wherein the first pair of jaws supports a rack, and the second pair of jaws supports a rack, and wherein a pinion interconnects the each rack, wherein rotation of the pinion results in axial translation of the first pair of jaws and the second pair of jaws relative to one another.

14. The preparation system according to claim 12, further comprising an error trapping protocol to check and confirm that correct components are being manipulated about the carousel relative to one another,
wherein, for a particular stage in the process, the error trapping protocol compares a known dimension of a component expected in the gripper against a real-time dimension of a components gripped within the gripper, and triggers an alert when a known expected dimension for the component is different than a real-time measured dimension of the component that is present in the gripper.

* * * * *